US011053313B2

(12) United States Patent
Kondoh et al.

(10) Patent No.: US 11,053,313 B2
(45) Date of Patent: Jul. 6, 2021

(54) ANTI-CLDN-5 ANTIBODY, AND DRUG CONTAINING SAID ANTIBODY

(71) Applicants: OSAKA UNIVERSITY, Osaka (JP); NATIONAL UNIVERSITY CORPORATION EHIME UNIVERSITY, Ehime (JP); FUJIFILM Wako Pure Chemical Corporation, Osaka (JP)

(72) Inventors: Masuo Kondoh, Osaka (JP); Kiyohito Yagi, Osaka (JP); Takefumi Doi, Osaka (JP); Yoshiaki Okada, Osaka (JP); Yosuke Hashimoto, Osaka (JP); Tatsuya Sawasaki, Ehime (JP); Hiroyuki Takeda, Ehime (JP); Kohki Endo, Hyogo (JP); Maki Tamura, Hyogo (JP)

(73) Assignees: OSAKA UNIVERSITY, Osaka (JP); NATIONAL UNIVERSITY CORPORATION EHIME UNIVERSITY, Ehime (JP); FUJIFILM WAKO PURE CHEMICAL CORPORATION, Osaka (JP)

( * ) Notice: Subject to any disclaimer, the term of this patent is extended or adjusted under 35 U.S.C. 154(b) by 0 days.

(21) Appl. No.: 16/611,678

(22) PCT Filed: Apr. 26, 2018

(86) PCT No.: PCT/JP2018/016975
§ 371 (c)(1),
(2) Date: Nov. 7, 2019

(87) PCT Pub. No.: WO2018/207638
PCT Pub. Date: Nov. 15, 2018

(65) Prior Publication Data
US 2020/0148765 A1 May 14, 2020

(30) Foreign Application Priority Data

May 8, 2017 (JP) .............................. JP2017-092658

(51) Int. Cl.
*A61K 39/395* (2006.01)
*C07K 16/18* (2006.01)
*C07K 16/28* (2006.01)

(52) U.S. Cl.
CPC .......... *C07K 16/28* (2013.01); *C07K 2317/33* (2013.01); *C07K 2317/565* (2013.01)

(58) Field of Classification Search
None
See application file for complete search history.

(56) References Cited

U.S. PATENT DOCUMENTS

2009/0202556 A1 8/2009 Ohta et al.
2011/0064792 A1 3/2011 Humphries et al.

FOREIGN PATENT DOCUMENTS

JP 2003-524384 8/2003
JP 2016-47845 4/2016
(Continued)

OTHER PUBLICATIONS

International Search Report dated Jul. 31, 2018 in International (PCT) Application No. PCT/JP2018/016975.
(Continued)

*Primary Examiner* — Aurora M Fontainhas
(74) *Attorney, Agent, or Firm* — Wenderoth, Lind & Ponack, L.L.P.

(57) ABSTRACT

An object of the present invention is to provide a novel molecule which has high specificity to CLDN-5 and recognizes an extracellular domain of CLDN-5. The object is achieved by an antibody which specifically recognizes a
(Continued)

three-dimensional structure or a primary structure of an extracellular domain of a Claudin-5 protein.

12 Claims, 19 Drawing Sheets

Specification includes a Sequence Listing.

(56) References Cited

FOREIGN PATENT DOCUMENTS

| JP | 2016-525558 | 8/2016 |
|---|---|---|
| WO | 00/26360 | 5/2000 |
| WO | 2008/114733 | 9/2008 |
| WO | 2009/028663 | 3/2009 |
| WO | 2011/057788 | 5/2011 |
| WO | 2015/014657 | 2/2015 |

OTHER PUBLICATIONS

Liao et al., "Specific Binding of a Mutated Fragment of Clostridium Perfringens Enterotoxin to Endothelial Claudin-5 and Its Modulation of Cerebral Vascular Permeability", Neuroscience, Apr. 13, 2016, vol. 327, pp. 53-63.

Nitta et al., "Size-selective loosening of the blood-brain barrier in claudin-5-deficient mice", J. Cell Biol., May 12, 2003, vol. 161, No. 3, pp. 653-660.

Escudero-Esparza et al., "Claudin-5 is involved in breast cancer cell motility through the N-WASP and ROCK signaling pathways", Journal of Experimental & Clinical Cancer Research, 2012, vol. 31, No. 43 , pp. 1-18.

Protze et al., "Directed structural modification of Clostridium perfringens enterotoxin to enhance binding to claudin-5", Cell. Mol. Life Sci., 2015, vol. 72, pp. 1417-1432.

Campbell et al., "RNAi-mediated reversible opening of the blood-brain barrier", The Journal of Gene Medicine, 2008, vol. 10, pp. 930-947.

Staat et al., "Mode of action of claudin peptidomimetics in the transient opening of cellular tight junction barriers", Biomaterials, 2015, vol. 54, pp. 9-20.

Extended European Search Report dated Jan. 13, 2021 in European Patent Application No. 18798023.0.

"Claudin 5 (JM11-22)", Hangzhou HuaAn Biotechnology Co., Ltd. Product Type: Recombinant rabbit monoclonal lgG Claudin 5 (JM11-22) (Mar. 3, 2017) & Data Apps Lab: Claudin 5 Antibody (MA5-32614).

Krause et al., "Structure and Function of Extracellular Claudin Domains", Molecular Structure and Function of the Tight Junction: from basic mechanisms to clinical manifestations blackwell publishing, 9600 Garsington rd, Oxford OX4 2DQ, Oxen, UK Series: Annals of the New York Academy of Sciences (ISSN 0077-8923(PRINT)), May 1, 2009 (2009-85-81), pp. 34-43.

Rahner et al., "Heterogeneity in Expression and Subcellular Localization of Claudius 2, 3, 4, and 5 in the Rat Liver, Pancreas and Gut", Gastroenterology, vol. 120, No. 2, 2001, pp. 411-422.

Hashimoto et al., "Current progress in a second-generation claudin binder anti-claudin antibody, for clinical application", Drug Discovery Today, vol. 21, No. 10, 2016, pp. 1711-1718.

Hashimoto et al., "Claudin-5-Binders Enhance Permeation of Solutes across the Blood-Brain Barrier in a Matnmalian Model", Journal of Pharmacology and Experimental Therapeutics, vol. 363, No. 2, 2017, pp. 275-283.

Hashimoto et al., "Engineered membrane protein antigens successfully induce antibodies against extracellular regions of claudin-5", Scientific Reports, 2018, vol. 8. No. 1, pp. 1-12.

Hashimoto et al., "Tight junction modulation at the blood-brain barrier: Current and future perspectives", BBA—Biomembranes, 2020, vol. 1862, No. 9, pp. 1-11.

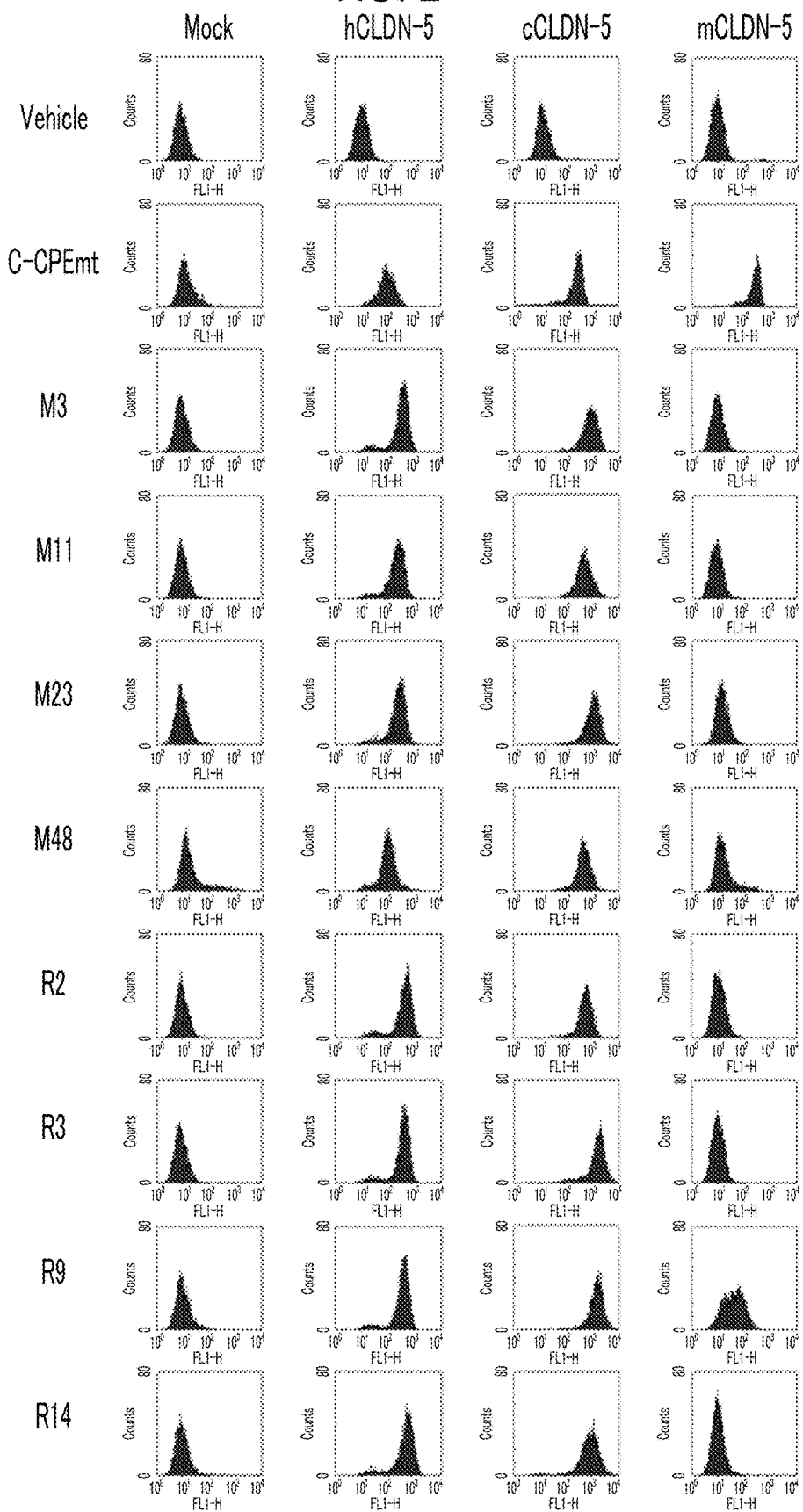

FIG. 9
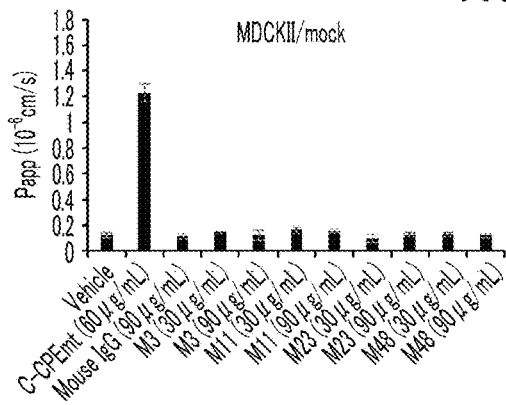
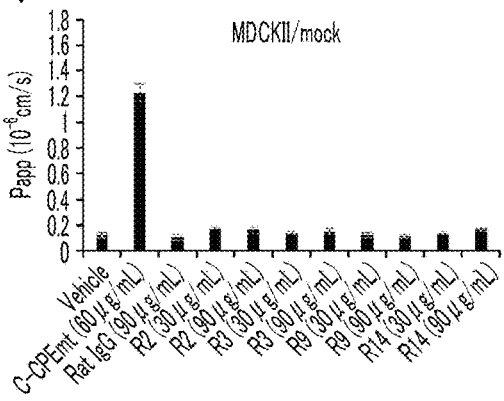
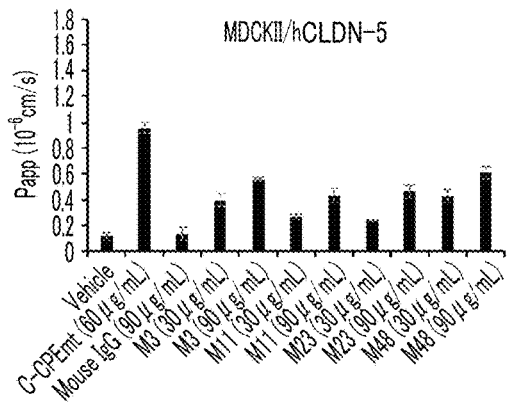
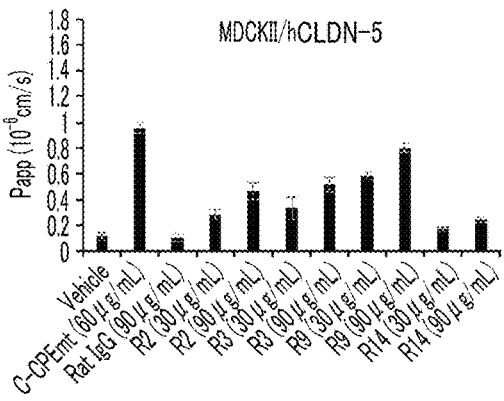
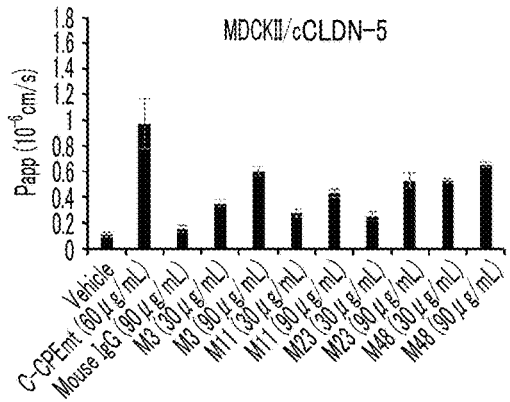
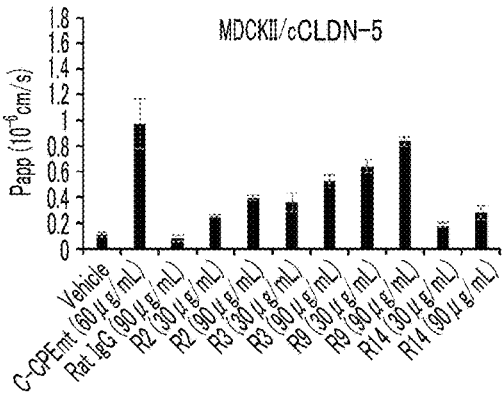
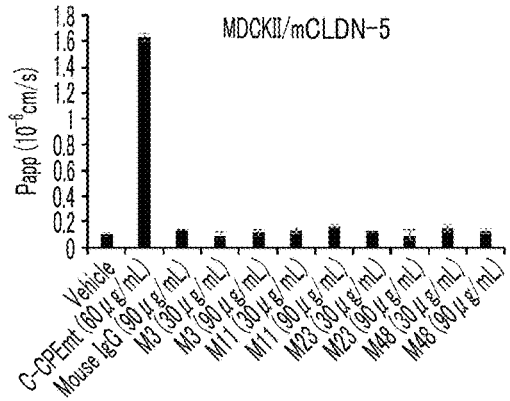
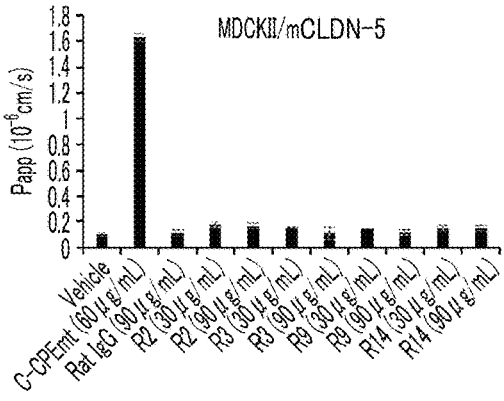

SEQUENCE LISTING

```
<160> NUMBER OF SEQ ID NOS: 230

<210> SEQ ID NO 1
<211> LENGTH: 117
<212> TYPE: PRT
<213> ORGANISM: Artificial Sequence
<220> FEATURE:
<223> OTHER INFORMATION: M3 VH

<400> SEQUENCE: 1

Glu Val Gln Leu Gln Gln Ser Gly Pro Glu Leu Val Lys Pro Gly Ala
1               5                   10                  15

Ser Val Lys Ile Ser Cys Lys Ala Ser Gly Tyr Ser Phe Thr Gly Tyr
            20                  25                  30

Tyr Met Asn Trp Val Lys Gln Ser Pro Glu Lys Ser Leu Glu Trp Ile
        35                  40                  45

Gly Asp Ile Asn Pro Ser Thr Gly Gly Ala Thr Tyr Asn Gln Lys Phe
    50                  55                  60

Lys Ala Lys Ala Thr Leu Thr Val Asp Lys Ser Ser Ser Thr Ala Tyr
65                  70                  75                  80

Met Gln Leu Lys Ser Leu Thr Ser Glu Asp Ser Ala Val Phe Tyr Cys
                85                  90                  95

Ala Leu Tyr Ser Asn Tyr Gly Phe Val Tyr Trp Gly Gln Gly Thr Leu
            100                 105                 110

Val Thr Val Ser Ala
        115

<210> SEQ ID NO 2
<211> LENGTH: 112
<212> TYPE: PRT
<213> ORGANISM: Artificial Sequence
<220> FEATURE:
<223> OTHER INFORMATION: M3 VL
```

```
<400> SEQUENCE: 2

Asp Val Val Met Thr Gln Thr Pro Leu Thr Leu Ser Val Thr Leu Gly
1               5                   10                  15

Gln Pro Ala Ser Ile Ser Cys Lys Ser Ser Gln Ser Leu Leu Tyr Ser
            20                  25                  30

Asp Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Leu Tyr Tyr Cys Val Gln Gly
                85                  90                  95

Ile His Phe Pro Arg Thr Phe Gly Gly Gly Thr Lys Leu Glu Ile Lys
            100                 105                 110

<210> SEQ ID NO 3
<211> LENGTH: 117
<212> TYPE: PRT
<213> ORGANISM: Artificial Sequence
<220> FEATURE:
<223> OTHER INFORMATION: M11 VH

<400> SEQUENCE: 3

Gln Val Gln Leu Lys Gln Ser Gly Pro Gly Leu Val Gln Pro Ser Gln
1               5                   10                  15

Ser Leu Ser Ile Thr Cys Thr Val Ser Gly Phe Ser Leu Ile Arg Tyr
            20                  25                  30

Gly Val His Trp Val Arg Gln Ser Pro Gly Lys Gly Leu Glu Trp Leu
        35                  40                  45

Gly Val Lys Trp Ser Gly Gly Ser Thr Asp Tyr Asn Gly Ala Phe Lys
    50                  55                  60

Ser Arg Leu Ser Ile Ser Lys Asp Asn Ser Lys Ser Gln Val Phe Phe
65                  70                  75                  80

Lys Met Asn Ser Leu Gln Ala Asp Asp Thr Ala Ile Tyr Tyr Cys Ala
                85                  90                  95

Arg Gly Leu Asp Gly Tyr Tyr Val Pro Asp Val Trp Gly Thr Gly Thr
            100                 105                 110

Ser Val Thr Val Ser
        115

<210> SEQ ID NO 4
<211> LENGTH: 108
<212> TYPE: PRT
<213> ORGANISM: Artificial Sequence
<220> FEATURE:
<223> OTHER INFORMATION: M11 VL

<400> SEQUENCE: 4

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Ser Thr Asn
            20                  25                  30

Val Ala Trp Tyr Gln Gln Lys Pro Gly Gln Ser Pro Thr Leu Leu Ile
        35                  40                  45

Tyr Trp Ala Ser Thr Arg His Thr Gly Val Pro Asp Arg Phe Thr Gly
    50                  55                  60
```

```
Ser Gly Ser Gly Thr Asp Tyr Thr Leu Thr Ile Ser Ser Val Gln Ala
 65                  70                  75                  80

Glu Asp Leu Ala Leu Tyr Tyr Cys Gln Gln His Tyr Ser Thr Pro Leu
                 85                  90                  95

Thr Phe Gly Ala Gly Thr Lys Leu Glu Leu Arg Arg
            100                 105

<210> SEQ ID NO 5
<211> LENGTH: 122
<212> TYPE: PRT
<213> ORGANISM: Artificial Sequence
<220> FEATURE:
<223> OTHER INFORMATION: M23 VH

<400> SEQUENCE: 5

Glu Val Gln Leu Gln Gln Ser Gly Pro Val Leu Val Lys Pro Gly Pro
  1               5                  10                  15

Ser Val Met Ile Ser Cys Lys Ala Ser Gly Phe Thr Phe Thr Asp Tyr
                 20                  25                  30

Tyr Met His Trp Val Lys Gln Ser His Gly Lys Ser Leu Glu Trp Ile
             35                  40                  45

Gly Leu Val Tyr Pro Tyr Asn Gly Gly Thr Asp Tyr Asn Gln Lys Phe
 50                  55                  60

Lys Gly Lys Ala Thr Leu Thr Val Asp Thr Ser Ser Thr Ala Tyr
 65                  70                  75                  80

Met Glu Leu Asn Ser Leu Thr Ser Glu Asp Ser Ala Val Tyr Tyr Cys
                 85                  90                  95

Ala Arg Cys Leu Tyr Asp Gly Leu Tyr Phe Tyr Ala Met Asp Tyr Trp
                100                 105                 110

Gly Gln Gly Thr Ser Val Thr Val Ser Ser
            115                 120

<210> SEQ ID NO 6
<211> LENGTH: 114
<212> TYPE: PRT
<213> ORGANISM: Artificial Sequence
<220> FEATURE:
<223> OTHER INFORMATION: M23 VL

<400> SEQUENCE: 6

Asp Ile Val Met Ser Gln Ser Pro Ser Ser Leu Ala Val Ser Ala Gly
  1               5                  10                  15

Glu Lys Val Thr Met Thr Cys Lys Ser Ser Gln Ser Leu Leu Asn Ser
                 20                  25                  30

Arg Ala Arg Lys Asn Tyr Leu Ala Trp Tyr Gln Gln Lys Ala Gly Gln
             35                  40                  45

Ser Pro Lys Leu Leu Met Tyr Trp Ala Ser Thr Arg Glu Ser Gly Val
 50                  55                  60

Pro Asp Arg Phe Thr Ala Ser Gly Ser Gly Thr Asp Phe Thr Leu Thr
 65                  70                  75                  80

Ile Ser Ser Val Gln Ala Glu Asp Leu Ala Val Phe Tyr Cys Lys Gln
                 85                  90                  95

Ser Tyr Asn Leu Pro Trp Thr Phe Gly Gly Gly Thr Lys Leu Glu Ile
                100                 105                 110

Lys Arg

<210> SEQ ID NO 7
<211> LENGTH: 120
```

```
<212> TYPE: PRT
<213> ORGANISM: Artificial Sequence
<220> FEATURE:
<223> OTHER INFORMATION: M29 VH

<400> SEQUENCE: 7
```

| | | | | | | | | | | | | | | | |
|---|---|---|---|---|---|---|---|---|---|---|---|---|---|---|---|
| Glu | Val | Gln | Leu | Val | Glu | Ser | Gly | Gly | Gly | Leu | Val | Gln | Pro | Lys | Gly |
| 1 | | | | 5 | | | | | 10 | | | | | 15 | |
| Ser | Leu | Lys | Leu | Ser | Cys | Ala | Ala | Ser | Gly | Phe | Thr | Phe | Asn | Ile | Tyr |
| | | | 20 | | | | | 25 | | | | | 30 | | |
| Ala | Met | His | Trp | Val | Arg | Gln | Ala | Pro | Gly | Lys | Gly | Leu | Glu | Trp | Val |
| | | 35 | | | | | 40 | | | | | 45 | | | |
| Ala | Arg | Ile | Arg | Ser | Lys | Ser | Ser | Asn | Tyr | Ala | Thr | Tyr | Tyr | Val | Asp |
| | 50 | | | | | 55 | | | | | 60 | | | | |
| Ser | Val | Lys | Asp | Arg | Phe | Ile | Ile | Ser | Arg | Asp | Asp | Ser | Gln | Ser | Met |
| 65 | | | | | 70 | | | | | 75 | | | | | 80 |
| Leu | Tyr | Leu | Gln | Val | Asn | Asn | Leu | Lys | Thr | Glu | Asp | Thr | Ala | Met | Tyr |
| | | | | 85 | | | | | 90 | | | | | 95 | |
| Tyr | Cys | Val | Arg | Glu | Gly | Asn | Trp | Asp | Cys | Phe | Asp | Tyr | Trp | Gly | Gln |
| | | | 100 | | | | | 105 | | | | | 110 | | |
| Gly | Thr | Thr | Leu | Thr | Val | Ser | Ser | | | | | | | | |
| | | 115 | | | | | 120 | | | | | | | | |

```
<210> SEQ ID NO 8
<211> LENGTH: 112
<212> TYPE: PRT
<213> ORGANISM: Artificial Sequence
<220> FEATURE:
<223> OTHER INFORMATION: M29 VL

<400> SEQUENCE: 8
```

| | | | | | | | | | | | | | | | |
|---|---|---|---|---|---|---|---|---|---|---|---|---|---|---|---|
| Asp | Ile | Val | Met | Ser | Gln | Ser | Pro | Ser | Ser | Leu | Pro | Val | Ser | Val | Gly |
| 1 | | | | 5 | | | | | 10 | | | | | 15 | |
| Gln | Lys | Val | Thr | Met | Thr | Cys | Lys | Ser | Ser | Gln | Ser | Leu | Leu | Tyr | Thr |
| | | | 20 | | | | | 25 | | | | | 30 | | |
| Ser | Asn | Gln | Lys | Asn | Tyr | Leu | Ala | Trp | Tyr | Gln | Gln | Lys | Pro | Gly | Gln |
| | | 35 | | | | | 40 | | | | | 45 | | | |
| Ser | Pro | Lys | Leu | Leu | Ile | Tyr | Trp | Ala | Ser | Thr | Arg | Glu | Ser | Gly | Val |
| | 50 | | | | | 55 | | | | | 60 | | | | |
| Pro | Asp | Arg | Phe | Thr | Gly | Ser | Gly | Ser | Gly | Thr | Asp | Phe | Thr | Leu | Thr |
| 65 | | | | | 70 | | | | | 75 | | | | | 80 |
| Ile | Ser | Ser | Val | Lys | Ala | Glu | Asp | Leu | Ala | Ile | Tyr | Tyr | Cys | Gln | Gln |
| | | | | 85 | | | | | 90 | | | | | 95 | |
| Tyr | Tyr | Arg | Tyr | His | Thr | Phe | Gly | Gly | Gly | Thr | Arg | Leu | Glu | Ile | Lys |
| | | | 100 | | | | | 105 | | | | | 110 | | |

```
<210> SEQ ID NO 9
<211> LENGTH: 119
<212> TYPE: PRT
<213> ORGANISM: Artificial Sequence
<220> FEATURE:
<223> OTHER INFORMATION: M48 VH

<400> SEQUENCE: 9
```

| | | | | | | | | | | | | | | | |
|---|---|---|---|---|---|---|---|---|---|---|---|---|---|---|---|
| Gln | Ala | Tyr | Leu | Gln | Gln | Ser | Gly | Ala | Glu | Leu | Val | Arg | Pro | Gly | Ala |
| 1 | | | | 5 | | | | | 10 | | | | | 15 | |
| Ser | Val | Lys | Met | Ser | Cys | Lys | Ala | Ser | Gly | Tyr | Thr | Phe | Thr | Ser | Tyr |
| | | | 20 | | | | | 25 | | | | | 30 | | |
| Asn | Met | His | Trp | Val | Lys | Lys | Thr | Arg | Arg | Gln | Gly | Leu | Glu | Trp | Ile |

```
                35                  40                  45
Gly Ala Ile Ser Pro Gly Asn Gly Asn Thr Ser Tyr Asn Gln Lys Phe
            50                  55                  60
Lys Gly Lys Ala Thr Leu Thr Val Asp Lys Ser Ser Thr Ala Tyr
65                  70                  75                  80
Met Gln Leu Ser Ser Leu Thr Ser Glu Asp Ser Ala Val Tyr Phe Cys
                85                  90                  95
Ala Arg Asp Asp Gly Tyr Tyr Gly Ala Leu Asp Tyr Trp Gly Gln Gly
                100                 105                 110
Thr Ser Val Thr Val Ser Ser
            115

<210> SEQ ID NO 10
<211> LENGTH: 106
<212> TYPE: PRT
<213> ORGANISM: Artificial Sequence
<220> FEATURE:
<223> OTHER INFORMATION: M48 VL

<400> SEQUENCE: 10

Asp Ile Val Leu Thr Gln Ser Pro Ala Thr Leu Ser Val Thr Pro Gly
1               5                   10                  15
Glu Ser Val Ser Leu Ser Cys Arg Ala Ser Gln Gly Ile Ser Thr Ser
                20                  25                  30
Ile His Trp Tyr Gln Gln Lys Ser Asn Glu Ser Pro Arg Leu Leu Ile
            35                  40                  45
Arg Tyr Ala Ser Gln Ser Ile Ser Arg Ile Pro Ser Arg Phe Ser Gly
        50                  55                  60
Ser Gly Ser Gly Thr Asp Phe Thr Leu Thr Ile Asn Gly Val Glu Ser
65                  70                  75                  80
Glu Asp Leu Ser Val Tyr Tyr Cys Gln Gln Ser Tyr Asn Leu Pro Leu
                85                  90                  95
Thr Phe Gly Ser Gly Thr Lys Leu Glu Ile
                100                 105

<210> SEQ ID NO 11
<211> LENGTH: 119
<212> TYPE: PRT
<213> ORGANISM: Artificial Sequence
<220> FEATURE:
<223> OTHER INFORMATION: R2 VH

<400> SEQUENCE: 11

Gln Val Gln Leu Lys Glu Ser Gly Pro Gly Leu Val Gln Pro Ser Gln
1               5                   10                  15
Thr Leu Ser Leu Thr Cys Thr Val Ser Gly Leu Ser Leu Ile Arg Asn
                20                  25                  30
Ser Val Ser Trp Ile Arg Gln Pro Pro Gly Lys Gly Leu Glu Trp Met
            35                  40                  45
Gly Val Ile Trp Ser Asn Gly Gly Thr Glu Tyr Asn Ser Thr Val Lys
        50                  55                  60
Ser Arg Leu Ser Ile Ser Arg Asp Thr Ser Lys Asn Gln Val Phe Leu
65                  70                  75                  80
Lys Met Asn Ser Leu Gln Thr Glu Asp Ser Ala Met Phe Phe Cys Ala
                85                  90                  95
Arg Thr Pro Asp Gly Tyr Pro Tyr Phe Asp Tyr Trp Gly Gln Gly
                100                 105                 110
```

Val Met Val Thr Val Ser Ser
        115

<210> SEQ ID NO 12
<211> LENGTH: 106
<212> TYPE: PRT
<213> ORGANISM: Artificial Sequence
<220> FEATURE:
<223> OTHER INFORMATION: R2 VL

<400> SEQUENCE: 12

Asp Ile Val Leu Thr Gln Ser Pro Ala Thr Leu Ser Val Thr Pro Gly
1               5                   10                  15

Glu Ser Val Ser Leu Ser Cys Arg Ala Ser Gln Gly Ile Ser Thr Ser
            20                  25                  30

Ile His Trp Tyr Gln Gln Lys Ser Asn Glu Ser Pro Arg Leu Leu Ile
        35                  40                  45

Arg Tyr Ala Ser Gln Ser Ile Ser Arg Ile Pro Ser Arg Phe Ser Gly
    50                  55                  60

Ser Gly Ser Gly Thr Asp Phe Thr Leu Thr Ile Asn Gly Val Glu Ser
65                  70                  75                  80

Glu Asp Leu Ser Val Tyr Tyr Cys Gln Gln Ser Tyr Asn Leu Pro Leu
                85                  90                  95

Thr Phe Gly Ser Gly Thr Lys Leu Glu Ile
            100                 105

<210> SEQ ID NO 13
<211> LENGTH: 117
<212> TYPE: PRT
<213> ORGANISM: Artificial Sequence
<220> FEATURE:
<223> OTHER INFORMATION: R3 VH

<400> SEQUENCE: 13

Glu Val Gln Leu Val Glu Ser Gly Gly Gly Leu Val Gln Pro Gly Arg
1               5                   10                  15

Ser Leu Lys Leu Ser Cys Ala Ala Ser Gly Phe Thr Phe Ser Asp Tyr
            20                  25                  30

Tyr Met Ala Trp Val Arg Gln Ala Pro Lys Lys Gly Leu Glu Trp Val
        35                  40                  45

Ala Ser Ile Ser Tyr Glu Gly Arg Asn Thr Tyr Tyr Gly Asp Ser Val
    50                  55                  60

Lys Gly Arg Phe Thr Ile Ser Arg Asp Asn Ala Lys Ser Thr Leu Tyr
65                  70                  75                  80

Leu Gln Met Lys Ser Leu Arg Ser Glu Asp Thr Ala Thr Tyr Tyr Cys
                85                  90                  95

Thr Arg His Pro Arg Arg Tyr Phe Asp Tyr Trp Gly Gln Gly Val Met
            100                 105                 110

Val Thr Val Ser Ser
        115

<210> SEQ ID NO 14
<211> LENGTH: 112
<212> TYPE: PRT
<213> ORGANISM: Artificial Sequence
<220> FEATURE:
<223> OTHER INFORMATION: R3 VL

<400> SEQUENCE: 14

Asp Ile Val Met Thr Gln Ser Pro Ser Ser Leu Ala Val Ser Ala Gly

```
                1               5                    10                   15
              Glu Thr Val Thr Met Asn Cys Arg Ser Ser Gln Ser Leu Phe Ser Ser
                               20                   25                   30

Gly Asp Gln Lys Lys Phe Leu Ala Trp Tyr Gln Gln Lys Pro Gly Gln
                               35                   40                   45

Ser Pro Lys Leu Leu Ile Ser Leu Ala Ser Thr Arg Glu Ser Gly Val
                               50                   55                   60

Pro Asp Arg Phe Ile Gly Ser Gly Ser Gly Thr Asp Phe Thr Leu Thr
               65                   70                   75                   80

Ile Asn Asn Met Gln Ala Glu Asp Leu Ala Ile Tyr Tyr Cys Gln Gln
                               85                   90                   95

His Tyr Asp Ile Pro Tyr Thr Phe Gly Ala Gly Thr Lys Leu Glu Leu
                              100                  105                  110
```

<210> SEQ ID NO 15
<211> LENGTH: 116
<212> TYPE: PRT
<213> ORGANISM: Artificial Sequence
<220> FEATURE:
<223> OTHER INFORMATION: R8 VH

<400> SEQUENCE: 15

```
              Val Lys Val Val Glu Ser Gly Gly Gly Leu Val Gln Pro Gly Arg Ser
               1               5                    10                   15

Met Lys Leu Ser Cys Ala Ala Ser Gly Phe Thr Phe Ser Asp Tyr Phe
                               20                   25                   30

Met Ala Trp Val Arg Gln Ser Pro Lys Lys Gly Leu Glu Trp Val Ala
                               35                   40                   45

Ser Ile Asn Tyr Gly Gly Ser Arg Thr Tyr Tyr Glu Asp Ser Val Lys
                               50                   55                   60

Gly Arg Phe Thr Ile Ser Arg Asp Asn Ala Lys Ser Thr Leu Tyr Leu
               65                   70                   75                   80

Gln Met Asn Ser Leu Arg Ser Glu Asp Thr Ala Thr Tyr Tyr Cys Ala
                               85                   90                   95

Arg His Pro His Arg Leu Phe Asp Tyr Trp Gly Gln Gly Val Met Val
                              100                  105                  110

Thr Val Ser Ser
                      115
```

<210> SEQ ID NO 16
<211> LENGTH: 112
<212> TYPE: PRT
<213> ORGANISM: Artificial Sequence
<220> FEATURE:
<223> OTHER INFORMATION: R8 VL

<400> SEQUENCE: 16

```
              Asp Ile Val Met Thr Gln Ser Pro Ser Phe Leu Ala Val Ser Val Gly
               1               5                    10                   15

Glu Thr Val Thr Ile Asn Cys Lys Ser Ser Gln Ser Phe Leu Ser Ser
                               20                   25                   30

Gly Asn Gln Glu Asn Tyr Leu Ala Trp Tyr Gln Gln Lys Pro Gly Gln
                               35                   40                   45

Ser Pro Lys Leu Leu Ile His Leu Ala Ser Thr Arg Glu Ser Gly Val
                               50                   55                   60

Pro Asp Arg Phe Ile Gly Ser Gly Ser Gly Thr Asp Phe Thr Leu Thr
               65                   70                   75                   80
```

```
Ile Ser Ser Met Gln Ala Glu Asp Val Ala Ile Tyr Tyr Cys Gln Gln
                85                  90                  95

His Tyr Asp Ile Pro Tyr Thr Phe Gly Ala Gly Thr Lys Leu Glu Leu
            100                 105                 110
```

<210> SEQ ID NO 17
<211> LENGTH: 118
<212> TYPE: PRT
<213> ORGANISM: Artificial Sequence
<220> FEATURE:
<223> OTHER INFORMATION: R9 VH

<400> SEQUENCE: 17

```
Gln Val Thr Leu Lys Glu Ser Gly Pro Gly Ile Leu Gln Pro Ser His
1               5                   10                  15

Thr Leu Ser Leu Thr Cys Ser Phe Ser Gly Phe Ser Leu Asn Thr Tyr
            20                  25                  30

Gly Val Gly Val Asn Trp Ile Arg Gln Pro Ser Gly Lys Gly Leu Glu
        35                  40                  45

Trp Leu Ala Ser Ile Trp Trp His Gly Lys Thr Tyr Ile Asn Pro Ser
50                  55                  60

Leu Lys Asn Arg Leu Thr Val Ser Lys Asp Pro Ser Asn Asn Gln Ala
65                  70                  75                  80

Phe Leu Glu Val Thr Asn Val Asp Pro Ala Asp Thr Ala Thr Tyr Tyr
                85                  90                  95

Cys Ala His Ala Arg Ala Gln Leu Leu Asp Tyr Trp Gly Gln Gly Val
            100                 105                 110

Met Val Thr Val Ser Ser
            115
```

<210> SEQ ID NO 18
<211> LENGTH: 112
<212> TYPE: PRT
<213> ORGANISM: Artificial Sequence
<220> FEATURE:
<223> OTHER INFORMATION: R9 VL

<400> SEQUENCE: 18

```
Asp Ile Val Met Thr Gln Thr Pro Ser Ser Gln Ala Val Ser Ala Gly
1               5                   10                  15

Glu Lys Val Thr Met Ser Cys Lys Ser Ser Gln Ser Leu Leu Tyr Ser
            20                  25                  30

Gly Asp Gln Lys Asn Tyr Leu Ala Trp Tyr Gln Gln Lys Pro Gly Gln
        35                  40                  45

Ser Pro Lys Leu Leu Ile Tyr Leu Thr Ser Thr Arg Glu Ser Gly Val
50                  55                  60

Pro Asp Arg Phe Ile Gly Ser Gly Ser Gly Thr Asp Phe Thr Leu Thr
65                  70                  75                  80

Ile Ser Ser Val Gln Ala Glu Asp Leu Ala Asp Tyr Tyr Cys Gln Gln
                85                  90                  95

His Tyr Ser Tyr Pro Leu Thr Phe Gly Ser Gly Thr Lys Leu Glu Ile
            100                 105                 110
```

<210> SEQ ID NO 19
<211> LENGTH: 121
<212> TYPE: PRT
<213> ORGANISM: Artificial Sequence
<220> FEATURE:
<223> OTHER INFORMATION: R11 VH

<400> SEQUENCE: 19

Glu Val Gln Leu Val Glu Ser Gly Gly Leu Val Gln Pro Gly Arg
1               5                   10                  15

Ser Arg Lys Leu Ser Cys Ala Ala Ser Gly Phe Thr Phe Asn Asn Tyr
            20                  25                  30

Gly Met Ala Trp Val Arg Gln Ala Pro Thr Lys Gly Leu Glu Trp Val
        35                  40                  45

Ala Ser Ile Thr Asn Ser Gly Tyr Thr Thr Tyr Tyr Arg Asp Ser Val
    50                  55                  60

Lys Gly Arg Phe Thr Ile Ser Arg Asp Asn Ala Lys Asn Ala Leu Tyr
65                  70                  75                  80

Leu Gln Met Asp Ser Leu Arg Ser Glu Asp Thr Ala Thr Tyr Tyr Cys
                85                  90                  95

Thr Thr Gly Gly Tyr Gly Gly Tyr Phe Pro Leu Phe Asp Tyr Trp Gly
            100                 105                 110

His Gly Val Met Val Thr Val Ser Ser
        115                 120

<210> SEQ ID NO 20
<211> LENGTH: 111
<212> TYPE: PRT
<213> ORGANISM: Artificial Sequence
<220> FEATURE:
<223> OTHER INFORMATION: R11 VL

<400> SEQUENCE: 20

Asp Val Val Met Thr Gln Thr Pro Val Ser Leu Ser Val Ser Leu Gly
1               5                   10                  15

Gly Gln Thr Ser Ile Ser Cys Arg Ser Ser Gln Ser Leu Phe His Ser
            20                  25                  30

Asp Gly Asn Thr Tyr Leu Tyr Trp Tyr Leu Arg Lys Pro Gly Gln Ser
        35                  40                  45

Pro Gln Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Pro Glu Asp Leu Gly Leu Tyr Tyr Cys Tyr Gln Gly
                85                  90                  95

Thr His Tyr Pro Pro Thr Phe Gly Gly Thr Lys Leu Glu Ile
            100                 105                 110

<210> SEQ ID NO 21
<211> LENGTH: 123
<212> TYPE: PRT
<213> ORGANISM: Artificial Sequence
<220> FEATURE:
<223> OTHER INFORMATION: R14 VH

<400> SEQUENCE: 21

Gln Val Thr Leu Lys Glu Ser Gly Pro Gly Ile Leu Gln Pro Ser His
1               5                   10                  15

Thr Leu Ser Leu Thr Cys Ser Phe Ser Gly Phe Ser Leu Ser Thr Tyr
            20                  25                  30

Gly Met Gly Val Ser Trp Ile Arg Gln Pro Ser Gly Lys Gly Leu Glu
        35                  40                  45

Trp Leu Ala Ser Ile Trp Trp Asn Gly Arg Thr Tyr Thr Asn Pro Ser
    50                  55                  60

```
Leu Met Ser Arg Leu Thr Val Ser Lys Asp Thr Ser Thr Asn Gln Ala
 65                  70                  75                  80

Phe Leu Arg Val Thr Ser Val Glu Thr Ala Asp Thr Ala Thr Tyr Tyr
                 85                  90                  95

Cys Ala His Thr Pro Tyr Asp Tyr Ser Asn Leu Gly Trp Phe Thr Tyr
            100                 105                 110

Trp Gly Gln Gly Thr Leu Val Thr Val Ser Ser
        115                 120
```

<210> SEQ ID NO 22
<211> LENGTH: 112
<212> TYPE: PRT
<213> ORGANISM: Artificial Sequence
<220> FEATURE:
<223> OTHER INFORMATION: R14 VL

<400> SEQUENCE: 22

```
Asp Ile Leu Met Thr Gln Thr Pro Ser Ser Gln Ala Val Ser Ala Gly
 1               5                  10                  15

Glu Lys Val Thr Val Ser Cys Lys Ser Ser Gln Ser Leu Leu Tyr Ser
                 20                  25                  30

Gly Asp Gln Lys Ser Tyr Leu Ala Trp Tyr Gln Lys Pro Gly Gln
             35                  40                  45

Ser Pro Lys Leu Leu Ile Tyr Leu Ala Ser Thr Arg Lys Ser Gly Val
 50                  55                  60

Pro Asp Arg Phe Ile Gly Ser Gly Ser Gly Thr Asp Phe Thr Leu Thr
 65                  70                  75                  80

Ile Ser Ser Val Gln Ala Glu Asp Leu Ala Asp Tyr Tyr Cys Gln Gln
                 85                  90                  95

His Tyr Thr Tyr Pro Leu Thr Phe Gly Ser Gly Thr Lys Leu Glu Ile
            100                 105                 110
```

<210> SEQ ID NO 23
<211> LENGTH: 117
<212> TYPE: PRT
<213> ORGANISM: Artificial Sequence
<220> FEATURE:
<223> OTHER INFORMATION: R20 VH

<400> SEQUENCE: 23

```
Glu Val Gln Leu Val Glu Ser Gly Gly Gly Leu Val Gln Pro Gly Arg
 1               5                  10                  15

Ser Met Lys Leu Ser Cys Ala Val Ser Gly Phe Thr Phe Ser Asp Tyr
                 20                  25                  30

Tyr Met Ala Trp Val Arg Gln Ala Pro Lys Lys Gly Leu Glu Trp Val
             35                  40                  45

Ala Ser Ile Ser Tyr Glu Gly Arg Asn Thr Tyr Tyr Gly Asp Ser Val
 50                  55                  60

Lys Gly Arg Phe Thr Ile Ser Arg Asp Asn Ala Lys Asn Thr Leu Tyr
 65                  70                  75                  80

Leu Gln Met Asn Ser Leu Arg Ser Glu Asp Thr Ala Thr Tyr Tyr Cys
                 85                  90                  95

Ala Arg His Pro Arg Arg Tyr Phe Asp Phe Trp Gly Pro Gly Thr Met
            100                 105                 110

Val Thr Val Ser Ser
        115
```

<210> SEQ ID NO 24

```
<211> LENGTH: 112
<212> TYPE: PRT
<213> ORGANISM: Artificial Sequence
<220> FEATURE:
<223> OTHER INFORMATION: R20 VL

<400> SEQUENCE: 24

Asp Ile Val Met Thr Gln Ser Pro Ser Ser Leu Ala Val Ser Ala Gly
1               5                   10                  15

Glu Thr Val Thr Ile Asn Cys Lys Ser Gln Ser Leu Leu Phe Ser
            20                  25                  30

Gly Asp Gln Glu Asn His Leu Ala Trp Tyr Gln Gln Lys Ala Gly Gln
        35                  40                  45

Ser Ala Lys Leu Leu Ile Tyr Trp Ala Ser Thr Arg Glu Ser Gly Val
    50                  55                  60

Pro Asp Arg Phe Ile Gly Ser Gly Ser Gly Ala Asp Phe Thr Leu Thr
65                  70                  75                  80

Ile Ser Ser Met Gln Ala Glu Asp Arg Ala Thr Tyr Tyr Cys Gln Gln
                85                  90                  95

Asn Tyr Asp Ile Pro Tyr Thr Phe Gly Ala Gly Thr Lys Leu Glu Leu
            100                 105                 110

<210> SEQ ID NO 25
<211> LENGTH: 117
<212> TYPE: PRT
<213> ORGANISM: Artificial Sequence
<220> FEATURE:
<223> OTHER INFORMATION: R28 VH

<400> SEQUENCE: 25

Glu Val Gln Leu Val Glu Ser Gly Gly Gly Leu Val Gln Pro Gly Arg
1               5                   10                  15

Ser Leu Lys Leu Ser Cys Ala Ala Ser Gly Phe Thr Phe Ser Asp Tyr
            20                  25                  30

Phe Met Ala Trp Val Arg Gln Ala Pro Lys Lys Gly Leu Glu Trp Val
        35                  40                  45

Ala Ser Ile Asn Tyr Glu Gly Ser Arg Thr Tyr Tyr Gly Asp Ser Val
    50                  55                  60

Lys Asp Arg Phe Thr Ile Ser Arg Asp Asn Thr Lys Thr Thr Leu Tyr
65                  70                  75                  80

Leu Gln Met Thr Ser Leu Arg Ser Glu Asp Thr Ala Thr Tyr Tyr Cys
                85                  90                  95

Ala Arg His Pro Arg Arg Tyr Phe Asp Phe Trp Gly Gln Gly Val Met
            100                 105                 110

Val Thr Val Ser Ser
        115

<210> SEQ ID NO 26
<211> LENGTH: 112
<212> TYPE: PRT
<213> ORGANISM: Artificial Sequence
<220> FEATURE:
<223> OTHER INFORMATION: R28 VL

<400> SEQUENCE: 26

Asp Ile Val Met Thr Gln Ser Pro Ser Ser Leu Ala Val Ser Ala Gly
1               5                   10                  15

Glu Thr Val Thr Ile Asn Cys Lys Ser Ser Arg Ser Leu Phe Ser Ser
            20                  25                  30
```

Gly Tyr Gln Glu Asn Tyr Leu Ala Trp Tyr Gln Gln Lys Pro Gly Gln
                35                  40                  45

Ser Pro Lys Met Leu Ile Tyr Leu Ala Ser Thr Arg Glu Ser Gly Val
 50                  55                  60

Pro Asp Arg Phe Ile Gly Ser Gly Ser Gly Thr Asp Phe Thr Leu Thr
 65                  70                  75                  80

Ile Asn Thr Leu Gln Ala Glu Asp Leu Ala Ile Tyr Tyr Cys Gln Gln
                 85                  90                  95

His Tyr Asp Ile Pro Tyr Thr Phe Gly Ala Gly Thr Lys Leu Glu Leu
                100                 105                 110

<210> SEQ ID NO 27
<211> LENGTH: 218
<212> TYPE: PRT
<213> ORGANISM: Artificial Sequence
<220> FEATURE:
<223> OTHER INFORMATION: hCLDN-5

<400> SEQUENCE: 27

Met Gly Ser Ala Ala Leu Glu Ile Leu Gly Leu Val Leu Cys Leu Val
 1               5                  10                  15

Gly Trp Gly Gly Leu Ile Leu Ala Cys Gly Leu Pro Met Trp Gln Val
                20                  25                  30

Thr Ala Phe Leu Asp His Asn Ile Val Thr Ala Gln Thr Thr Trp Lys
                35                  40                  45

Gly Leu Trp Met Ser Cys Val Val Gln Ser Thr Gly His Met Gln Cys
 50                  55                  60

Lys Val Tyr Asp Ser Val Leu Ala Leu Ser Thr Glu Val Gln Ala Ala
 65                  70                  75                  80

Arg Ala Leu Thr Val Ser Ala Val Leu Leu Ala Phe Val Ala Leu Phe
                 85                  90                  95

Val Thr Leu Ala Gly Ala Gln Cys Thr Thr Cys Val Ala Pro Gly Pro
                100                 105                 110

Ala Lys Ala Arg Val Ala Leu Thr Gly Gly Val Leu Tyr Leu Phe Cys
                115                 120                 125

Gly Leu Leu Ala Leu Val Pro Leu Cys Trp Phe Ala Asn Ile Val Val
130                 135                 140

Arg Glu Phe Tyr Asp Pro Ser Val Pro Val Ser Gln Lys Tyr Glu Leu
145                 150                 155                 160

Gly Ala Ala Leu Tyr Ile Gly Trp Ala Ala Thr Ala Leu Leu Met Val
                165                 170                 175

Gly Gly Cys Leu Leu Cys Cys Gly Ala Trp Val Cys Thr Gly Arg Pro
                180                 185                 190

Asp Leu Ser Phe Pro Val Lys Tyr Ser Ala Pro Arg Arg Pro Thr Ala
                195                 200                 205

Thr Gly Asp Tyr Asp Lys Lys Asn Tyr Val
210                 215

<210> SEQ ID NO 28
<211> LENGTH: 218
<212> TYPE: PRT
<213> ORGANISM: Artificial Sequence
<220> FEATURE:
<223> OTHER INFORMATION: cCLDN-5

<400> SEQUENCE: 28

Met Gly Ser Ala Ala Leu Glu Ile Leu Gly Leu Val Leu Cys Leu Val
 1               5                  10                  15

Gly Trp Gly Gly Leu Ile Leu Ala Cys Gly Leu Pro Met Trp Gln Val
            20                  25                  30

Thr Ala Phe Leu Asp His Asn Ile Val Thr Ala Gln Thr Thr Trp Lys
            35                  40                  45

Gly Leu Trp Met Ser Cys Val Val Gln Ser Thr Gly His Met Gln Cys
 50                  55                  60

Lys Val Tyr Asp Ser Val Leu Ala Leu Ser Thr Glu Val Gln Ala Ala
 65                  70                  75                  80

Arg Ala Leu Thr Val Gly Ala Val Leu Leu Ala Phe Val Ala Leu Phe
                85                  90                  95

Val Thr Leu Ala Gly Ala Gln Cys Thr Thr Cys Val Ala Pro Gly Pro
            100                 105                 110

Ala Lys Ala Arg Val Ala Leu Thr Gly Gly Val Leu Tyr Leu Leu Cys
            115                 120                 125

Gly Leu Leu Ala Leu Val Pro Leu Cys Trp Phe Ala Asn Ile Val Val
 130                 135                 140

Arg Glu Phe Tyr Asp Pro Ser Val Pro Val Ser Gln Lys Tyr Glu Leu
145                 150                 155                 160

Gly Ala Ala Leu Tyr Ile Gly Trp Ala Ala Thr Ala Leu Leu Met Val
                165                 170                 175

Gly Gly Gly Leu Leu Cys Cys Gly Ala Trp Val Cys Thr Ser Arg Pro
            180                 185                 190

Asp Leu Ser Phe Pro Val Lys Tyr Ser Ala Pro Arg Arg Pro Thr Ala
            195                 200                 205

Thr Gly Asp Tyr Asp Lys Lys Asn Tyr Val
            210                 215

<210> SEQ ID NO 29
<211> LENGTH: 218
<212> TYPE: PRT
<213> ORGANISM: Artificial Sequence
<220> FEATURE:
<223> OTHER INFORMATION: mCLDN-5

<400> SEQUENCE: 29

Met Gly Ser Ala Ala Leu Glu Ile Leu Gly Leu Val Leu Cys Leu Val
1               5                   10                  15

Gly Trp Val Gly Leu Ile Leu Ala Cys Gly Leu Pro Met Trp Gln Val
            20                  25                  30

Thr Ala Phe Leu Asp His Asn Ile Val Thr Ala Gln Thr Thr Trp Lys
            35                  40                  45

Gly Leu Trp Met Ser Cys Val Val Gln Ser Thr Gly His Met Gln Cys
 50                  55                  60

Lys Val Tyr Glu Ser Val Leu Ala Leu Ser Glu Val Gln Ala Ala
 65                  70                  75                  80

Arg Ala Leu Thr Val Gly Ala Val Leu Leu Ala Leu Val Ala Leu Phe
                85                  90                  95

Val Thr Leu Thr Gly Ala Gln Cys Thr Thr Cys Val Ala Pro Gly Pro
            100                 105                 110

Val Lys Ala Arg Val Ala Leu Thr Gly Gly Ala Leu Tyr Ala Val Cys
            115                 120                 125

Gly Leu Leu Ala Leu Val Pro Leu Cys Trp Phe Ala Asn Ile Val Val
 130                 135                 140

Arg Glu Phe Tyr Asp Pro Thr Val Pro Val Ser Gln Lys Tyr Glu Leu
145                 150                 155                 160

Gly Ala Ala Leu Tyr Ile Gly Trp Ala Ala Ser Ala Leu Leu Met Cys
                165                 170                 175

Gly Gly Gly Leu Val Cys Cys Gly Ala Trp Val Cys Thr Gly Arg Pro
                180                 185                 190

Glu Phe Ser Phe Pro Val Lys Tyr Ser Ala Pro Arg Arg Pro Thr Ala
                195                 200                 205

Asn Gly Asp Tyr Asp Lys Lys Asn Tyr Val
        210                 215

<210> SEQ ID NO 30
<211> LENGTH: 211
<212> TYPE: PRT
<213> ORGANISM: Artificial Sequence
<220> FEATURE:
<223> OTHER INFORMATION: hCLDN-1

<400> SEQUENCE: 30

Met Ala Asn Ala Gly Leu Gln Leu Leu Gly Phe Ile Leu Ala Phe Leu
1               5                   10                  15

Gly Trp Ile Gly Ala Ile Val Ser Thr Ala Leu Pro Gln Trp Arg Ile
                20                  25                  30

Tyr Ser Tyr Ala Gly Asp Asn Ile Val Thr Ala Gln Ala Met Tyr Glu
            35                  40                  45

Gly Leu Trp Met Ser Cys Val Ser Gln Ser Thr Gly Gln Ile Gln Cys
        50                  55                  60

Lys Val Phe Asp Ser Leu Leu Asn Leu Ser Ser Thr Leu Gln Ala Thr
65                  70                  75                  80

Arg Ala Leu Met Val Val Gly Ile Leu Leu Gly Val Ile Ala Ile Phe
                85                  90                  95

Val Ala Thr Val Gly Met Lys Cys Met Lys Cys Leu Glu Asp Asp Glu
                100                 105                 110

Val Gln Lys Met Arg Met Ala Val Ile Gly Gly Ala Ile Phe Leu Leu
                115                 120                 125

Ala Gly Leu Ala Ile Leu Val Ala Thr Ala Trp Tyr Gly Asn Arg Ile
        130                 135                 140

Val Gln Glu Phe Tyr Asp Pro Met Thr Pro Val Asn Ala Arg Tyr Glu
145                 150                 155                 160

Phe Gly Gln Ala Leu Phe Thr Gly Trp Ala Ala Ala Ser Leu Cys Leu
                165                 170                 175

Leu Gly Gly Ala Leu Leu Cys Cys Ser Cys Pro Arg Lys Thr Thr Ser
                180                 185                 190

Tyr Pro Thr Pro Arg Pro Tyr Pro Lys Pro Ala Pro Ser Ser Gly Lys
                195                 200                 205

Asp Tyr Val
        210

<210> SEQ ID NO 31
<211> LENGTH: 230
<212> TYPE: PRT
<213> ORGANISM: Artificial Sequence
<220> FEATURE:
<223> OTHER INFORMATION: hCLDN-2

<400> SEQUENCE: 31

Met Ala Ser Leu Gly Leu Gln Leu Val Gly Tyr Ile Leu Gly Leu Leu
1               5                   10                  15

Gly Leu Leu Gly Thr Leu Val Ala Met Leu Leu Pro Ser Trp Lys Thr

```
            20                  25                  30
Ser Ser Tyr Val Gly Ala Ser Ile Val Thr Ala Val Gly Phe Ser Lys
        35                  40                  45

Gly Leu Trp Met Glu Cys Ala Thr His Ser Thr Gly Ile Thr Gln Cys
    50                  55                  60

Asp Ile Tyr Ser Thr Leu Leu Gly Leu Pro Ala Asp Ile Gln Ala Ala
65                  70                  75                  80

Gln Ala Met Met Val Thr Ser Ser Ala Ile Ser Ser Leu Ala Cys Ile
                85                  90                  95

Ile Ser Val Val Gly Met Arg Cys Thr Val Phe Cys Gln Glu Ser Arg
            100                 105                 110

Ala Lys Asp Arg Val Ala Val Ala Gly Gly Val Phe Phe Ile Leu Gly
        115                 120                 125

Gly Leu Leu Gly Phe Ile Pro Val Ala Trp Asn Leu His Gly Ile Leu
    130                 135                 140

Arg Asp Phe Tyr Ser Pro Leu Val Pro Asp Ser Met Lys Phe Glu Ile
145                 150                 155                 160

Gly Glu Ala Leu Tyr Leu Gly Ile Ile Ser Ser Leu Phe Ser Leu Ile
                165                 170                 175

Ala Gly Ile Ile Leu Cys Phe Ser Cys Ser Ser Gln Arg Asn Arg Ser
            180                 185                 190

Asn Tyr Tyr Asp Ala Tyr Gln Ala Gln Pro Leu Ala Thr Arg Ser Ser
        195                 200                 205

Pro Arg Pro Gly Gln Pro Pro Lys Val Lys Ser Glu Phe Asn Ser Tyr
    210                 215                 220

Ser Leu Thr Gly Tyr Val
225                 230

<210> SEQ ID NO 32
<211> LENGTH: 220
<212> TYPE: PRT
<213> ORGANISM: Artificial Sequence
<220> FEATURE:
<223> OTHER INFORMATION: hCLDN-3

<400> SEQUENCE: 32

Met Ser Met Gly Leu Glu Ile Thr Gly Thr Ala Leu Ala Val Leu Gly
1               5                   10                  15

Trp Leu Gly Thr Ile Val Cys Cys Ala Leu Pro Met Trp Arg Val Ser
            20                  25                  30

Ala Phe Ile Gly Ser Asn Ile Ile Thr Ser Gln Asn Ile Trp Glu Gly
        35                  40                  45

Leu Trp Met Asn Cys Val Val Gln Ser Thr Gly Gln Met Gln Cys Lys
    50                  55                  60

Val Tyr Asp Ser Leu Leu Ala Leu Pro Gln Asp Leu Gln Ala Ala Arg
65                  70                  75                  80

Ala Leu Ile Val Val Ala Ile Leu Leu Ala Ala Phe Gly Leu Leu Val
                85                  90                  95

Ala Leu Val Gly Ala Gln Cys Thr Asn Cys Val Gln Asp Asp Thr Ala
            100                 105                 110

Lys Ala Lys Ile Thr Ile Val Ala Gly Val Leu Phe Leu Leu Ala Ala
        115                 120                 125

Leu Leu Thr Leu Val Pro Val Ser Trp Ser Ala Asn Thr Ile Ile Arg
    130                 135                 140

Asp Phe Tyr Asn Pro Val Val Pro Glu Ala Gln Lys Arg Glu Met Gly
```

```
                145                 150                 155                 160
Ala Gly Leu Tyr Val Gly Trp Ala Ala Ala Leu Gln Leu Leu Gly
                    165                 170                 175

Gly Ala Leu Leu Cys Cys Ser Cys Pro Pro Arg Glu Lys Lys Tyr Thr
                180                 185                 190

Ala Thr Lys Val Val Tyr Ser Ala Pro Arg Ser Thr Gly Pro Gly Ala
                195                 200                 205

Ser Leu Gly Thr Gly Tyr Asp Arg Lys Asp Tyr Val
                210                 215                 220

<210> SEQ ID NO 33
<211> LENGTH: 209
<212> TYPE: PRT
<213> ORGANISM: Artificial Sequence
<220> FEATURE:
<223> OTHER INFORMATION: hCLDN-4

<400> SEQUENCE: 33

Met Ala Ser Met Gly Leu Gln Val Met Gly Ile Ala Leu Ala Val Leu
1               5                   10                  15

Gly Trp Leu Ala Val Met Leu Cys Cys Ala Leu Pro Met Trp Arg Val
                20                  25                  30

Thr Ala Phe Ile Gly Ser Asn Ile Val Thr Ser Gln Thr Ile Trp Glu
            35                  40                  45

Gly Leu Trp Met Asn Cys Val Val Gln Ser Thr Gly Gln Met Gln Cys
        50                  55                  60

Lys Val Tyr Asp Ser Leu Leu Ala Leu Pro Gln Asp Leu Gln Ala Ala
65                  70                  75                  80

Arg Ala Leu Val Ile Ile Ser Ile Ile Val Ala Ala Leu Gly Val Leu
                85                  90                  95

Leu Ser Val Val Gly Gly Lys Cys Thr Asn Cys Leu Glu Asp Glu Ser
                100                 105                 110

Ala Lys Ala Lys Thr Met Ile Val Ala Gly Val Val Phe Leu Leu Ala
                115                 120                 125

Gly Leu Met Val Ile Val Pro Val Ser Trp Thr Ala His Asn Ile Ile
        130                 135                 140

Gln Asp Phe Tyr Asn Pro Leu Val Ala Ser Gly Gln Lys Arg Glu Met
145                 150                 155                 160

Gly Ala Ser Leu Tyr Val Gly Trp Ala Ala Ser Gly Leu Leu Leu Leu
                    165                 170                 175

Gly Gly Gly Leu Leu Cys Cys Asn Cys Pro Pro Arg Thr Asp Lys Pro
                180                 185                 190

Tyr Ser Ala Lys Tyr Ser Ala Ala Arg Ser Ala Ala Ala Ser Asn Tyr
                195                 200                 205

Val

<210> SEQ ID NO 34
<211> LENGTH: 220
<212> TYPE: PRT
<213> ORGANISM: Artificial Sequence
<220> FEATURE:
<223> OTHER INFORMATION: hCLDN-6

<400> SEQUENCE: 34

Met Ala Ser Ala Gly Met Gln Ile Leu Gly Val Val Leu Thr Leu Leu
1               5                   10                  15

Gly Trp Val Asn Gly Leu Val Ser Cys Ala Leu Pro Met Trp Lys Val
```

```
                     20                  25                  30
Thr Ala Phe Ile Gly Asn Ser Ile Val Ala Gln Val Val Trp Glu
            35                  40                  45
Gly Leu Trp Met Ser Cys Val Val Gln Ser Thr Gly Gln Met Gln Cys
        50                  55                  60
Lys Val Tyr Asp Ser Leu Ala Leu Pro Gln Asp Leu Gln Ala Ala
 65                  70                  75                  80
Arg Ala Leu Cys Val Ile Ala Leu Leu Val Ala Leu Phe Gly Leu Leu
                85                  90                  95
Val Tyr Leu Ala Gly Ala Lys Cys Thr Thr Cys Val Glu Glu Lys Asp
            100                 105                 110
Ser Lys Ala Arg Leu Val Leu Thr Ser Gly Ile Val Phe Val Ile Ser
            115                 120                 125
Gly Val Leu Thr Leu Ile Pro Val Cys Trp Thr Ala His Ala Ile Ile
            130                 135                 140
Arg Asp Phe Tyr Asn Pro Leu Val Ala Glu Ala Gln Lys Arg Glu Leu
145                 150                 155                 160
Gly Ala Ser Leu Tyr Leu Gly Trp Ala Ala Ser Gly Leu Leu Leu Leu
                165                 170                 175
Gly Gly Gly Leu Leu Cys Cys Thr Cys Pro Ser Gly Gly Ser Gln Gly
            180                 185                 190
Pro Ser His Tyr Met Ala Arg Tyr Ser Thr Ser Ala Pro Ala Ile Ser
            195                 200                 205
Arg Gly Pro Ser Glu Tyr Pro Thr Lys Asn Tyr Val
            210                 215                 220

<210> SEQ ID NO 35
<211> LENGTH: 211
<212> TYPE: PRT
<213> ORGANISM: Artificial Sequence
<220> FEATURE:
<223> OTHER INFORMATION: hCLDN-7

<400> SEQUENCE: 35

Met Ala Asn Ser Gly Leu Gln Leu Leu Gly Phe Ser Met Ala Leu Leu
 1               5                  10                  15
Gly Trp Val Gly Leu Val Ala Cys Thr Ala Ile Pro Gln Trp Gln Met
            20                  25                  30
Ser Ser Tyr Ala Gly Asp Asn Ile Ile Thr Ala Gln Ala Met Tyr Lys
        35                  40                  45
Gly Leu Trp Met Asp Cys Val Thr Gln Ser Thr Gly Met Met Ser Cys
    50                  55                  60
Lys Met Tyr Asp Ser Val Leu Ala Leu Ser Ala Ala Leu Gln Ala Thr
65                  70                  75                  80
Arg Ala Leu Met Val Val Ser Leu Val Leu Gly Phe Leu Ala Met Phe
                85                  90                  95
Val Ala Thr Met Gly Met Lys Cys Thr Arg Cys Gly Gly Asp Asp Lys
            100                 105                 110
Val Lys Lys Ala Arg Ile Ala Met Gly Gly Gly Ile Ile Phe Ile Val
            115                 120                 125
Ala Gly Leu Ala Ala Leu Val Ala Cys Ser Trp Tyr Gly His Gln Ile
            130                 135                 140
Val Thr Asp Phe Tyr Asn Pro Leu Ile Pro Thr Asn Ile Lys Tyr Glu
145                 150                 155                 160
Phe Gly Pro Ala Ile Phe Ile Gly Trp Ala Gly Ser Ala Leu Val Ile
```

165                 170                 175
Leu Gly Gly Ala Leu Leu Ser Cys Ser Cys Pro Gly Asn Glu Ser Lys
                180                 185                 190

Ala Gly Tyr Arg Val Pro Arg Ser Tyr Pro Lys Ser Asn Ser Ser Lys
            195                 200                 205

Glu Tyr Val
    210

<210> SEQ ID NO 36
<211> LENGTH: 217
<212> TYPE: PRT
<213> ORGANISM: Artificial Sequence
<220> FEATURE:
<223> OTHER INFORMATION: hCLDN-9

<400> SEQUENCE: 36

Met Ala Ser Thr Gly Leu Glu Leu Leu Gly Met Thr Leu Ala Val Leu
1               5                   10                  15

Gly Trp Leu Gly Thr Leu Val Ser Cys Ala Leu Pro Leu Trp Lys Val
            20                  25                  30

Thr Ala Phe Ile Gly Asn Ser Ile Val Val Ala Gln Val Val Trp Glu
        35                  40                  45

Gly Leu Trp Met Ser Cys Val Val Gln Ser Thr Gly Gln Met Gln Cys
    50                  55                  60

Lys Val Tyr Asp Ser Leu Leu Ala Leu Pro Gln Asp Leu Gln Ala Ala
65                  70                  75                  80

Arg Ala Leu Cys Val Ile Ala Leu Leu Ala Leu Leu Gly Leu Leu
                85                  90                  95

Val Ala Ile Thr Gly Ala Gln Cys Thr Thr Cys Val Glu Asp Glu Gly
            100                 105                 110

Ala Lys Ala Arg Ile Val Leu Thr Ala Gly Val Ile Leu Leu Leu Ala
        115                 120                 125

Gly Ile Leu Val Leu Ile Pro Val Cys Trp Thr Ala His Ala Ile Ile
    130                 135                 140

Gln Asp Phe Tyr Asn Pro Leu Val Ala Glu Ala Leu Lys Arg Glu Leu
145                 150                 155                 160

Gly Ala Ser Leu Tyr Leu Gly Trp Ala Ala Ala Leu Leu Met Leu
                165                 170                 175

Gly Gly Gly Leu Leu Cys Cys Thr Cys Pro Pro Pro Gln Val Glu Arg
            180                 185                 190

Pro Arg Gly Pro Arg Leu Gly Tyr Ser Ile Pro Ser Arg Ser Gly Ala
        195                 200                 205

Ser Gly Leu Asp Lys Arg Asp Tyr Val
    210                 215

<210> SEQ ID NO 37
<211> LENGTH: 211
<212> TYPE: PRT
<213> ORGANISM: Artificial Sequence
<220> FEATURE:
<223> OTHER INFORMATION: mCLDN-1

<400> SEQUENCE: 37

Met Ala Asn Ala Gly Leu Gln Leu Leu Gly Phe Ile Leu Ala Ser Leu
1               5                   10                  15

Gly Trp Ile Gly Ser Ile Val Ser Thr Ala Leu Pro Gln Trp Lys Ile
            20                  25                  30

Tyr Ser Tyr Ala Gly Asp Asn Ile Val Thr Ala Gln Ala Ile Tyr Glu
        35                  40                  45

Gly Leu Trp Met Ser Cys Val Ser Gln Ser Thr Gly Gln Ile Gln Cys
 50                  55                  60

Lys Val Phe Asp Ser Leu Leu Asn Leu Asn Ser Thr Leu Gln Ala Thr
 65                  70                  75                  80

Arg Ala Leu Met Val Ile Gly Ile Leu Leu Gly Leu Ile Ala Ile Phe
                 85                  90                  95

Val Ser Thr Ile Gly Met Lys Cys Met Arg Cys Leu Glu Asp Asp Glu
                100                 105                 110

Val Gln Lys Met Trp Met Ala Val Ile Gly Gly Ile Ile Phe Leu Ile
                115                 120                 125

Ser Gly Leu Ala Thr Leu Val Ala Thr Ala Trp Tyr Gly Asn Arg Ile
130                 135                 140

Val Gln Glu Phe Tyr Asp Pro Leu Thr Pro Ile Asn Ala Arg Tyr Glu
145                 150                 155                 160

Phe Gly Gln Ala Leu Phe Thr Gly Trp Ala Ala Ala Ser Leu Cys Leu
                165                 170                 175

Leu Gly Gly Val Leu Leu Ser Cys Ser Cys Pro Arg Lys Thr Thr Ser
                180                 185                 190

Tyr Pro Thr Pro Arg Pro Tyr Pro Lys Pro Thr Pro Ser Ser Gly Lys
                195                 200                 205

Asp Tyr Val
        210

<210> SEQ ID NO 38
<211> LENGTH: 230
<212> TYPE: PRT
<213> ORGANISM: Artificial Sequence
<220> FEATURE:
<223> OTHER INFORMATION: mCLDN-2

<400> SEQUENCE: 38

Met Ala Ser Leu Gly Val Gln Leu Val Gly Tyr Ile Leu Gly Leu Leu
 1               5                  10                  15

Gly Leu Leu Gly Thr Ser Ile Ala Met Leu Leu Pro Asn Trp Arg Thr
                20                  25                  30

Ser Ser Tyr Val Gly Ala Ser Ile Val Thr Ala Val Gly Phe Ser Lys
        35                  40                  45

Gly Leu Trp Met Glu Cys Ala Thr His Ser Thr Gly Ile Thr Gln Cys
 50                  55                  60

Asp Ile Tyr Ser Thr Leu Leu Gly Leu Pro Ala Asp Ile Gln Ala Ala
 65                  70                  75                  80

Gln Ala Met Met Val Thr Ser Ser Ala Met Ser Ser Leu Ala Cys Ile
                 85                  90                  95

Ile Ser Val Val Gly Met Arg Cys Thr Val Phe Cys Gln Asp Ser Arg
                100                 105                 110

Ala Lys Asp Arg Val Ala Val Gly Gly Val Phe Phe Ile Leu Gly Gly
                115                 120                 125

Gly Ile Leu Gly Phe Ile Pro Val Ala Trp Asn Leu His Gly Ile Leu
130                 135                 140

Arg Asp Phe Tyr Ser Pro Leu Val Pro Asp Ser Met Lys Phe Glu Ile
145                 150                 155                 160

Gly Glu Ala Leu Tyr Leu Gly Ile Ile Ser Ala Leu Phe Ser Leu Val
                165                 170                 175

```
Ala Gly Val Ile Leu Cys Phe Ser Cys Ser Pro Gln Gly Asn Arg Thr
            180                 185                 190

Asn Tyr Tyr Asp Gly Tyr Gln Ala Gln Pro Leu Ala Thr Arg Ser Ser
        195                 200                 205

Pro Arg Ser Ala Gln Gln Pro Lys Ala Lys Ser Glu Phe Asn Ser Tyr
    210                 215                 220

Ser Leu Thr Gly Tyr Val
225                 230
```

<210> SEQ ID NO 39
<211> LENGTH: 219
<212> TYPE: PRT
<213> ORGANISM: Artificial Sequence
<220> FEATURE:
<223> OTHER INFORMATION: mCLDN-3

<400> SEQUENCE: 39

```
Met Ser Met Gly Leu Glu Ile Thr Gly Thr Ser Leu Ala Val Leu Gly
1               5                   10                  15

Trp Leu Cys Thr Ile Val Cys Cys Ala Leu Pro Met Trp Arg Val Ser
            20                  25                  30

Ala Phe Ile Gly Ser Ser Ile Ile Thr Ala Gln Ile Thr Trp Glu Gly
        35                  40                  45

Leu Trp Met Asn Cys Val Val Gln Ser Thr Gly Gln Met Gln Cys Lys
    50                  55                  60

Met Tyr Asp Ser Leu Leu Ala Leu Pro Gln Asp Leu Gln Ala Ala Arg
65                  70                  75                  80

Ala Leu Ile Val Val Ser Ile Leu Leu Ala Ala Phe Gly Leu Leu Val
                85                  90                  95

Ala Leu Val Gly Ala Gln Cys Thr Asn Cys Val Gln Asp Glu Thr Ala
            100                 105                 110

Lys Ala Lys Ile Thr Ile Val Ala Gly Val Leu Phe Leu Leu Ala Ala
        115                 120                 125

Leu Leu Thr Leu Val Pro Val Ser Trp Ser Ala Asn Thr Ile Ile Arg
    130                 135                 140

Asp Phe Tyr Asn Pro Leu Val Pro Glu Ala Gln Lys Arg Glu Met Gly
145                 150                 155                 160

Ala Gly Leu Tyr Val Gly Trp Ala Ala Ala Leu Gln Leu Leu Gly Gly
                165                 170                 175

Gly Ala Leu Leu Cys Cys Ser Cys Pro Pro Arg Asp Lys Tyr Ala Pro
            180                 185                 190

Thr Lys Ile Leu Tyr Ser Ala Pro Arg Ser Thr Gly Pro Gly Thr Gly
        195                 200                 205

Thr Gly Thr Ala Tyr Asp Arg Lys Asp Tyr Val
    210                 215
```

<210> SEQ ID NO 40
<211> LENGTH: 210
<212> TYPE: PRT
<213> ORGANISM: Artificial Sequence
<220> FEATURE:
<223> OTHER INFORMATION: mCLDN-4

<400> SEQUENCE: 40

```
Met Ala Ser Met Gly Leu Gln Val Leu Gly Ile Ser Leu Ala Val Leu
1               5                   10                  15

Gly Trp Leu Gly Ile Ile Leu Ser Cys Ala Leu Pro Met Trp Arg Val
            20                  25                  30
```

Thr Ala Phe Ile Gly Ser Asn Ile Val Thr Ala Gln Thr Ser Trp Glu
            35                  40                  45

Gly Leu Trp Met Asn Cys Val Val Gln Ser Thr Gly Gln Met Gln Cys
 50                  55                  60

Lys Met Tyr Asp Ser Met Leu Ala Leu Pro Gln Asp Leu Gln Ala Ala
 65                  70                  75                  80

Arg Ala Leu Met Val Ile Ser Ile Val Gly Ala Leu Gly Met Leu
                 85                  90                  95

Leu Ser Val Val Gly Gly Lys Cys Thr Asn Cys Met Glu Asp Glu Thr
                100                 105                 110

Val Lys Ala Lys Ile Met Ile Thr Ala Gly Ala Val Phe Ile Val Ala
                115                 120                 125

Ser Met Leu Ile Met Val Pro Val Ser Trp Thr Ala His Asn Val Ile
            130                 135                 140

Arg Asp Phe Tyr Asn Pro Met Val Ala Ser Gly Gln Lys Arg Glu Met
145                 150                 155                 160

Gly Ala Ser Leu Tyr Val Gly Trp Ala Ala Ser Gly Leu Leu Leu Leu
                165                 170                 175

Gly Gly Gly Leu Leu Cys Cys Ser Cys Pro Pro Arg Ser Asn Asp Lys
            180                 185                 190

Pro Tyr Ser Ala Lys Tyr Ser Ala Ala Arg Ser Val Pro Ala Ser Asn
            195                 200                 205

Tyr Val
    210

<210> SEQ ID NO 41
<211> LENGTH: 218
<212> TYPE: PRT
<213> ORGANISM: Artificial Sequence
<220> FEATURE:
<223> OTHER INFORMATION: D68E

<400> SEQUENCE: 41

Met Gly Ser Ala Ala Leu Glu Ile Leu Gly Leu Val Leu Cys Leu Val
 1               5                  10                  15

Gly Trp Gly Gly Leu Ile Leu Ala Cys Gly Leu Pro Met Trp Gln Val
                20                  25                  30

Thr Ala Phe Leu Asp His Asn Ile Val Thr Ala Gln Thr Thr Trp Lys
            35                  40                  45

Gly Leu Trp Met Ser Cys Val Val Gln Ser Thr Gly His Met Gln Cys
 50                  55                  60

Lys Val Tyr Glu Ser Val Leu Ala Leu Ser Thr Glu Val Gln Ala Ala
 65                  70                  75                  80

Arg Ala Leu Thr Val Ser Ala Val Leu Leu Ala Phe Val Ala Leu Phe
                 85                  90                  95

Val Thr Leu Ala Gly Ala Gln Cys Thr Thr Cys Val Ala Pro Gly Pro
                100                 105                 110

Ala Lys Ala Arg Val Ala Leu Thr Gly Gly Val Leu Tyr Leu Phe Cys
            115                 120                 125

Gly Leu Leu Ala Leu Val Pro Leu Cys Trp Phe Ala Asn Ile Val Val
            130                 135                 140

Arg Glu Phe Tyr Asp Pro Ser Val Pro Val Ser Gln Lys Tyr Glu Leu
145                 150                 155                 160

Gly Ala Ala Leu Tyr Ile Gly Trp Ala Ala Thr Ala Leu Leu Met Val
                165                 170                 175

```
Gly Gly Cys Leu Leu Cys Cys Gly Ala Trp Val Cys Thr Gly Arg Pro
            180                 185                 190

Asp Leu Ser Phe Pro Val Lys Tyr Ser Ala Pro Arg Pro Thr Ala
        195                 200                 205

Thr Gly Asp Tyr Asp Lys Lys Asn Tyr Val
        210                 215

<210> SEQ ID NO 42
<211> LENGTH: 218
<212> TYPE: PRT
<213> ORGANISM: Artificial Sequence
<220> FEATURE:
<223> OTHER INFORMATION: T75A

<400> SEQUENCE: 42

Met Gly Ser Ala Ala Leu Glu Ile Leu Gly Leu Val Leu Cys Leu Val
1               5                   10                  15

Gly Trp Gly Gly Leu Ile Leu Ala Cys Gly Leu Pro Met Trp Gln Val
            20                  25                  30

Thr Ala Phe Leu Asp His Asn Ile Val Thr Ala Gln Thr Thr Trp Lys
        35                  40                  45

Gly Leu Trp Met Ser Cys Val Val Gln Ser Thr Gly His Met Gln Cys
    50                  55                  60

Lys Val Tyr Asp Ser Val Leu Ala Leu Ser Ala Glu Val Gln Ala Ala
65                  70                  75                  80

Arg Ala Leu Thr Val Ser Ala Val Leu Leu Ala Phe Val Ala Leu Phe
                85                  90                  95

Val Thr Leu Ala Gly Ala Gln Cys Thr Thr Cys Val Ala Pro Gly Pro
            100                 105                 110

Ala Lys Ala Arg Val Ala Leu Thr Gly Gly Val Leu Tyr Leu Phe Cys
        115                 120                 125

Gly Leu Leu Ala Leu Val Pro Leu Cys Trp Phe Ala Asn Ile Val Val
    130                 135                 140

Arg Glu Phe Tyr Asp Pro Ser Val Pro Val Ser Gln Lys Tyr Glu Leu
145                 150                 155                 160

Gly Ala Ala Leu Tyr Ile Gly Trp Ala Ala Thr Ala Leu Leu Met Val
                165                 170                 175

Gly Gly Cys Leu Leu Cys Cys Gly Ala Trp Val Cys Thr Gly Arg Pro
            180                 185                 190

Asp Leu Ser Phe Pro Val Lys Tyr Ser Ala Pro Arg Pro Thr Ala
        195                 200                 205

Thr Gly Asp Tyr Asp Lys Lys Asn Tyr Val
        210                 215

<210> SEQ ID NO 43
<211> LENGTH: 218
<212> TYPE: PRT
<213> ORGANISM: Artificial Sequence
<220> FEATURE:
<223> OTHER INFORMATION: S151T

<400> SEQUENCE: 43

Met Gly Ser Ala Ala Leu Glu Ile Leu Gly Leu Val Leu Cys Leu Val
1               5                   10                  15

Gly Trp Gly Gly Leu Ile Leu Ala Cys Gly Leu Pro Met Trp Gln Val
            20                  25                  30

Thr Ala Phe Leu Asp His Asn Ile Val Thr Ala Gln Thr Thr Trp Lys
```

```
            35                  40                  45
Gly Leu Trp Met Ser Cys Val Val Gln Ser Thr Gly His Met Gln Cys
     50                  55                  60

Lys Val Tyr Asp Ser Val Leu Ala Leu Ser Thr Glu Val Gln Ala Ala
 65                  70                  75                  80

Arg Ala Leu Thr Val Ser Ala Val Leu Leu Ala Phe Val Ala Leu Phe
                 85                  90                  95

Val Thr Leu Ala Gly Ala Gln Cys Thr Thr Cys Val Ala Pro Gly Pro
             100                 105                 110

Ala Lys Ala Arg Val Ala Leu Thr Gly Gly Val Leu Tyr Leu Phe Cys
         115                 120                 125

Gly Leu Leu Ala Leu Val Pro Leu Cys Trp Phe Ala Asn Ile Val Val
     130                 135                 140

Arg Glu Phe Tyr Asp Pro Thr Val Pro Val Ser Gln Lys Tyr Glu Leu
145                 150                 155                 160

Gly Ala Ala Leu Tyr Ile Gly Trp Ala Ala Thr Ala Leu Leu Met Val
                165                 170                 175

Gly Gly Cys Leu Leu Cys Cys Gly Ala Trp Val Cys Thr Gly Arg Pro
            180                 185                 190

Asp Leu Ser Phe Pro Val Lys Tyr Ser Ala Pro Arg Pro Thr Ala
        195                 200                 205

Thr Gly Asp Tyr Asp Lys Lys Asn Tyr Val
    210                 215
```

<210> SEQ ID NO 44
<211> LENGTH: 218
<212> TYPE: PRT
<213> ORGANISM: Artificial Sequence
<220> FEATURE:
<223> OTHER INFORMATION: TM

<400> SEQUENCE: 44

```
Met Gly Ser Ala Ala Leu Glu Ile Leu Gly Leu Val Leu Cys Leu Val
 1               5                  10                  15

Gly Trp Val Gly Leu Ile Leu Ala Cys Gly Leu Pro Met Trp Gln Val
                 20                  25                  30

Thr Ala Phe Leu Asp His Asn Ile Val Thr Ala Gln Thr Thr Trp Lys
             35                  40                  45

Gly Leu Trp Met Ser Cys Val Val Gln Ser Thr Gly His Met Gln Cys
         50                  55                  60

Lys Val Tyr Asp Ser Val Leu Ala Leu Ser Thr Glu Val Gln Ala Ala
 65                  70                  75                  80

Arg Ala Leu Thr Val Ser Ala Val Leu Leu Ala Leu Val Ala Leu Phe
                 85                  90                  95

Val Thr Leu Thr Gly Ala Gln Cys Thr Thr Cys Val Ala Pro Gly Pro
             100                 105                 110

Val Lys Ala Arg Val Ala Leu Thr Gly Gly Ala Leu Tyr Ala Val Cys
         115                 120                 125

Gly Leu Leu Ala Leu Val Pro Leu Cys Trp Phe Ala Asn Ile Val Val
    130                 135                 140

Arg Glu Phe Tyr Asp Pro Ser Val Pro Val Ser Gln Lys Tyr Glu Leu
145                 150                 155                 160

Gly Ala Ala Leu Tyr Ile Gly Trp Ala Ala Thr Ala Leu Leu Met Val
                165                 170                 175

Gly Gly Gly Leu Val Cys Cys Gly Ala Trp Val Cys Thr Gly Arg Pro
```

```
                180             185             190
Glu Phe Ser Phe Pro Val Lys Tyr Ser Ala Pro Arg Arg Pro Thr Ala
            195                 200                 205
Asn Gly Asp Tyr Asp Lys Lys Asn Tyr Val
        210                 215

<210> SEQ ID NO 45
<211> LENGTH: 218
<212> TYPE: PRT
<213> ORGANISM: Artificial Sequence
<220> FEATURE:
<223> OTHER INFORMATION: 1-1-5

<400> SEQUENCE: 45

Met Gly Ser Ala Ala Leu Glu Ile Leu Gly Leu Val Leu Cys Leu Val
1               5                   10                  15
Gly Trp Gly Gly Leu Ile Leu Ala Cys Ala Leu Pro Gln Trp Arg Ile
            20                  25                  30
Tyr Ser Tyr Ala Gly Asp Asn Ile Val Thr Ala Gln Ala Met Tyr Glu
        35                  40                  45
Gly Leu Trp Met Ser Cys Val Ser Gln Ser Thr Gly Gln Ile Gln Cys
    50                  55                  60
Lys Val Phe Asp Ser Leu Leu Asn Leu Ser Ser Thr Val Gln Ala Ala
65                  70                  75                  80
Arg Ala Leu Thr Val Ser Ala Val Leu Leu Ala Phe Val Ala Leu Phe
                85                  90                  95
Val Thr Leu Ala Gly Ala Gln Cys Thr Thr Cys Val Ala Pro Gly Pro
            100                 105                 110
Ala Lys Ala Arg Val Ala Leu Thr Gly Gly Val Leu Tyr Leu Phe Cys
        115                 120                 125
Gly Leu Leu Ala Leu Val Pro Leu Cys Trp Phe Ala Asn Ile Val Val
    130                 135                 140
Arg Glu Phe Tyr Asp Pro Ser Val Pro Val Ser Gln Lys Tyr Glu Leu
145                 150                 155                 160
Gly Ala Ala Leu Tyr Ile Gly Trp Ala Ala Thr Ala Leu Leu Met Val
                165                 170                 175
Gly Gly Cys Leu Leu Cys Cys Gly Ala Trp Val Cys Thr Gly Arg Pro
            180                 185                 190
Asp Leu Ser Phe Pro Val Lys Tyr Ser Ala Pro Arg Arg Pro Thr Ala
        195                 200                 205
Thr Gly Asp Tyr Asp Lys Lys Asn Tyr Val
    210                 215

<210> SEQ ID NO 46
<211> LENGTH: 218
<212> TYPE: PRT
<213> ORGANISM: Artificial Sequence
<220> FEATURE:
<223> OTHER INFORMATION: 1-5-5

<400> SEQUENCE: 46

Met Gly Ser Ala Ala Leu Glu Ile Leu Gly Leu Val Leu Cys Leu Val
1               5                   10                  15
Gly Trp Gly Gly Leu Ile Leu Ala Cys Ala Leu Pro Gln Trp Arg Ile
            20                  25                  30
Tyr Ser Tyr Ala Gly Asp Asn Ile Val Thr Ala Gln Ala Met Tyr Glu
        35                  40                  45
```

```
Gly Leu Trp Met Ser Cys Val Val Gln Ser Thr Gly His Met Gln Cys
 50                  55                  60

Lys Val Tyr Asp Ser Val Leu Ala Leu Ser Thr Glu Val Gln Ala Ala
 65                  70                  75                  80

Arg Ala Leu Thr Val Ser Ala Val Leu Leu Ala Phe Val Ala Leu Phe
                 85                  90                  95

Val Thr Leu Ala Gly Ala Gln Cys Thr Thr Cys Val Ala Pro Gly Pro
                100                 105                 110

Ala Lys Ala Arg Val Ala Leu Thr Gly Gly Val Leu Tyr Leu Phe Cys
            115                 120                 125

Gly Leu Leu Ala Leu Val Pro Leu Cys Trp Phe Ala Asn Ile Val Val
130                 135                 140

Arg Glu Phe Tyr Asp Pro Ser Val Pro Val Ser Gln Lys Tyr Glu Leu
145                 150                 155                 160

Gly Ala Ala Leu Tyr Ile Gly Trp Ala Ala Thr Ala Leu Leu Met Val
                165                 170                 175

Gly Gly Cys Leu Leu Cys Cys Gly Ala Trp Val Cys Thr Gly Arg Pro
                180                 185                 190

Asp Leu Ser Phe Pro Val Lys Tyr Ser Ala Pro Arg Arg Pro Thr Ala
            195                 200                 205

Thr Gly Asp Tyr Asp Lys Lys Asn Tyr Val
210                 215

<210> SEQ ID NO 47
<211> LENGTH: 218
<212> TYPE: PRT
<213> ORGANISM: Artificial Sequence
<220> FEATURE:
<223> OTHER INFORMATION: 5-1-5

<400> SEQUENCE: 47

Met Gly Ser Ala Ala Leu Glu Ile Leu Gly Leu Val Leu Cys Leu Val
  1               5                  10                  15

Gly Trp Gly Gly Leu Ile Leu Ala Cys Gly Leu Pro Met Trp Gln Val
                 20                  25                  30

Thr Ala Phe Leu Asp His Asn Ile Val Thr Ala Gln Thr Thr Trp Lys
             35                  40                  45

Gly Leu Trp Met Ser Cys Val Ser Gln Ser Thr Gly Gln Ile Gln Cys
 50                  55                  60

Lys Val Phe Asp Ser Leu Leu Asn Leu Ser Ser Thr Val Gln Ala Ala
 65                  70                  75                  80

Arg Ala Leu Thr Val Ser Ala Val Leu Leu Ala Phe Val Ala Leu Phe
                 85                  90                  95

Val Thr Leu Ala Gly Ala Gln Cys Thr Thr Cys Val Ala Pro Gly Pro
                100                 105                 110

Ala Lys Ala Arg Val Ala Leu Thr Gly Gly Val Leu Tyr Leu Phe Cys
            115                 120                 125

Gly Leu Leu Ala Leu Val Pro Leu Cys Trp Phe Ala Asn Ile Val Val
130                 135                 140

Arg Glu Phe Tyr Asp Pro Ser Val Pro Val Ser Gln Lys Tyr Glu Leu
145                 150                 155                 160

Gly Ala Ala Leu Tyr Ile Gly Trp Ala Ala Thr Ala Leu Leu Met Val
                165                 170                 175

Gly Gly Cys Leu Leu Cys Cys Gly Ala Trp Val Cys Thr Gly Arg Pro
                180                 185                 190
```

Asp Leu Ser Phe Pro Val Lys Tyr Ser Ala Pro Arg Pro Thr Ala
    195                 200                 205

Thr Gly Asp Tyr Asp Lys Lys Asn Tyr Val
    210                 215

<210> SEQ ID NO 48
<211> LENGTH: 218
<212> TYPE: PRT
<213> ORGANISM: Artificial Sequence
<220> FEATURE:
<223> OTHER INFORMATION: 5-5-1

<400> SEQUENCE: 48

Met Gly Ser Ala Ala Leu Glu Ile Leu Gly Leu Val Leu Cys Leu Val
1               5                   10                  15

Gly Trp Gly Gly Leu Ile Leu Ala Cys Gly Leu Pro Met Trp Gln Val
            20                  25                  30

Thr Ala Phe Leu Asp His Asn Ile Val Thr Ala Gln Thr Thr Trp Lys
        35                  40                  45

Gly Leu Trp Met Ser Cys Val Val Gln Ser Thr Gly His Met Gln Cys
    50                  55                  60

Lys Val Tyr Asp Ser Val Leu Ala Leu Ser Thr Glu Val Gln Ala Ala
65                  70                  75                  80

Arg Ala Leu Thr Val Ser Ala Val Leu Leu Ala Phe Val Ala Leu Phe
                85                  90                  95

Val Thr Leu Ala Gly Ala Gln Cys Thr Thr Cys Val Ala Pro Gly Pro
            100                 105                 110

Ala Lys Ala Arg Val Ala Leu Thr Gly Gly Val Leu Tyr Leu Phe Cys
        115                 120                 125

Gly Leu Leu Ala Leu Val Pro Leu Cys Trp Phe Ala Asn Ile Val Val
    130                 135                 140

Arg Glu Phe Tyr Asp Pro Met Thr Pro Val Asn Ala Arg Tyr Glu Phe
145                 150                 155                 160

Gly Gln Ala Leu Tyr Ile Gly Trp Ala Ala Thr Ala Leu Leu Met Val
                165                 170                 175

Gly Gly Cys Leu Leu Cys Cys Gly Ala Trp Val Cys Thr Gly Arg Pro
            180                 185                 190

Asp Leu Ser Phe Pro Val Lys Tyr Ser Ala Pro Arg Pro Thr Ala
        195                 200                 205

Thr Gly Asp Tyr Asp Lys Lys Asn Tyr Val
    210                 215

<210> SEQ ID NO 49
<211> LENGTH: 25
<212> TYPE: PRT
<213> ORGANISM: Artificial Sequence
<220> FEATURE:
<223> OTHER INFORMATION: M3 heavy chain FR1

<400> SEQUENCE: 49

Glu Val Gln Leu Gln Gln Ser Gly Pro Glu Leu Val Lys Pro Gly Ala
1               5                   10                  15

Ser Val Lys Ile Ser Cys Lys Ala Ser
            20                  25

<210> SEQ ID NO 50
<211> LENGTH: 7
<212> TYPE: PRT
<213> ORGANISM: Artificial Sequence

```
<220> FEATURE:
<223> OTHER INFORMATION: M3 heavy chain CDR1

<400> SEQUENCE: 50

Gly Tyr Ser Phe Thr Gly Tyr
1               5

<210> SEQ ID NO 51
<211> LENGTH: 19
<212> TYPE: PRT
<213> ORGANISM: Artificial Sequence
<220> FEATURE:
<223> OTHER INFORMATION: M3 heavy chain FR2

<400> SEQUENCE: 51

Tyr Met Asn Trp Val Lys Gln Ser Pro Glu Lys Ser Leu Glu Trp Ile
1               5                   10                  15

Gly Asp Ile

<210> SEQ ID NO 52
<211> LENGTH: 6
<212> TYPE: PRT
<213> ORGANISM: Artificial Sequence
<220> FEATURE:
<223> OTHER INFORMATION: M3 heavy chain CDR2

<400> SEQUENCE: 52

Asn Pro Ser Thr Gly Gly
1               5

<210> SEQ ID NO 53
<211> LENGTH: 41
<212> TYPE: PRT
<213> ORGANISM: Artificial Sequence
<220> FEATURE:
<223> OTHER INFORMATION: M3 heavy chain FR3

<400> SEQUENCE: 53

Ala Thr Tyr Asn Gln Lys Phe Lys Ala Lys Ala Thr Leu Thr Val Asp
1               5                   10                  15

Lys Ser Ser Ser Thr Ala Tyr Met Gln Leu Lys Ser Leu Thr Ser Glu
            20                  25                  30

Asp Ser Ala Val Phe Tyr Cys Ala Leu
        35                  40

<210> SEQ ID NO 54
<211> LENGTH: 8
<212> TYPE: PRT
<213> ORGANISM: Artificial Sequence
<220> FEATURE:
<223> OTHER INFORMATION: M3 heavy chain CDR3

<400> SEQUENCE: 54

Tyr Ser Asn Tyr Gly Phe Val Tyr
1               5

<210> SEQ ID NO 55
<211> LENGTH: 11
<212> TYPE: PRT
<213> ORGANISM: Artificial Sequence
<220> FEATURE:
<223> OTHER INFORMATION: M3 heavy chain FR4

<400> SEQUENCE: 55

Trp Gly Gln Gly Thr Leu Val Thr Val Ser Ala
```

```
1               5                   10
```

<210> SEQ ID NO 56
<211> LENGTH: 25
<212> TYPE: PRT
<213> ORGANISM: Artificial Sequence
<220> FEATURE:
<223> OTHER INFORMATION: M11 heavy chain FR1

<400> SEQUENCE: 56

```
Gln Val Gln Leu Lys Gln Ser Gly Pro Gly Leu Val Gln Pro Ser Gln
1               5                   10                  15

Ser Leu Ser Ile Thr Cys Thr Val Ser
            20                  25
```

<210> SEQ ID NO 57
<211> LENGTH: 7
<212> TYPE: PRT
<213> ORGANISM: Artificial Sequence
<220> FEATURE:
<223> OTHER INFORMATION: M11 heavy chain CDR1

<400> SEQUENCE: 57

```
Gly Phe Ser Leu Ile Arg Tyr
1               5
```

<210> SEQ ID NO 58
<211> LENGTH: 19
<212> TYPE: PRT
<213> ORGANISM: Artificial Sequence
<220> FEATURE:
<223> OTHER INFORMATION: M11 heavy chain FR2

<400> SEQUENCE: 58

```
Gly Val His Trp Val Arg Gln Ser Pro Gly Lys Gly Leu Glu Trp Leu
1               5                   10                  15

Gly Val Lys
```

<210> SEQ ID NO 59
<211> LENGTH: 5
<212> TYPE: PRT
<213> ORGANISM: Artificial Sequence
<220> FEATURE:
<223> OTHER INFORMATION: M11 heavy chain CDR2

<400> SEQUENCE: 59

```
Trp Ser Gly Gly Ser
1               5
```

<210> SEQ ID NO 60
<211> LENGTH: 41
<212> TYPE: PRT
<213> ORGANISM: Artificial Sequence
<220> FEATURE:
<223> OTHER INFORMATION: M11 heavy chain FR3

<400> SEQUENCE: 60

```
Thr Asp Tyr Asn Gly Ala Phe Lys Ser Arg Leu Ser Ile Ser Lys Asp
1               5                   10                  15

Asn Ser Lys Ser Gln Val Phe Phe Lys Met Asn Ser Leu Gln Ala Asp
            20                  25                  30

Asp Thr Ala Ile Tyr Tyr Cys Ala Arg
        35                  40
```

-continued

```
<210> SEQ ID NO 61
<211> LENGTH: 10
<212> TYPE: PRT
<213> ORGANISM: Artificial Sequence
<220> FEATURE:
<223> OTHER INFORMATION: M11 heavy chain CDR3

<400> SEQUENCE: 61

Gly Leu Asp Gly Tyr Tyr Val Pro Asp Val
1               5                   10

<210> SEQ ID NO 62
<211> LENGTH: 10
<212> TYPE: PRT
<213> ORGANISM: Artificial Sequence
<220> FEATURE:
<223> OTHER INFORMATION: M11 heavy chain FR4

<400> SEQUENCE: 62

Trp Gly Thr Gly Thr Ser Val Thr Val Ser
1               5                   10

<210> SEQ ID NO 63
<211> LENGTH: 25
<212> TYPE: PRT
<213> ORGANISM: Artificial Sequence
<220> FEATURE:
<223> OTHER INFORMATION: M23 heavy chain FR1

<400> SEQUENCE: 63

Glu Val Gln Leu Gln Gln Ser Gly Pro Val Leu Val Lys Pro Gly Pro
1               5                   10                  15

Ser Val Met Ile Ser Cys Lys Ala Ser
            20                  25

<210> SEQ ID NO 64
<211> LENGTH: 7
<212> TYPE: PRT
<213> ORGANISM: Artificial Sequence
<220> FEATURE:
<223> OTHER INFORMATION: M23 heavy chain CDR1

<400> SEQUENCE: 64

Gly Phe Thr Phe Thr Asp Tyr
1               5

<210> SEQ ID NO 65
<211> LENGTH: 19
<212> TYPE: PRT
<213> ORGANISM: Artificial Sequence
<220> FEATURE:
<223> OTHER INFORMATION: M23 heavy chain FR2

<400> SEQUENCE: 65

Tyr Met His Trp Val Lys Gln Ser His Gly Lys Ser Leu Glu Trp Ile
1               5                   10                  15

Gly Leu Val

<210> SEQ ID NO 66
<211> LENGTH: 6
<212> TYPE: PRT
<213> ORGANISM: Artificial Sequence
<220> FEATURE:
<223> OTHER INFORMATION: M23 heavy chain CDR2

<400> SEQUENCE: 66
```

Tyr Pro Tyr Asn Gly Gly
1               5

<210> SEQ ID NO 67
<211> LENGTH: 41
<212> TYPE: PRT
<213> ORGANISM: Artificial Sequence
<220> FEATURE:
<223> OTHER INFORMATION: M23 heavy chain FR3

<400> SEQUENCE: 67

Thr Asp Tyr Asn Gln Lys Phe Lys Gly Lys Ala Thr Leu Thr Val Asp
1               5                   10                  15

Thr Ser Ser Ser Thr Ala Tyr Met Glu Leu Asn Ser Leu Thr Ser Glu
            20                  25                  30

Asp Ser Ala Val Tyr Tyr Cys Ala Arg
        35                  40

<210> SEQ ID NO 68
<211> LENGTH: 13
<212> TYPE: PRT
<213> ORGANISM: Artificial Sequence
<220> FEATURE:
<223> OTHER INFORMATION: M23 heavy chain CDR3

<400> SEQUENCE: 68

Cys Leu Tyr Asp Gly Leu Tyr Phe Tyr Ala Met Asp Tyr
1               5                   10

<210> SEQ ID NO 69
<211> LENGTH: 11
<212> TYPE: PRT
<213> ORGANISM: Artificial Sequence
<220> FEATURE:
<223> OTHER INFORMATION: M23 heavy chain FR4

<400> SEQUENCE: 69

Trp Gly Gln Gly Thr Ser Val Thr Val Ser Ser
1               5                   10

<210> SEQ ID NO 70
<211> LENGTH: 25
<212> TYPE: PRT
<213> ORGANISM: Artificial Sequence
<220> FEATURE:
<223> OTHER INFORMATION: M29 heavy chain FR1

<400> SEQUENCE: 70

Glu Val Gln Leu Val Glu Ser Gly Gly Gly Leu Val Gln Pro Lys Gly
1               5                   10                  15

Ser Leu Lys Leu Ser Cys Ala Ala Ser
            20                  25

<210> SEQ ID NO 71
<211> LENGTH: 7
<212> TYPE: PRT
<213> ORGANISM: Artificial Sequence
<220> FEATURE:
<223> OTHER INFORMATION: M29 heavy chain CDR1

<400> SEQUENCE: 71

Gly Phe Thr Phe Asn Ile Tyr
1               5

<210> SEQ ID NO 72

```
<211> LENGTH: 19
<212> TYPE: PRT
<213> ORGANISM: Artificial Sequence
<220> FEATURE:
<223> OTHER INFORMATION: M29 heavy chain FR2

<400> SEQUENCE: 72

Ala Met His Trp Val Arg Gln Ala Pro Gly Lys Gly Leu Glu Trp Val
1               5                   10                  15

Ala Arg Ile

<210> SEQ ID NO 73
<211> LENGTH: 8
<212> TYPE: PRT
<213> ORGANISM: Artificial Sequence
<220> FEATURE:
<223> OTHER INFORMATION: M29 heavy chain CDR2

<400> SEQUENCE: 73

Arg Ser Lys Ser Ser Asn Tyr Ala
1               5

<210> SEQ ID NO 74
<211> LENGTH: 41
<212> TYPE: PRT
<213> ORGANISM: Artificial Sequence
<220> FEATURE:
<223> OTHER INFORMATION: M29 heavy chain FR3

<400> SEQUENCE: 74

Thr Tyr Tyr Val Asp Ser Val Lys Asp Arg Phe Ile Ile Ser Arg Asp
1               5                   10                  15

Asp Ser Gln Ser Met Leu Tyr Leu Gln Val Asn Asn Leu Lys Thr Glu
            20                  25                  30

Asp Thr Ala Met Tyr Tyr Cys Val Arg
        35                  40

<210> SEQ ID NO 75
<211> LENGTH: 9
<212> TYPE: PRT
<213> ORGANISM: Artificial Sequence
<220> FEATURE:
<223> OTHER INFORMATION: M29 heavy chain CDR3

<400> SEQUENCE: 75

Glu Gly Asn Trp Asp Cys Phe Asp Tyr
1               5

<210> SEQ ID NO 76
<211> LENGTH: 11
<212> TYPE: PRT
<213> ORGANISM: Artificial Sequence
<220> FEATURE:
<223> OTHER INFORMATION: M29 heavy chain FR4

<400> SEQUENCE: 76

Trp Gly Gln Gly Thr Thr Leu Thr Val Ser Ser
1               5                   10

<210> SEQ ID NO 77
<211> LENGTH: 25
<212> TYPE: PRT
<213> ORGANISM: Artificial Sequence
<220> FEATURE:
<223> OTHER INFORMATION: M48 heavy chain FR1
```

```
<400> SEQUENCE: 77

Gln Ala Tyr Leu Gln Gln Ser Gly Ala Glu Leu Val Arg Pro Gly Ala
1               5                   10                  15

Ser Val Lys Met Ser Cys Lys Ala Ser
            20                  25

<210> SEQ ID NO 78
<211> LENGTH: 7
<212> TYPE: PRT
<213> ORGANISM: Artificial Sequence
<220> FEATURE:
<223> OTHER INFORMATION: M48 heavy chain CDR1

<400> SEQUENCE: 78

Gly Tyr Thr Phe Thr Ser Tyr
1               5

<210> SEQ ID NO 79
<211> LENGTH: 19
<212> TYPE: PRT
<213> ORGANISM: Artificial Sequence
<220> FEATURE:
<223> OTHER INFORMATION: M48 heavy chain FR2

<400> SEQUENCE: 79

Asn Met His Trp Val Lys Lys Thr Arg Arg Gln Gly Leu Glu Trp Ile
1               5                   10                  15

Gly Ala Ile

<210> SEQ ID NO 80
<211> LENGTH: 6
<212> TYPE: PRT
<213> ORGANISM: Artificial Sequence
<220> FEATURE:
<223> OTHER INFORMATION: M48 heavy chain CDR2

<400> SEQUENCE: 80

Ser Pro Gly Asn Gly Asn
1               5

<210> SEQ ID NO 81
<211> LENGTH: 41
<212> TYPE: PRT
<213> ORGANISM: Artificial Sequence
<220> FEATURE:
<223> OTHER INFORMATION: M48 heavy chain FR3

<400> SEQUENCE: 81

Thr Ser Tyr Asn Gln Lys Phe Lys Gly Lys Ala Thr Leu Thr Val Asp
1               5                   10                  15

Lys Ser Ser Ser Thr Ala Tyr Met Gln Leu Ser Ser Leu Thr Ser Glu
            20                  25                  30

Asp Ser Ala Val Tyr Phe Cys Ala Arg
        35                  40

<210> SEQ ID NO 82
<211> LENGTH: 10
<212> TYPE: PRT
<213> ORGANISM: Artificial Sequence
<220> FEATURE:
<223> OTHER INFORMATION: M48 heavy chain CDR3

<400> SEQUENCE: 82

Asp Asp Gly Tyr Tyr Gly Ala Leu Asp Tyr
```

```
                   1               5                  10

<210> SEQ ID NO 83
<211> LENGTH: 11
<212> TYPE: PRT
<213> ORGANISM: Artificial Sequence
<220> FEATURE:
<223> OTHER INFORMATION: M48 heavy chain FR4

<400> SEQUENCE: 83

Trp Gly Gln Gly Thr Ser Val Thr Val Ser Ser
 1               5                  10

<210> SEQ ID NO 84
<211> LENGTH: 25
<212> TYPE: PRT
<213> ORGANISM: Artificial Sequence
<220> FEATURE:
<223> OTHER INFORMATION: R2 heavy chain FR1

<400> SEQUENCE: 84

Gln Val Gln Leu Lys Glu Ser Gly Pro Gly Leu Val Gln Pro Ser Gln
 1               5                  10                  15

Thr Leu Ser Leu Thr Cys Thr Val Ser
            20                  25

<210> SEQ ID NO 85
<211> LENGTH: 7
<212> TYPE: PRT
<213> ORGANISM: Artificial Sequence
<220> FEATURE:
<223> OTHER INFORMATION: R2 heavy chain CDR1

<400> SEQUENCE: 85

Gly Leu Ser Leu Ile Arg Asn
 1               5

<210> SEQ ID NO 86
<211> LENGTH: 19
<212> TYPE: PRT
<213> ORGANISM: Artificial Sequence
<220> FEATURE:
<223> OTHER INFORMATION: R2 heavy chain FR2

<400> SEQUENCE: 86

Ser Val Ser Trp Ile Arg Gln Pro Pro Gly Lys Gly Leu Glu Trp Met
 1               5                  10                  15

Gly Val Ile

<210> SEQ ID NO 87
<211> LENGTH: 5
<212> TYPE: PRT
<213> ORGANISM: Artificial Sequence
<220> FEATURE:
<223> OTHER INFORMATION: R2 heavy chain CDR2

<400> SEQUENCE: 87

Trp Ser Asn Gly Gly
 1               5

<210> SEQ ID NO 88
<211> LENGTH: 41
<212> TYPE: PRT
<213> ORGANISM: Artificial Sequence
<220> FEATURE:
<223> OTHER INFORMATION: R2 heavy chain FR3
```

<400> SEQUENCE: 88

Thr Glu Tyr Asn Ser Thr Val Lys Ser Arg Leu Ser Ile Ser Arg Asp
1               5                   10                  15

Thr Ser Lys Asn Gln Val Phe Leu Lys Met Asn Ser Leu Gln Thr Glu
            20                  25                  30

Asp Ser Ala Met Phe Phe Cys Ala Arg
        35                  40

<210> SEQ ID NO 89
<211> LENGTH: 11
<212> TYPE: PRT
<213> ORGANISM: Artificial Sequence
<220> FEATURE:
<223> OTHER INFORMATION: R2 heavy chain CDR3

<400> SEQUENCE: 89

Thr Pro Asp Gly Tyr Tyr Pro Tyr Phe Asp Tyr
1               5                   10

<210> SEQ ID NO 90
<211> LENGTH: 11
<212> TYPE: PRT
<213> ORGANISM: Artificial Sequence
<220> FEATURE:
<223> OTHER INFORMATION: R2 heavy chain FR4

<400> SEQUENCE: 90

Trp Gly Gln Gly Val Met Val Thr Val Ser Ser
1               5                   10

<210> SEQ ID NO 91
<211> LENGTH: 25
<212> TYPE: PRT
<213> ORGANISM: Artificial Sequence
<220> FEATURE:
<223> OTHER INFORMATION: R3 heavy chain FR1

<400> SEQUENCE: 91

Glu Val Gln Leu Val Glu Ser Gly Gly Gly Leu Val Gln Pro Gly Arg
1               5                   10                  15

Ser Leu Lys Leu Ser Cys Ala Ala Ser
            20                  25

<210> SEQ ID NO 92
<211> LENGTH: 7
<212> TYPE: PRT
<213> ORGANISM: Artificial Sequence
<220> FEATURE:
<223> OTHER INFORMATION: R3 heavy chain CDR1

<400> SEQUENCE: 92

Gly Phe Thr Phe Ser Asp Tyr
1               5

<210> SEQ ID NO 93
<211> LENGTH: 19
<212> TYPE: PRT
<213> ORGANISM: Artificial Sequence
<220> FEATURE:
<223> OTHER INFORMATION: R3 heavy chain FR2

<400> SEQUENCE: 93

Tyr Met Ala Trp Val Arg Gln Ala Pro Lys Lys Gly Leu Glu Trp Val
1               5                   10                  15

Ala Ser Ile

<210> SEQ ID NO 94
<211> LENGTH: 6
<212> TYPE: PRT
<213> ORGANISM: Artificial Sequence
<220> FEATURE:
<223> OTHER INFORMATION: R3 heavy chain CDR2

<400> SEQUENCE: 94

Ser Tyr Glu Gly Arg Asn
1               5

<210> SEQ ID NO 95
<211> LENGTH: 41
<212> TYPE: PRT
<213> ORGANISM: Artificial Sequence
<220> FEATURE:
<223> OTHER INFORMATION: R3 heavy chain FR3

<400> SEQUENCE: 95

Thr Tyr Tyr Gly Asp Ser Val Lys Gly Arg Phe Thr Ile Ser Arg Asp
1               5                   10                  15

Asn Ala Lys Ser Thr Leu Tyr Leu Gln Met Lys Ser Leu Arg Ser Glu
            20                  25                  30

Asp Thr Ala Thr Tyr Tyr Cys Thr Arg
        35                  40

<210> SEQ ID NO 96
<211> LENGTH: 8
<212> TYPE: PRT
<213> ORGANISM: Artificial Sequence
<220> FEATURE:
<223> OTHER INFORMATION: R3 heavy chain CDR3

<400> SEQUENCE: 96

His Pro Arg Arg Tyr Phe Asp Tyr
1               5

<210> SEQ ID NO 97
<211> LENGTH: 11
<212> TYPE: PRT
<213> ORGANISM: Artificial Sequence
<220> FEATURE:
<223> OTHER INFORMATION: R3 heavy chain FR4

<400> SEQUENCE: 97

Trp Gly Gln Gly Val Met Val Thr Val Ser Ser
1               5                   10

<210> SEQ ID NO 98
<211> LENGTH: 24
<212> TYPE: PRT
<213> ORGANISM: Artificial Sequence
<220> FEATURE:
<223> OTHER INFORMATION: R8 heavy chain FR1

<400> SEQUENCE: 98

Val Lys Val Val Glu Ser Gly Gly Gly Leu Val Gln Pro Gly Arg Ser
1               5                   10                  15

Met Lys Leu Ser Cys Ala Ala Ser
            20

<210> SEQ ID NO 99

```
<211> LENGTH: 7
<212> TYPE: PRT
<213> ORGANISM: Artificial Sequence
<220> FEATURE:
<223> OTHER INFORMATION: R8 heavy chain CDR1

<400> SEQUENCE: 99

Gly Phe Thr Phe Ser Asp Tyr
1               5

<210> SEQ ID NO 100
<211> LENGTH: 19
<212> TYPE: PRT
<213> ORGANISM: Artificial Sequence
<220> FEATURE:
<223> OTHER INFORMATION: R8 heavy chain FR2

<400> SEQUENCE: 100

Phe Met Ala Trp Val Arg Gln Ser Pro Lys Lys Gly Leu Glu Trp Val
1               5                   10                  15

Ala Ser Ile

<210> SEQ ID NO 101
<211> LENGTH: 6
<212> TYPE: PRT
<213> ORGANISM: Artificial Sequence
<220> FEATURE:
<223> OTHER INFORMATION: R8 heavy chain CDR2

<400> SEQUENCE: 101

Asn Tyr Gly Gly Ser Arg
1               5

<210> SEQ ID NO 102
<211> LENGTH: 41
<212> TYPE: PRT
<213> ORGANISM: Artificial Sequence
<220> FEATURE:
<223> OTHER INFORMATION: R8 heavy chain FR3

<400> SEQUENCE: 102

Thr Tyr Tyr Glu Asp Ser Val Lys Gly Arg Phe Thr Ile Ser Arg Asp
1               5                   10                  15

Asn Ala Lys Ser Thr Leu Tyr Leu Gln Met Asn Ser Leu Arg Ser Glu
            20                  25                  30

Asp Thr Ala Thr Tyr Tyr Cys Ala Arg
        35                  40

<210> SEQ ID NO 103
<211> LENGTH: 8
<212> TYPE: PRT
<213> ORGANISM: Artificial Sequence
<220> FEATURE:
<223> OTHER INFORMATION: R8 heavy chain CDR3

<400> SEQUENCE: 103

His Pro His Arg Leu Phe Asp Tyr
1               5

<210> SEQ ID NO 104
<211> LENGTH: 11
<212> TYPE: PRT
<213> ORGANISM: Artificial Sequence
<220> FEATURE:
<223> OTHER INFORMATION: R8 heavy chain FR4
```

```
<400> SEQUENCE: 104

Trp Gly Gln Gly Val Met Val Thr Val Ser Ser
1               5                   10

<210> SEQ ID NO 105
<211> LENGTH: 25
<212> TYPE: PRT
<213> ORGANISM: Artificial Sequence
<220> FEATURE:
<223> OTHER INFORMATION: R9 heavy chain FR1

<400> SEQUENCE: 105

Gln Val Thr Leu Lys Glu Ser Gly Pro Gly Ile Leu Gln Pro Ser His
1               5                   10                  15

Thr Leu Ser Leu Thr Cys Ser Phe Ser
            20                  25

<210> SEQ ID NO 106
<211> LENGTH: 9
<212> TYPE: PRT
<213> ORGANISM: Artificial Sequence
<220> FEATURE:
<223> OTHER INFORMATION: R9 heavy chain CDR1

<400> SEQUENCE: 106

Gly Phe Ser Leu Asn Thr Tyr Gly Val
1               5

<210> SEQ ID NO 107
<211> LENGTH: 19
<212> TYPE: PRT
<213> ORGANISM: Artificial Sequence
<220> FEATURE:
<223> OTHER INFORMATION: R9 heavy chain FR2

<400> SEQUENCE: 107

Gly Val Asn Trp Ile Arg Gln Pro Ser Gly Lys Gly Leu Glu Trp Leu
1               5                   10                  15

Ala Ser Ile

<210> SEQ ID NO 108
<211> LENGTH: 5
<212> TYPE: PRT
<213> ORGANISM: Artificial Sequence
<220> FEATURE:
<223> OTHER INFORMATION: R9 heavy chain CDR2

<400> SEQUENCE: 108

Trp Trp His Gly Lys
1               5

<210> SEQ ID NO 109
<211> LENGTH: 41
<212> TYPE: PRT
<213> ORGANISM: Artificial Sequence
<220> FEATURE:
<223> OTHER INFORMATION: R9 heavy chain FR3

<400> SEQUENCE: 109

Thr Tyr Ile Asn Pro Ser Leu Lys Asn Arg Leu Thr Val Ser Lys Asp
1               5                   10                  15

Pro Ser Asn Asn Gln Ala Phe Leu Glu Val Thr Asn Val Asp Pro Ala
            20                  25                  30

Asp Thr Ala Thr Tyr Tyr Cys Ala His
```

<210> SEQ ID NO 110
<211> LENGTH: 8
<212> TYPE: PRT
<213> ORGANISM: Artificial Sequence
<220> FEATURE:
<223> OTHER INFORMATION: R9 heavy chain CDR3

<400> SEQUENCE: 110

Ala Arg Ala Gln Leu Leu Asp Tyr
1               5

<210> SEQ ID NO 111
<211> LENGTH: 11
<212> TYPE: PRT
<213> ORGANISM: Artificial Sequence
<220> FEATURE:
<223> OTHER INFORMATION: R9 heavy chain FR4

<400> SEQUENCE: 111

Trp Gly Gln Gly Val Met Val Thr Val Ser Ser
1               5                   10

<210> SEQ ID NO 112
<211> LENGTH: 25
<212> TYPE: PRT
<213> ORGANISM: Artificial Sequence
<220> FEATURE:
<223> OTHER INFORMATION: R11 heavy chain FR1

<400> SEQUENCE: 112

Glu Val Gln Leu Val Glu Ser Gly Gly Gly Leu Val Gln Pro Gly Arg
1               5                   10                  15

Ser Arg Lys Leu Ser Cys Ala Ala Ser
            20                  25

<210> SEQ ID NO 113
<211> LENGTH: 7
<212> TYPE: PRT
<213> ORGANISM: Artificial Sequence
<220> FEATURE:
<223> OTHER INFORMATION: R11 heavy chain CDR1

<400> SEQUENCE: 113

Gly Phe Thr Phe Asn Asn Tyr
1               5

<210> SEQ ID NO 114
<211> LENGTH: 19
<212> TYPE: PRT
<213> ORGANISM: Artificial Sequence
<220> FEATURE:
<223> OTHER INFORMATION: R11 heavy chain FR2

<400> SEQUENCE: 114

Gly Met Ala Trp Val Arg Gln Ala Pro Thr Lys Gly Leu Glu Trp Val
1               5                   10                  15

Ala Ser Ile

<210> SEQ ID NO 115
<211> LENGTH: 6
<212> TYPE: PRT
<213> ORGANISM: Artificial Sequence
<220> FEATURE:
<223> OTHER INFORMATION: R11 heavy chain CDR2

<400> SEQUENCE: 115

Thr Asn Ser Gly Tyr Thr
1               5

<210> SEQ ID NO 116
<211> LENGTH: 41
<212> TYPE: PRT
<213> ORGANISM: Artificial Sequence
<220> FEATURE:
<223> OTHER INFORMATION: R11 heavy chain FR3

<400> SEQUENCE: 116

Thr Tyr Tyr Arg Asp Ser Val Lys Gly Arg Phe Thr Ile Ser Arg Asp
1               5                   10                  15

Asn Ala Lys Asn Ala Leu Tyr Leu Gln Met Asp Ser Leu Arg Ser Glu
            20                  25                  30

Asp Thr Ala Thr Tyr Tyr Cys Thr Thr
        35                  40

<210> SEQ ID NO 117
<211> LENGTH: 12
<212> TYPE: PRT
<213> ORGANISM: Artificial Sequence
<220> FEATURE:
<223> OTHER INFORMATION: R11 heavy chain CDR3

<400> SEQUENCE: 117

Gly Gly Tyr Gly Gly Tyr Phe Pro Leu Phe Asp Tyr
1               5                   10

<210> SEQ ID NO 118
<211> LENGTH: 11
<212> TYPE: PRT
<213> ORGANISM: Artificial Sequence
<220> FEATURE:
<223> OTHER INFORMATION: R11 heavy chain FR4

<400> SEQUENCE: 118

Trp Gly His Gly Val Met Val Thr Val Ser Ser
1               5                   10

<210> SEQ ID NO 119
<211> LENGTH: 25
<212> TYPE: PRT
<213> ORGANISM: Artificial Sequence
<220> FEATURE:
<223> OTHER INFORMATION: R14 heavy chain FR1

<400> SEQUENCE: 119

Gln Val Thr Leu Lys Glu Ser Gly Pro Gly Ile Leu Gln Pro Ser His
1               5                   10                  15

Thr Leu Ser Leu Thr Cys Ser Phe Ser
            20                  25

<210> SEQ ID NO 120
<211> LENGTH: 9
<212> TYPE: PRT
<213> ORGANISM: Artificial Sequence
<220> FEATURE:
<223> OTHER INFORMATION: R14 heavy chain CDR1

<400> SEQUENCE: 120

Gly Phe Ser Leu Ser Thr Tyr Gly Met
1               5

<210> SEQ ID NO 121
<211> LENGTH: 19
<212> TYPE: PRT
<213> ORGANISM: Artificial Sequence
<220> FEATURE:
<223> OTHER INFORMATION: R14 heavy chain FR2

<400> SEQUENCE: 121

Gly Val Ser Trp Ile Arg Gln Pro Ser Gly Lys Gly Leu Glu Trp Leu
1               5                   10                  15

Ala Ser Ile

<210> SEQ ID NO 122
<211> LENGTH: 5
<212> TYPE: PRT
<213> ORGANISM: Artificial Sequence
<220> FEATURE:
<223> OTHER INFORMATION: R14 heavy chain CDR2

<400> SEQUENCE: 122

Trp Trp Asn Gly Arg
1               5

<210> SEQ ID NO 123
<211> LENGTH: 41
<212> TYPE: PRT
<213> ORGANISM: Artificial Sequence
<220> FEATURE:
<223> OTHER INFORMATION: R14 heavy chain FR3

<400> SEQUENCE: 123

Thr Tyr Thr Asn Pro Ser Leu Met Ser Arg Leu Thr Val Ser Lys Asp
1               5                   10                  15

Thr Ser Thr Asn Gln Ala Phe Leu Arg Val Thr Ser Val Glu Thr Ala
            20                  25                  30

Asp Thr Ala Thr Tyr Tyr Cys Ala His
        35                  40

<210> SEQ ID NO 124
<211> LENGTH: 13
<212> TYPE: PRT
<213> ORGANISM: Artificial Sequence
<220> FEATURE:
<223> OTHER INFORMATION: R14 heavy chain CDR3

<400> SEQUENCE: 124

Thr Pro Tyr Asp Tyr Ser Asn Leu Gly Trp Phe Thr Tyr
1               5                   10

<210> SEQ ID NO 125
<211> LENGTH: 11
<212> TYPE: PRT
<213> ORGANISM: Artificial Sequence
<220> FEATURE:
<223> OTHER INFORMATION: R14 heavy chain FR4

<400> SEQUENCE: 125

Trp Gly Gln Gly Thr Leu Val Thr Val Ser Ser
1               5                   10

<210> SEQ ID NO 126
<211> LENGTH: 25
<212> TYPE: PRT
<213> ORGANISM: Artificial Sequence

```
<220> FEATURE:
<223> OTHER INFORMATION: R20 heavy chain FR1

<400> SEQUENCE: 126

Glu Val Gln Leu Val Glu Ser Gly Gly Gly Leu Val Gln Pro Gly Arg
1               5                   10                  15

Ser Met Lys Leu Ser Cys Ala Val Ser
            20                  25

<210> SEQ ID NO 127
<211> LENGTH: 7
<212> TYPE: PRT
<213> ORGANISM: Artificial Sequence
<220> FEATURE:
<223> OTHER INFORMATION: R20 heavy chain CDR1

<400> SEQUENCE: 127

Gly Phe Thr Phe Ser Asp Tyr
1               5

<210> SEQ ID NO 128
<211> LENGTH: 19
<212> TYPE: PRT
<213> ORGANISM: Artificial Sequence
<220> FEATURE:
<223> OTHER INFORMATION: R20 heavy chain FR2

<400> SEQUENCE: 128

Tyr Met Ala Trp Val Arg Gln Ala Pro Lys Lys Gly Leu Glu Trp Val
1               5                   10                  15

Ala Ser Ile

<210> SEQ ID NO 129
<211> LENGTH: 6
<212> TYPE: PRT
<213> ORGANISM: Artificial Sequence
<220> FEATURE:
<223> OTHER INFORMATION: R20 heavy chain CDR2

<400> SEQUENCE: 129

Ser Tyr Glu Gly Arg Asn
1               5

<210> SEQ ID NO 130
<211> LENGTH: 41
<212> TYPE: PRT
<213> ORGANISM: Artificial Sequence
<220> FEATURE:
<223> OTHER INFORMATION: R20 heavy chain FR3

<400> SEQUENCE: 130

Thr Tyr Tyr Gly Asp Ser Val Lys Gly Arg Phe Thr Ile Ser Arg Asp
1               5                   10                  15

Asn Ala Lys Asn Thr Leu Tyr Leu Gln Met Asn Ser Leu Arg Ser Glu
            20                  25                  30

Asp Thr Ala Thr Tyr Tyr Cys Ala Arg
            35                  40

<210> SEQ ID NO 131
<211> LENGTH: 8
<212> TYPE: PRT
<213> ORGANISM: Artificial Sequence
<220> FEATURE:
<223> OTHER INFORMATION: R20 heavy chain CDR3
```

```
<400> SEQUENCE: 131

His Pro Arg Arg Tyr Phe Asp Phe
1               5

<210> SEQ ID NO 132
<211> LENGTH: 11
<212> TYPE: PRT
<213> ORGANISM: Artificial Sequence
<220> FEATURE:
<223> OTHER INFORMATION: R20 heavy chain FR4

<400> SEQUENCE: 132

Trp Gly Pro Gly Thr Met Val Thr Val Ser Ser
1               5                   10

<210> SEQ ID NO 133
<211> LENGTH: 25
<212> TYPE: PRT
<213> ORGANISM: Artificial Sequence
<220> FEATURE:
<223> OTHER INFORMATION: R28 heavy chain FR1

<400> SEQUENCE: 133

Glu Val Gln Leu Val Glu Ser Gly Gly Gly Leu Val Gln Pro Gly Arg
1               5                   10                  15

Ser Leu Lys Leu Ser Cys Ala Ala Ser
            20                  25

<210> SEQ ID NO 134
<211> LENGTH: 7
<212> TYPE: PRT
<213> ORGANISM: Artificial Sequence
<220> FEATURE:
<223> OTHER INFORMATION: R28 heavy chain CDR1

<400> SEQUENCE: 134

Gly Phe Thr Phe Ser Asp Tyr
1               5

<210> SEQ ID NO 135
<211> LENGTH: 19
<212> TYPE: PRT
<213> ORGANISM: Artificial Sequence
<220> FEATURE:
<223> OTHER INFORMATION: R28 heavy chain FR2

<400> SEQUENCE: 135

Phe Met Ala Trp Val Arg Gln Ala Pro Lys Lys Gly Leu Glu Trp Val
1               5                   10                  15

Ala Ser Ile

<210> SEQ ID NO 136
<211> LENGTH: 6
<212> TYPE: PRT
<213> ORGANISM: Artificial Sequence
<220> FEATURE:
<223> OTHER INFORMATION: R28 heavy chain CDR2

<400> SEQUENCE: 136

Asn Tyr Glu Gly Ser Arg
1               5

<210> SEQ ID NO 137
<211> LENGTH: 41
<212> TYPE: PRT
```

```
<213> ORGANISM: Artificial Sequence
<220> FEATURE:
<223> OTHER INFORMATION: R28 heavy chain FR3

<400> SEQUENCE: 137

Thr Tyr Tyr Gly Asp Ser Val Lys Asp Arg Phe Thr Ile Ser Arg Asp
1               5                   10                  15

Asn Thr Lys Thr Thr Leu Tyr Leu Gln Met Thr Ser Leu Arg Ser Glu
            20                  25                  30

Asp Thr Ala Thr Tyr Tyr Cys Ala Arg
        35                  40

<210> SEQ ID NO 138
<211> LENGTH: 8
<212> TYPE: PRT
<213> ORGANISM: Artificial Sequence
<220> FEATURE:
<223> OTHER INFORMATION: R28 heavy chain CDR3

<400> SEQUENCE: 138

His Pro Arg Arg Tyr Phe Asp Phe
1               5

<210> SEQ ID NO 139
<211> LENGTH: 11
<212> TYPE: PRT
<213> ORGANISM: Artificial Sequence
<220> FEATURE:
<223> OTHER INFORMATION: R28 heavy chain FR4

<400> SEQUENCE: 139

Trp Gly Gln Gly Val Met Val Thr Val Ser Ser
1               5                   10

<210> SEQ ID NO 140
<211> LENGTH: 23
<212> TYPE: PRT
<213> ORGANISM: Artificial Sequence
<220> FEATURE:
<223> OTHER INFORMATION: M3 light chain FR1

<400> SEQUENCE: 140

Asp Val Val Met Thr Gln Thr Pro Leu Thr Leu Ser Val Thr Leu Gly
1               5                   10                  15

Gln Pro Ala Ser Ile Ser Cys
            20

<210> SEQ ID NO 141
<211> LENGTH: 16
<212> TYPE: PRT
<213> ORGANISM: Artificial Sequence
<220> FEATURE:
<223> OTHER INFORMATION: M3 light chain CDR1

<400> SEQUENCE: 141

Lys Ser Ser Gln Ser Leu Leu Tyr Ser Asp Gly Lys Thr Tyr Leu Asn
1               5                   10                  15

<210> SEQ ID NO 142
<211> LENGTH: 15
<212> TYPE: PRT
<213> ORGANISM: Artificial Sequence
<220> FEATURE:
<223> OTHER INFORMATION: M3 light chain FR2

<400> SEQUENCE: 142
```

Trp Leu Leu Gln Arg Pro Gly Gln Ser Pro Lys Arg Leu Ile Tyr
1               5                   10                  15

<210> SEQ ID NO 143
<211> LENGTH: 7
<212> TYPE: PRT
<213> ORGANISM: Artificial Sequence
<220> FEATURE:
<223> OTHER INFORMATION: M3 light chain CDR2

<400> SEQUENCE: 143

Leu Val Ser Lys Leu Asp Ser
1               5

<210> SEQ ID NO 144
<211> LENGTH: 32
<212> TYPE: PRT
<213> ORGANISM: Artificial Sequence
<220> FEATURE:
<223> OTHER INFORMATION: M3 light chain FR3

<400> SEQUENCE: 144

Gly Val Pro Asp Arg Phe Thr Gly Ser Gly Ser Gly Thr Asp Phe Thr
1               5                   10                  15

Leu Lys Ile Ser Arg Val Glu Ala Glu Asp Leu Gly Leu Tyr Tyr Cys
            20                  25                  30

<210> SEQ ID NO 145
<211> LENGTH: 9
<212> TYPE: PRT
<213> ORGANISM: Artificial Sequence
<220> FEATURE:
<223> OTHER INFORMATION: M3 light chain CDR3

<400> SEQUENCE: 145

Val Gln Gly Ile His Phe Pro Arg Thr
1               5

<210> SEQ ID NO 146
<211> LENGTH: 10
<212> TYPE: PRT
<213> ORGANISM: Artificial Sequence
<220> FEATURE:
<223> OTHER INFORMATION: M3 light chain FR4

<400> SEQUENCE: 146

Phe Gly Gly Gly Thr Lys Leu Glu Ile Lys
1               5                   10

<210> SEQ ID NO 147
<211> LENGTH: 23
<212> TYPE: PRT
<213> ORGANISM: Artificial Sequence
<220> FEATURE:
<223> OTHER INFORMATION: M11 light chain FR1

<400> SEQUENCE: 147

Asp Ile Val Met Thr Gln Ser His Lys Phe Met Ser Thr Ser Val Gly
1               5                   10                  15

Asp Arg Val Ser Ile Thr Cys
            20

<210> SEQ ID NO 148
<211> LENGTH: 11
<212> TYPE: PRT

<213> ORGANISM: Artificial Sequence
<220> FEATURE:
<223> OTHER INFORMATION: M11 light chain CDR1

<400> SEQUENCE: 148

Lys Ala Ser Gln Asp Val Ser Thr Asn Val Ala
1               5                   10

<210> SEQ ID NO 149
<211> LENGTH: 15
<212> TYPE: PRT
<213> ORGANISM: Artificial Sequence
<220> FEATURE:
<223> OTHER INFORMATION: M11 light chain FR2

<400> SEQUENCE: 149

Trp Tyr Gln Gln Lys Pro Gly Gln Ser Pro Thr Leu Leu Ile Tyr
1               5                   10                  15

<210> SEQ ID NO 150
<211> LENGTH: 7
<212> TYPE: PRT
<213> ORGANISM: Artificial Sequence
<220> FEATURE:
<223> OTHER INFORMATION: M11 light chain CDR2

<400> SEQUENCE: 150

Trp Ala Ser Thr Arg His Thr
1               5

<210> SEQ ID NO 151
<211> LENGTH: 32
<212> TYPE: PRT
<213> ORGANISM: Artificial Sequence
<220> FEATURE:
<223> OTHER INFORMATION: M11 light chain FR3

<400> SEQUENCE: 151

Gly Val Pro Asp Arg Phe Thr Gly Ser Gly Ser Gly Thr Asp Tyr Thr
1               5                   10                  15

Leu Thr Ile Ser Ser Val Gln Ala Glu Asp Leu Ala Leu Tyr Tyr Cys
            20                  25                  30

<210> SEQ ID NO 152
<211> LENGTH: 9
<212> TYPE: PRT
<213> ORGANISM: Artificial Sequence
<220> FEATURE:
<223> OTHER INFORMATION: M11 light chain CDR3

<400> SEQUENCE: 152

Gln Gln His Tyr Ser Thr Pro Leu Thr
1               5

<210> SEQ ID NO 153
<211> LENGTH: 11
<212> TYPE: PRT
<213> ORGANISM: Artificial Sequence
<220> FEATURE:
<223> OTHER INFORMATION: M11 light chain FR4

<400> SEQUENCE: 153

Phe Gly Ala Gly Thr Lys Leu Glu Leu Arg Arg
1               5                   10

<210> SEQ ID NO 154

```
<211> LENGTH: 23
<212> TYPE: PRT
<213> ORGANISM: Artificial Sequence
<220> FEATURE:
<223> OTHER INFORMATION: M23 light chain FR1

<400> SEQUENCE: 154

Asp Ile Val Met Ser Gln Ser Pro Ser Ser Leu Ala Val Ser Ala Gly
1               5                   10                  15

Glu Lys Val Thr Met Thr Cys
            20

<210> SEQ ID NO 155
<211> LENGTH: 17
<212> TYPE: PRT
<213> ORGANISM: Artificial Sequence
<220> FEATURE:
<223> OTHER INFORMATION: M23 light chain CDR1

<400> SEQUENCE: 155

Lys Ser Ser Gln Ser Leu Leu Asn Ser Arg Ala Arg Lys Asn Tyr Leu
1               5                   10                  15

Ala

<210> SEQ ID NO 156
<211> LENGTH: 15
<212> TYPE: PRT
<213> ORGANISM: Artificial Sequence
<220> FEATURE:
<223> OTHER INFORMATION: M23 light chain FR2

<400> SEQUENCE: 156

Trp Tyr Gln Gln Lys Ala Gly Gln Ser Pro Lys Leu Leu Met Tyr
1               5                   10                  15

<210> SEQ ID NO 157
<211> LENGTH: 7
<212> TYPE: PRT
<213> ORGANISM: Artificial Sequence
<220> FEATURE:
<223> OTHER INFORMATION: M23 light chain CDR2

<400> SEQUENCE: 157

Trp Ala Ser Thr Arg Glu Ser
1               5

<210> SEQ ID NO 158
<211> LENGTH: 32
<212> TYPE: PRT
<213> ORGANISM: Artificial Sequence
<220> FEATURE:
<223> OTHER INFORMATION: M23 light chain FR3

<400> SEQUENCE: 158

Gly Val Pro Asp Arg Phe Thr Ala Ser Gly Ser Gly Thr Asp Phe Thr
1               5                   10                  15

Leu Thr Ile Ser Ser Val Gln Ala Glu Asp Leu Ala Val Phe Tyr Cys
            20                  25                  30

<210> SEQ ID NO 159
<211> LENGTH: 9
<212> TYPE: PRT
<213> ORGANISM: Artificial Sequence
<220> FEATURE:
<223> OTHER INFORMATION: M23 light chain CDR3
```

```
<400> SEQUENCE: 159

Lys Gln Ser Tyr Asn Leu Pro Trp Thr
1               5

<210> SEQ ID NO 160
<211> LENGTH: 11
<212> TYPE: PRT
<213> ORGANISM: Artificial Sequence
<220> FEATURE:
<223> OTHER INFORMATION: M23 light chain FR4

<400> SEQUENCE: 160

Phe Gly Gly Gly Thr Lys Leu Glu Ile Lys Arg
1               5                   10

<210> SEQ ID NO 161
<211> LENGTH: 23
<212> TYPE: PRT
<213> ORGANISM: Artificial Sequence
<220> FEATURE:
<223> OTHER INFORMATION: M29 light chain FR1

<400> SEQUENCE: 161

Asp Ile Val Met Ser Gln Ser Pro Ser Ser Leu Pro Val Ser Val Gly
1               5                   10                  15

Gln Lys Val Thr Met Thr Cys
            20

<210> SEQ ID NO 162
<211> LENGTH: 17
<212> TYPE: PRT
<213> ORGANISM: Artificial Sequence
<220> FEATURE:
<223> OTHER INFORMATION: M29 light chain CDR1

<400> SEQUENCE: 162

Lys Ser Ser Gln Ser Leu Leu Tyr Thr Ser Asn Gln Lys Asn Tyr Leu
1               5                   10                  15

Ala

<210> SEQ ID NO 163
<211> LENGTH: 15
<212> TYPE: PRT
<213> ORGANISM: Artificial Sequence
<220> FEATURE:
<223> OTHER INFORMATION: M29 light chain FR2

<400> SEQUENCE: 163

Trp Tyr Gln Gln Lys Pro Gly Gln Ser Pro Lys Leu Leu Ile Tyr
1               5                   10                  15

<210> SEQ ID NO 164
<211> LENGTH: 7
<212> TYPE: PRT
<213> ORGANISM: Artificial Sequence
<220> FEATURE:
<223> OTHER INFORMATION: M29 light chain CDR2

<400> SEQUENCE: 164

Trp Ala Ser Thr Arg Glu Ser
1               5

<210> SEQ ID NO 165
<211> LENGTH: 32
<212> TYPE: PRT
```

```
<213> ORGANISM: Artificial Sequence
<220> FEATURE:
<223> OTHER INFORMATION: M29 light chain FR3

<400> SEQUENCE: 165

Gly Val Pro Asp Arg Phe Thr Gly Ser Gly Ser Gly Thr Asp Phe Thr
1               5                   10                  15

Leu Thr Ile Ser Ser Val Lys Ala Glu Asp Leu Ala Ile Tyr Tyr Cys
            20                  25                  30

<210> SEQ ID NO 166
<211> LENGTH: 8
<212> TYPE: PRT
<213> ORGANISM: Artificial Sequence
<220> FEATURE:
<223> OTHER INFORMATION: M29 light chain CDR3

<400> SEQUENCE: 166

Gln Gln Tyr Tyr Arg Tyr His Thr
1               5

<210> SEQ ID NO 167
<211> LENGTH: 10
<212> TYPE: PRT
<213> ORGANISM: Artificial Sequence
<220> FEATURE:
<223> OTHER INFORMATION: M29 light chain FR4

<400> SEQUENCE: 167

Phe Gly Gly Gly Thr Arg Leu Glu Ile Lys
1               5                   10

<210> SEQ ID NO 168
<211> LENGTH: 23
<212> TYPE: PRT
<213> ORGANISM: Artificial Sequence
<220> FEATURE:
<223> OTHER INFORMATION: M48 light chain FR1

<400> SEQUENCE: 168

Asp Ile Val Leu Thr Gln Ser Pro Ala Thr Leu Ser Val Thr Pro Gly
1               5                   10                  15

Glu Ser Val Ser Leu Ser Cys
            20

<210> SEQ ID NO 169
<211> LENGTH: 11
<212> TYPE: PRT
<213> ORGANISM: Artificial Sequence
<220> FEATURE:
<223> OTHER INFORMATION: M48 light chain CDR1

<400> SEQUENCE: 169

Arg Ala Ser Gln Gly Ile Ser Thr Ser Ile His
1               5                   10

<210> SEQ ID NO 170
<211> LENGTH: 15
<212> TYPE: PRT
<213> ORGANISM: Artificial Sequence
<220> FEATURE:
<223> OTHER INFORMATION: M48 light chain FR2

<400> SEQUENCE: 170

Trp Tyr Gln Gln Lys Ser Asn Glu Ser Pro Arg Leu Leu Ile Arg
1               5                   10                  15
```

<210> SEQ ID NO 171
<211> LENGTH: 7
<212> TYPE: PRT
<213> ORGANISM: Artificial Sequence
<220> FEATURE:
<223> OTHER INFORMATION: M48 light chain CDR2

<400> SEQUENCE: 171

Tyr Ala Ser Gln Ser Ile Ser
1               5

<210> SEQ ID NO 172
<211> LENGTH: 32
<212> TYPE: PRT
<213> ORGANISM: Artificial Sequence
<220> FEATURE:
<223> OTHER INFORMATION: M48 light chain FR3

<400> SEQUENCE: 172

Arg Ile Pro Ser Arg Phe Ser Gly Ser Gly Ser Gly Thr Asp Phe Thr
1               5                   10                  15

Leu Thr Ile Asn Gly Val Glu Ser Glu Asp Leu Ser Val Tyr Tyr Cys
            20                  25                  30

<210> SEQ ID NO 173
<211> LENGTH: 9
<212> TYPE: PRT
<213> ORGANISM: Artificial Sequence
<220> FEATURE:
<223> OTHER INFORMATION: M48 light chain CDR3

<400> SEQUENCE: 173

Gln Gln Ser Tyr Asn Leu Pro Leu Thr
1               5

<210> SEQ ID NO 174
<211> LENGTH: 9
<212> TYPE: PRT
<213> ORGANISM: Artificial Sequence
<220> FEATURE:
<223> OTHER INFORMATION: M48 light chain FR4

<400> SEQUENCE: 174

Phe Gly Ser Gly Thr Lys Leu Glu Ile
1               5

<210> SEQ ID NO 175
<211> LENGTH: 23
<212> TYPE: PRT
<213> ORGANISM: Artificial Sequence
<220> FEATURE:
<223> OTHER INFORMATION: R2 light chain FR1

<400> SEQUENCE: 175

Asp Ile Val Leu Thr Gln Ser Pro Ala Thr Leu Ser Val Thr Pro Gly
1               5                   10                  15

Glu Ser Val Ser Leu Ser Cys
            20

<210> SEQ ID NO 176
<211> LENGTH: 11
<212> TYPE: PRT
<213> ORGANISM: Artificial Sequence
<220> FEATURE:
<223> OTHER INFORMATION: R2 light chain CDR1

<400> SEQUENCE: 176

Arg Ala Ser Gln Gly Ile Ser Thr Ser Ile His
1               5                   10

<210> SEQ ID NO 177
<211> LENGTH: 15
<212> TYPE: PRT
<213> ORGANISM: Artificial Sequence
<220> FEATURE:
<223> OTHER INFORMATION: R2 light chain FR2

<400> SEQUENCE: 177

Trp Tyr Gln Gln Lys Ser Asn Glu Ser Pro Arg Leu Leu Ile Arg
1               5                   10                  15

<210> SEQ ID NO 178
<211> LENGTH: 7
<212> TYPE: PRT
<213> ORGANISM: Artificial Sequence
<220> FEATURE:
<223> OTHER INFORMATION: R2 light chain CDR2

<400> SEQUENCE: 178

Tyr Ala Ser Gln Ser Ile Ser
1               5

<210> SEQ ID NO 179
<211> LENGTH: 32
<212> TYPE: PRT
<213> ORGANISM: Artificial Sequence
<220> FEATURE:
<223> OTHER INFORMATION: R2 light chain FR3

<400> SEQUENCE: 179

Arg Ile Pro Ser Arg Phe Ser Gly Ser Gly Ser Gly Thr Asp Phe Thr
1               5                   10                  15
Leu Thr Ile Asn Gly Val Glu Ser Glu Asp Leu Ser Val Tyr Tyr Cys
            20                  25                  30

<210> SEQ ID NO 180
<211> LENGTH: 9
<212> TYPE: PRT
<213> ORGANISM: Artificial Sequence
<220> FEATURE:
<223> OTHER INFORMATION: R2 light chain CDR3

<400> SEQUENCE: 180

Gln Gln Ser Tyr Asn Leu Pro Leu Thr
1               5

<210> SEQ ID NO 181
<211> LENGTH: 9
<212> TYPE: PRT
<213> ORGANISM: Artificial Sequence
<220> FEATURE:
<223> OTHER INFORMATION: R2 light chain FR4

<400> SEQUENCE: 181

Phe Gly Ser Gly Thr Lys Leu Glu Ile
1               5

<210> SEQ ID NO 182
<211> LENGTH: 23
<212> TYPE: PRT
<213> ORGANISM: Artificial Sequence

```
<220> FEATURE:
<223> OTHER INFORMATION: R3 light chain FR1

<400> SEQUENCE: 182

Asp Ile Val Met Thr Gln Ser Pro Ser Ser Leu Ala Val Ser Ala Gly
1               5                   10                  15

Glu Thr Val Thr Met Asn Cys
            20

<210> SEQ ID NO 183
<211> LENGTH: 17
<212> TYPE: PRT
<213> ORGANISM: Artificial Sequence
<220> FEATURE:
<223> OTHER INFORMATION: R3 light chain CDR1

<400> SEQUENCE: 183

Arg Ser Ser Gln Ser Leu Phe Ser Ser Gly Asp Gln Lys Lys Phe Leu
1               5                   10                  15

Ala

<210> SEQ ID NO 184
<211> LENGTH: 15
<212> TYPE: PRT
<213> ORGANISM: Artificial Sequence
<220> FEATURE:
<223> OTHER INFORMATION: R3 light chain FR2

<400> SEQUENCE: 184

Trp Tyr Gln Gln Lys Pro Gly Gln Ser Pro Lys Leu Leu Ile Ser
1               5                   10                  15

<210> SEQ ID NO 185
<211> LENGTH: 7
<212> TYPE: PRT
<213> ORGANISM: Artificial Sequence
<220> FEATURE:
<223> OTHER INFORMATION: R3 light chain CDR2

<400> SEQUENCE: 185

Leu Ala Ser Thr Arg Glu Ser
1               5

<210> SEQ ID NO 186
<211> LENGTH: 32
<212> TYPE: PRT
<213> ORGANISM: Artificial Sequence
<220> FEATURE:
<223> OTHER INFORMATION: R3 light chain FR3

<400> SEQUENCE: 186

Gly Val Pro Asp Arg Phe Ile Gly Ser Gly Ser Gly Thr Asp Phe Thr
1               5                   10                  15

Leu Thr Ile Asn Asn Met Gln Ala Glu Asp Leu Ala Ile Tyr Tyr Cys
            20                  25                  30

<210> SEQ ID NO 187
<211> LENGTH: 9
<212> TYPE: PRT
<213> ORGANISM: Artificial Sequence
<220> FEATURE:
<223> OTHER INFORMATION: R3 light chain CDR3

<400> SEQUENCE: 187

Gln Gln His Tyr Asp Ile Pro Tyr Thr
```

<210> SEQ ID NO 188
<211> LENGTH: 9
<212> TYPE: PRT
<213> ORGANISM: Artificial Sequence
<220> FEATURE:
<223> OTHER INFORMATION: R3 light chain FR4

<400> SEQUENCE: 188

Phe Gly Ala Gly Thr Lys Leu Glu Leu
1               5

<210> SEQ ID NO 189
<211> LENGTH: 23
<212> TYPE: PRT
<213> ORGANISM: Artificial Sequence
<220> FEATURE:
<223> OTHER INFORMATION: R8 light chain FR1

<400> SEQUENCE: 189

Asp Ile Val Met Thr Gln Ser Pro Ser Phe Leu Ala Val Ser Val Gly
1               5                   10                  15

Glu Thr Val Thr Ile Asn Cys
            20

<210> SEQ ID NO 190
<211> LENGTH: 17
<212> TYPE: PRT
<213> ORGANISM: Artificial Sequence
<220> FEATURE:
<223> OTHER INFORMATION: R8 light chain CDR1

<400> SEQUENCE: 190

Lys Ser Ser Gln Ser Phe Leu Ser Ser Gly Asn Gln Glu Asn Tyr Leu
1               5                   10                  15

Ala

<210> SEQ ID NO 191
<211> LENGTH: 15
<212> TYPE: PRT
<213> ORGANISM: Artificial Sequence
<220> FEATURE:
<223> OTHER INFORMATION: R8 light chain FR2

<400> SEQUENCE: 191

Trp Tyr Gln Gln Lys Pro Gly Gln Ser Pro Lys Leu Leu Ile His
1               5                   10                  15

<210> SEQ ID NO 192
<211> LENGTH: 7
<212> TYPE: PRT
<213> ORGANISM: Artificial Sequence
<220> FEATURE:
<223> OTHER INFORMATION: R8 light chain CDR2

<400> SEQUENCE: 192

Leu Ala Ser Thr Arg Glu Ser
1               5

<210> SEQ ID NO 193
<211> LENGTH: 32
<212> TYPE: PRT
<213> ORGANISM: Artificial Sequence
<220> FEATURE:
<223> OTHER INFORMATION: R8 light chain FR3

<400> SEQUENCE: 193

Gly Val Pro Asp Arg Phe Ile Gly Ser Gly Ser Gly Thr Asp Phe Thr
1               5                   10                  15

Leu Thr Ile Ser Ser Met Gln Ala Glu Asp Val Ala Ile Tyr Tyr Cys
            20                  25                  30

<210> SEQ ID NO 194
<211> LENGTH: 9
<212> TYPE: PRT
<213> ORGANISM: Artificial Sequence
<220> FEATURE:
<223> OTHER INFORMATION: R8 light chain CDR3

<400> SEQUENCE: 194

Gln Gln His Tyr Asp Ile Pro Tyr Thr
1               5

<210> SEQ ID NO 195
<211> LENGTH: 9
<212> TYPE: PRT
<213> ORGANISM: Artificial Sequence
<220> FEATURE:
<223> OTHER INFORMATION: R8 light chain FR4

<400> SEQUENCE: 195

Phe Gly Ala Gly Thr Lys Leu Glu Leu
1               5

<210> SEQ ID NO 196
<211> LENGTH: 23
<212> TYPE: PRT
<213> ORGANISM: Artificial Sequence
<220> FEATURE:
<223> OTHER INFORMATION: R9 light chain FR1

<400> SEQUENCE: 196

Asp Ile Val Met Thr Gln Thr Pro Ser Ser Gln Ala Val Ser Ala Gly
1               5                   10                  15

Glu Lys Val Thr Met Ser Cys
            20

<210> SEQ ID NO 197
<211> LENGTH: 17
<212> TYPE: PRT
<213> ORGANISM: Artificial Sequence
<220> FEATURE:
<223> OTHER INFORMATION: R9 light chain CDR1

<400> SEQUENCE: 197

Lys Ser Ser Gln Ser Leu Leu Tyr Ser Gly Asp Gln Lys Asn Tyr Leu
1               5                   10                  15

Ala

<210> SEQ ID NO 198
<211> LENGTH: 15
<212> TYPE: PRT
<213> ORGANISM: Artificial Sequence
<220> FEATURE:
<223> OTHER INFORMATION: R9 light chain FR2

<400> SEQUENCE: 198

Trp Tyr Gln Gln Lys Pro Gly Gln Ser Pro Lys Leu Leu Ile Tyr
1               5                   10                  15

<210> SEQ ID NO 199
<211> LENGTH: 7
<212> TYPE: PRT
<213> ORGANISM: Artificial Sequence
<220> FEATURE:
<223> OTHER INFORMATION: R9 light chain CDR2

<400> SEQUENCE: 199

Leu Thr Ser Thr Arg Glu Ser
1               5

<210> SEQ ID NO 200
<211> LENGTH: 32
<212> TYPE: PRT
<213> ORGANISM: Artificial Sequence
<220> FEATURE:
<223> OTHER INFORMATION: R9 light chain FR3

<400> SEQUENCE: 200

Gly Val Pro Asp Arg Phe Ile Gly Ser Gly Ser Gly Thr Asp Phe Thr
1               5                   10                  15

Leu Thr Ile Ser Ser Val Gln Ala Glu Asp Leu Ala Asp Tyr Tyr Cys
            20                  25                  30

<210> SEQ ID NO 201
<211> LENGTH: 9
<212> TYPE: PRT
<213> ORGANISM: Artificial Sequence
<220> FEATURE:
<223> OTHER INFORMATION: R9 light chain CDR3

<400> SEQUENCE: 201

Gln Gln His Tyr Ser Tyr Pro Leu Thr
1               5

<210> SEQ ID NO 202
<211> LENGTH: 9
<212> TYPE: PRT
<213> ORGANISM: Artificial Sequence
<220> FEATURE:
<223> OTHER INFORMATION: R9 light chain FR4

<400> SEQUENCE: 202

Phe Gly Ser Gly Thr Lys Leu Glu Ile
1               5

<210> SEQ ID NO 203
<211> LENGTH: 23
<212> TYPE: PRT
<213> ORGANISM: Artificial Sequence
<220> FEATURE:
<223> OTHER INFORMATION: R11 light chain FR1

<400> SEQUENCE: 203

Asp Val Val Met Thr Gln Thr Pro Val Ser Leu Val Ser Leu Gly
1               5                   10                  15

Gly Gln Thr Ser Ile Ser Cys
            20

<210> SEQ ID NO 204
<211> LENGTH: 16
<212> TYPE: PRT
<213> ORGANISM: Artificial Sequence
<220> FEATURE:
<223> OTHER INFORMATION: R11 light chain CDR1

```
<400> SEQUENCE: 204

Arg Ser Ser Gln Ser Leu Phe His Ser Asp Gly Asn Thr Tyr Leu Tyr
1               5                   10                  15

<210> SEQ ID NO 205
<211> LENGTH: 15
<212> TYPE: PRT
<213> ORGANISM: Artificial Sequence
<220> FEATURE:
<223> OTHER INFORMATION: R11 light chain FR2

<400> SEQUENCE: 205

Trp Tyr Leu Arg Lys Pro Gly Gln Ser Pro Gln Leu Leu Ile Tyr
1               5                   10                  15

<210> SEQ ID NO 206
<211> LENGTH: 7
<212> TYPE: PRT
<213> ORGANISM: Artificial Sequence
<220> FEATURE:
<223> OTHER INFORMATION: R11 light chain CDR2

<400> SEQUENCE: 206

Lys Val Ser Asn Arg Phe Ser
1               5

<210> SEQ ID NO 207
<211> LENGTH: 32
<212> TYPE: PRT
<213> ORGANISM: Artificial Sequence
<220> FEATURE:
<223> OTHER INFORMATION: R11 light chain FR3

<400> SEQUENCE: 207

Gly Val Pro Asp Arg Phe Ser Gly Ser Gly Ser Gly Thr Asp Phe Thr
1               5                   10                  15

Leu Lys Ile Ser Arg Val Glu Pro Glu Asp Leu Gly Leu Tyr Tyr Cys
            20                  25                  30

<210> SEQ ID NO 208
<211> LENGTH: 9
<212> TYPE: PRT
<213> ORGANISM: Artificial Sequence
<220> FEATURE:
<223> OTHER INFORMATION: R11 light chain CDR3

<400> SEQUENCE: 208

Tyr Gln Gly Thr His Tyr Pro Pro Thr
1               5

<210> SEQ ID NO 209
<211> LENGTH: 8
<212> TYPE: PRT
<213> ORGANISM: Artificial Sequence
<220> FEATURE:
<223> OTHER INFORMATION: R11 light chain FR4

<400> SEQUENCE: 209

Phe Gly Ser Gly Thr Lys Leu Glu
1               5

<210> SEQ ID NO 210
<211> LENGTH: 23
<212> TYPE: PRT
<213> ORGANISM: Artificial Sequence
<220> FEATURE:
```

```
<223> OTHER INFORMATION: R14 light chain FR1

<400> SEQUENCE: 210

Asp Ile Leu Met Thr Gln Thr Pro Ser Ser Gln Ala Val Ser Ala Gly
1               5                   10                  15

Glu Lys Val Thr Val Ser Cys
            20

<210> SEQ ID NO 211
<211> LENGTH: 17
<212> TYPE: PRT
<213> ORGANISM: Artificial Sequence
<220> FEATURE:
<223> OTHER INFORMATION: R14 light chain CDR1

<400> SEQUENCE: 211

Lys Ser Ser Gln Ser Leu Leu Tyr Ser Gly Asp Gln Lys Ser Tyr Leu
1               5                   10                  15

Ala

<210> SEQ ID NO 212
<211> LENGTH: 15
<212> TYPE: PRT
<213> ORGANISM: Artificial Sequence
<220> FEATURE:
<223> OTHER INFORMATION: R14 light chain FR2

<400> SEQUENCE: 212

Trp Tyr Gln Gln Lys Pro Gly Gln Ser Pro Lys Leu Leu Ile Tyr
1               5                   10                  15

<210> SEQ ID NO 213
<211> LENGTH: 7
<212> TYPE: PRT
<213> ORGANISM: Artificial Sequence
<220> FEATURE:
<223> OTHER INFORMATION: R14 light chain CDR2

<400> SEQUENCE: 213

Leu Ala Ser Thr Arg Lys Ser
1               5

<210> SEQ ID NO 214
<211> LENGTH: 32
<212> TYPE: PRT
<213> ORGANISM: Artificial Sequence
<220> FEATURE:
<223> OTHER INFORMATION: R14 light chain FR3

<400> SEQUENCE: 214

Gly Val Pro Asp Arg Phe Ile Gly Ser Gly Ser Gly Thr Asp Phe Thr
1               5                   10                  15

Leu Thr Ile Ser Ser Val Gln Ala Glu Asp Leu Ala Asp Tyr Tyr Cys
            20                  25                  30

<210> SEQ ID NO 215
<211> LENGTH: 9
<212> TYPE: PRT
<213> ORGANISM: Artificial Sequence
<220> FEATURE:
<223> OTHER INFORMATION: R14 light chain CDR3

<400> SEQUENCE: 215

Gln Gln His Tyr Thr Tyr Pro Leu Thr
1               5
```

```
<210> SEQ ID NO 216
<211> LENGTH: 9
<212> TYPE: PRT
<213> ORGANISM: Artificial Sequence
<220> FEATURE:
<223> OTHER INFORMATION: R14 light chain FR4

<400> SEQUENCE: 216

Phe Gly Ser Gly Thr Lys Leu Glu Ile
1               5

<210> SEQ ID NO 217
<211> LENGTH: 23
<212> TYPE: PRT
<213> ORGANISM: Artificial Sequence
<220> FEATURE:
<223> OTHER INFORMATION: R20 light chain FR1

<400> SEQUENCE: 217

Asp Ile Val Met Thr Gln Ser Pro Ser Ser Leu Ala Val Ser Ala Gly
1               5                   10                  15

Glu Thr Val Thr Ile Asn Cys
            20

<210> SEQ ID NO 218
<211> LENGTH: 17
<212> TYPE: PRT
<213> ORGANISM: Artificial Sequence
<220> FEATURE:
<223> OTHER INFORMATION: R20 light chain CDR1

<400> SEQUENCE: 218

Lys Ser Ser Gln Ser Leu Leu Phe Ser Gly Asp Gln Glu Asn His Leu
1               5                   10                  15

Ala

<210> SEQ ID NO 219
<211> LENGTH: 15
<212> TYPE: PRT
<213> ORGANISM: Artificial Sequence
<220> FEATURE:
<223> OTHER INFORMATION: R20 light chain FR2

<400> SEQUENCE: 219

Trp Tyr Gln Gln Lys Ala Gly Gln Ser Ala Lys Leu Leu Ile Tyr
1               5                   10                  15

<210> SEQ ID NO 220
<211> LENGTH: 7
<212> TYPE: PRT
<213> ORGANISM: Artificial Sequence
<220> FEATURE:
<223> OTHER INFORMATION: R20 light chain CDR2

<400> SEQUENCE: 220

Trp Ala Ser Thr Arg Glu Ser
1               5

<210> SEQ ID NO 221
<211> LENGTH: 32
<212> TYPE: PRT
<213> ORGANISM: Artificial Sequence
<220> FEATURE:
<223> OTHER INFORMATION: R20 light chain FR3
```

```
<400> SEQUENCE: 221

Gly Val Pro Asp Arg Phe Ile Gly Ser Gly Ser Gly Ala Asp Phe Thr
1               5                   10                  15

Leu Thr Ile Ser Ser Met Gln Ala Glu Asp Arg Ala Thr Tyr Tyr Cys
            20                  25                  30

<210> SEQ ID NO 222
<211> LENGTH: 9
<212> TYPE: PRT
<213> ORGANISM: Artificial Sequence
<220> FEATURE:
<223> OTHER INFORMATION: R20 light chain CDR3

<400> SEQUENCE: 222

Gln Gln Asn Tyr Asp Ile Pro Tyr Thr
1               5

<210> SEQ ID NO 223
<211> LENGTH: 9
<212> TYPE: PRT
<213> ORGANISM: Artificial Sequence
<220> FEATURE:
<223> OTHER INFORMATION: R20 light chain FR4

<400> SEQUENCE: 223

Phe Gly Ala Gly Thr Lys Leu Glu Leu
1               5

<210> SEQ ID NO 224
<211> LENGTH: 23
<212> TYPE: PRT
<213> ORGANISM: Artificial Sequence
<220> FEATURE:
<223> OTHER INFORMATION: R28 light chain FR1

<400> SEQUENCE: 224

Asp Ile Val Met Thr Gln Ser Pro Ser Ser Leu Ala Val Ser Ala Gly
1               5                   10                  15

Glu Thr Val Thr Ile Asn Cys
            20

<210> SEQ ID NO 225
<211> LENGTH: 17
<212> TYPE: PRT
<213> ORGANISM: Artificial Sequence
<220> FEATURE:
<223> OTHER INFORMATION: R28 light chain CDR1

<400> SEQUENCE: 225

Lys Ser Ser Arg Ser Leu Phe Ser Ser Gly Tyr Gln Glu Asn Tyr Leu
1               5                   10                  15

Ala

<210> SEQ ID NO 226
<211> LENGTH: 15
<212> TYPE: PRT
<213> ORGANISM: Artificial Sequence
<220> FEATURE:
<223> OTHER INFORMATION: R28 light chain FR2

<400> SEQUENCE: 226

Trp Tyr Gln Gln Lys Pro Gly Gln Ser Pro Lys Met Leu Ile Tyr
1               5                   10                  15
```

```
<210> SEQ ID NO 227
<211> LENGTH: 7
<212> TYPE: PRT
<213> ORGANISM: Artificial Sequence
<220> FEATURE:
<223> OTHER INFORMATION: R28 light chain CDR2

<400> SEQUENCE: 227

Leu Ala Ser Thr Arg Glu Ser
1               5

<210> SEQ ID NO 228
<211> LENGTH: 32
<212> TYPE: PRT
<213> ORGANISM: Artificial Sequence
<220> FEATURE:
<223> OTHER INFORMATION: R28 light chain FR3

<400> SEQUENCE: 228

Gly Val Pro Asp Arg Phe Ile Gly Ser Gly Ser Gly Thr Asp Phe Thr
1               5                   10                  15

Leu Thr Ile Asn Thr Leu Gln Ala Glu Asp Leu Ala Ile Tyr Tyr Cys
            20                  25                  30

<210> SEQ ID NO 229
<211> LENGTH: 9
<212> TYPE: PRT
<213> ORGANISM: Artificial Sequence
<220> FEATURE:
<223> OTHER INFORMATION: R28 light chain CDR3

<400> SEQUENCE: 229

Gln Gln His Tyr Asp Ile Pro Tyr Thr
1               5

<210> SEQ ID NO 230
<211> LENGTH: 9
<212> TYPE: PRT
<213> ORGANISM: Artificial Sequence
<220> FEATURE:
<223> OTHER INFORMATION: R28 light chain FR4

<400> SEQUENCE: 230

Phe Gly Ala Gly Thr Lys Leu Glu Leu
1               5
```

ANTI-CLDN-5 ANTIBODY, AND DRUG CONTAINING SAID ANTIBODY

TECHNICAL FIELD

The present invention relates to an anti-CLDN-5 antibody and a drug containing the antibody. More specifically, the present invention relates to an antibody recognizing an extracellular domain of CLDN-5, a drug for controlling the blood-brain barrier, and the like.

BACKGROUND ART

The blood-brain barrier is a mechanism which restricts the exchange of materials between blood and brain, and plays a key role for protecting brain from the intrusion of foreign substances. On the other hand, because the blood-brain barrier hinders an intravenously administered medication from moving to brain, the barrier is a big obstacle in developing cures for brain diseases. The blood-brain barrier performs its function by extremely tight junctions between brain capillary endothelial cells, and is greatly different from the space between capillary endothelial cells of other organs that allows the permeation of materials. Hitherto, as a methodology for transporting a medication through the intercellular space by controlling the tight junction restricting material transport, a method of administering a mannitol hypertonic saline through carotid has been devised. However, this method causes serious side effects because the method changes the physical form of cells due to cellular dehydration and destructs the tight junction. Therefore, there is a demand for developing a novel technique which specifically controls only the tight junction.

CLDN family molecules play a key role in forming the tight junction between cells such as epithelial cells or vascular endothelial cells. The CLDN family consists of 27 kinds of 4-transmembrane protein members and has 2 extracellular loops (first and second extracellular loops from the N-terminal side). The interaction between these cells contributes to the formation of the tight junction. The type (compositional ratio) or the amount of expressed CLDN family molecules varies between tissues, and the variation results in a tissue-specific tight junction and a barrier function. Particularly, in a tight junction between cerebrovascular endothelial cells, CLDN-5 is highly expressed and exerts a great influence on the function of the blood-brain barrier. In reality, in a CLDN-5-deficient mouse, the blood-brain barrier loses its function and allows the permeation of materials having a molecular weight equal to or smaller than 1.000. In addition, it has been reported that in an experiment of intravenously administering CLDN-5 siRNA to a mouse, the expression of CLDN-5 in cerebrovascular endothelial cells is reduced, and accordingly, materials having a molecular weight equal to or smaller than 1,000 are allowed to move into brain, and no serious side effect occurs (Non-Patent Literature 1). Based on these finding, the control of the function of CLDN-5 is expected to be a novel strategy for intracerebral medication delivery through an intercellular space.

Hitherto, in order to inhibit the barrier function resulting from CLDN-5, several CLDN-5 interacting molecules have been prepared. For example, it has been reported that in a case where a peptide (consisting of approximately 20 amino acids) derived from a partial sequence of the first extracellular loop of CLDN-1 is used, it is possible to control the barrier of mouse brain capillary endothelial cells through the interaction between CLDN-1 and CLDN-5 (Non-Patent Literature 2). Furthermore, there is a report regarding a case where a CLDN-5-binding molecule is created by introducing a mutation into the C-terminal of *Clostridium perfringens* enterotoxin known as a molecule that binds to CLDN-3 and CLDN-4 and has a high barrier control activity (Non-Patent Literature 3). However, unfortunately, these molecules exhibit low binding specificity to CLDN-5 and bind to other CLDN molecules as well. Therefore, from the viewpoint of enhancing the barrier control activity and reducing side effects, it is considered that the development of a blood-brain barrier control technique by using these molecules may be extremely difficult. Although there is another report regarding peptides and antibodies controlling cell adhesion of CLDN family molecules, the report does not present experimental data relating to the control of the blood-brain barrier by using an anti-CLDN-5 antibody (Patent Literature 1). In this way, there is still no molecule which specifically interacts with CLDN-5 and controls the function thereof.

CITATION LIST

Non-Patent Literature

Non-Patent Literature 1: Matthew Campbell, Anna-Sophia Kiang, Paul F. Kenna, Christian Kerskens, Christoph Blau, Laurence O'Dwyer, Amanda Tivnan, Julie Anne Kelly, Brenda Brankin, Gwyneth-Jane Farrar, Peter Humphries. RNAi-mediated reversible opening of the blood-brain barrier. The journal of gene medicine 10 (2008) 930-947.

Non-Patent Literature 1 Christian Staat, Caroline Coisne, Sebastian Dabrowski, Svetlana M. Stamatovic, Anuska V. Andjelkovic, Hartwig Wolburg, Britta Engelhardt, Ingolf E. Blasig. Mode of action of claudin peptidomimetics in the transient opening of cellular tight junction barriers. Biomaterials 54 (2015) 9-20.

Non-Patent Literature 3: Jonas Protze, Miriam Eichner, Anna Piontek, Stefan Dinter, JanRossa, Kinga Grazyna Blecharz, Peter Vajkoczy, Joerg Piontek, Gerd Krause. Directed structural modification of *Clostridium perfringens* enterotoxin to enhance binding to claudin-5. Cellular and Molecular Life Sciences 72 (2015) 1417-1432

Patent Literature

Patent Literature 1: JP2003-524384A

SUMMARY OF INVENTION

Technical Problem

An object of the present invention is to provide a novel molecule which exhibits high CLDN-5 specificity and recognizes an extracellular domain of CLDN-5. Another object of the present invention is to provide a CLDN-5 expression cell detection technique and a blood-brain barrier control technique using the molecule.

Solution to Problem

There is still no case where a binding molecule exhibiting high specificity to CLDN-5 is prepared and a useful activity thereof that is preferably a blood-brain barrier control activity thereof is experimentally proven, for the following reason for example. That is, because CLDN-5 is a membrane protein, it is difficult to purify the protein from the viewpoint of solubility or aggregating properties, and the quality-amount of the obtained protein are insufficient for the protein to be a screening material or an immunogen used in a phage display technique. In order to solve the above problem, the inventors of the present invention conducted an intensive study. As a result, the inventors have succeeded in creating an antibody recognizing a domain in an extracellular domain of the CLDN-5 protein (in the present specification, the antibody will be described as "antibody according to an embodiment of the present invention", "CLDN-5 extracellular domain antibody", or the like as well). Furthermore, surprisingly, it has been found that the antibody according to an embodiment of the present invention has an activity of opening the junction between cerebrovascular endothelial cells, that is, a blood-brain barrier control activity. As a result of further continuing the study based on the finding, the inventors have accomplished the present invention.

The present invention includes the following aspects as an embodiment:

1. An antibody that specifically recognizes a three-dimensional structure or a primary structure of an extracellular domain of a Claudio-5 protein.

2. The antibody described in 1 that binds to none of extracellular domains of a Claudin-1 protein, a Claudin-2 protein, a Claudin-3 protein, a Claudin-4 protein, a Claudin-6 protein, and a Claudin-7 protein.

3. The antibody described in 1 or 2 that specifically recognizes a domain ranging from the $28^{th}$ amino acid (proline) to the $80^{th}$ amino acid (alanine) from the N-terminal in a human CLDN-5 protein consisting of an amino acid sequence represented by SEQ ID NO: 27.

4. The antibody described in any one of 1 to 3 of which a binding capacity to a protein 1-1-5 consisting of an amino acid sequence represented by SEQ ID NO: 45 is equal to or lower than 1/5 of a binding capacity thereof to a human Claudin-5 protein consisting of an amino acid sequence represented by SEQ ID NO: 27, wherein the protein 1-1-5 is the one where a first extracellular loop of the human Claudin-5 protein is substituted with a first loop of a human Claudin-1 protein.

5. The antibody described in 4 of which a binding capacity to a human Claudin-5 protein point mutant D68E consisting of an amino acid sequence represented by SEQ ID NO: 41 is equal to or lower than 1/5 of a binding capacity thereof to a human Claudin-5 protein consisting of an amino acid sequence represented by SEQ ID NO: 27.

6. The antibody described in 1 or 2 that specifically recognizes a domain ranging from the $147^{th}$ amino acid (phenylalanine) to the $163^{rd}$ amino acid (alanine) from the N-terminal in a human CLDN-5 protein consisting of an amino acid sequence represented by SEQ ID NO: 27.

7. The antibody described in any one of 1, 2, or 6 of which a binding capacity to a protein 5-5-1 consisting of an amino acid sequence represented by SEQ ID NO: 48 is equal to or lower than 1/5 of a binding capacity thereof to a human Claudin-5 protein consisting of an amino acid sequence represented by SEQ ID NO: 27, wherein the protein 5-5-1 is the one where a second extracellular loop of the human Claudin-5 protein is substituted with a second loop of a human Claudin-1 protein.

8. The antibody described in 7 of which a binding capacity to a human Claudin-5 protein point mutant S151T consisting of an amino acid sequence represented by SEQ ID NO: 43 is equal to or lower than 1/5 of a binding capacity thereof to a human Claudin-5 protein consisting of an amino acid sequence represented by SEQ ID NO: 27.

9. The antibody described in 1 or 2 that specifically recognizes a three-dimensional structure formed of a domain ranging from the $28^{th}$ amino acid (proline) to the $80^{th}$ amino acid (alanine) from the N-terminal and a domain ranging from the $147^{th}$ amino acid (phenylalanine) to the $163^{rd}$ amino acid (alanine) from the N-terminal in a human CLDN-5 protein consisting of an amino acid sequence represented by SEQ ID NO: 27.

10. The antibody described in any one of 1, 2, or 9 of which a binding capacity to a mutant TM consisting of an amino acid sequence represented by SEQ ID NO: 44 is equal to or lower than 1/5 of a binding capacity thereof to a human Claudin-5 protein consisting of an amino acid sequence represented by SEQ ID NO: 27, wherein the mutant TM is the one where the human Claudin-5 protein except for an extracellular domain thereof is substituted with a mouse Claudin-5 protein.

11. The antibody described in any one of 1 to 10 that is selected from the group consisting of the following antibodies:

(I) antibody I which contains a heavy chain variable region containing a heavy chain CDR1 having an amino acid sequence represented by SEQ ID NO: 106 or an amino acid sequence sharing identity equal to or higher than 95% with the amino acid sequence represented by SEQ ID NO: 106, a heavy chain CDR2 having an amino acid sequence represented by SEQ ID NO: 108 or an amino acid sequence sharing identity equal to or higher than 95% with the amino acid sequence represented by SEQ ID NO: 108, and a heavy chain CDR3 having an amino acid sequence represented by SEQ ID NO: 110 or an amino acid sequence sharing identity equal to or higher than 95% with the amino acid sequence represented by SEQ ID NO: 110 and/or a light chain variable region containing a light chain CDR1 having an amino acid sequence represented by SEQ ID NO: 197 or an amino acid sequence sharing identity equal to or higher than 95% with the amino acid sequence represented by SEQ ID NO: 197, a light chain CDR2 having an amino acid sequence represented by SEQ ID NO: 199 or an amino acid sequence sharing identity equal to or higher than 95% with the amino acid sequence represented by SEQ ID NO: 199, and a light chain CDR3 having an amino acid sequence represented by SEQ ID NO: 201 or an amino acid sequence sharing identity equal to or higher than 95% with the amino acid sequence represented by SEQ ID NO: 201;

(E) antibody E which contains a heavy chain variable region containing a heavy chain CDR1 having an amino acid sequence represented by SEQ ID NO: 78 or an amino acid sequence sharing identity equal to or higher than 95% with the amino acid sequence represented by SEQ ID NO: 78, a heavy chain CDR2 having an amino acid sequence represented by SEQ ID NO: 80 or an amino acid sequence sharing identity equal to or higher than 95% with the amino acid sequence represented by SEQ ID NO: 80, and a heavy chain CDR3 having an amino acid sequence represented by SEQ ID NO: 82 or an amino acid sequence sharing identity equal to or higher than 95% with the amino acid sequence represented by SEQ ID NO: 82 and/or a light chain variable region containing a light chain CDR1 having an amino acid sequence represented by SEQ ID NO: 169 or an amino acid sequence sharing identity equal to or higher than 95% with the amino acid sequence represented by SEQ ID NO: 169, a light chain CDR2 having an amino acid sequence represented by SEQ ID NO: 171 or an amino acid sequence sharing identity equal to or higher than 95% with the amino acid sequence represented by SEQ ID NO: 171, and a light chain CDR3 having an amino acid sequence represented by SEQ ID NO: 173 or an amino acid sequence sharing identity equal to or higher than 95% with the amino acid sequence represented by SEQ ID NO: 173;

(B) antibody B which contains a heavy chain variable region containing a heavy chain CDR1 having an amino acid sequence represented by SEQ ID NO: 57 or an amino acid sequence sharing identity equal to or higher than 95% with the amino acid sequence represented by SEQ ID NO: 57, a heavy chain CDR2 having an amino acid sequence represented by SEQ ID NO: 59 or an amino acid sequence sharing identity equal to or higher than 95% with the amino acid sequence represented by SEQ ID NO: 59, and a heavy chain CDR3 having an amino acid sequence represented by SEQ ID NO: 61 or an amino acid sequence sharing identity equal to or higher than 95% with the amino acid sequence represented by SEQ ID NO: 61 and/or a light chain variable region containing a light chain CDR1 having an amino acid sequence represented by SEQ ID NO: 148 or an amino acid sequence sharing identity equal to or higher than 95% with the amino acid sequence represented by SEQ ID NO: 148, a light chain CDR2 having an amino acid sequence represented by SEQ ID NO: 150 or an amino acid sequence sharing identity equal to or higher than 95% with the amino acid sequence represented by SEQ ID NO: 150, and a light chain CDR3 having an amino acid sequence represented by SEQ ID NO: 152 or an amino acid sequence sharing identity equal to or higher than 95% with the amino acid sequence represented by SEQ ID NO: 152:

(F) antibody F which contains a heavy chain variable region containing a heavy chain CDR1 having an amino acid sequence represented by SEQ ID NO: 85 or an amino acid sequence sharing identity equal to or higher than 95% with the amino acid sequence represented by SEQ ID NO: 85, a heavy chain CDR2 having an amino acid sequence represented by SEQ ID NO: 87 or an amino acid sequence sharing identity equal to or higher than 95% with the amino acid sequence represented by SEQ ID NO: 87, and a heavy chain CDR3 having an amino acid sequence represented by SEQ ID NO: 89 or an amino acid sequence sharing identity equal to or higher than 95% with the amino acid sequence represented by SEQ ID NO: 89 and/or a light chain variable region containing a light chain CDR1 having an amino acid sequence represented by SEQ ID NO: 176 or an amino acid sequence sharing identity equal to or higher than 95% with the amino acid sequence represented by SEQ ID NO: 176, a light chain CDR2 having an amino acid sequence represented by SEQ ID NO: 178 or an amino acid sequence sharing identity equal to or higher than 95% with the amino acid sequence represented by SEQ ID NO: 178, and a light chain CDR3 having an amino acid sequence represented by SEQ ID NO: 180 or an amino acid sequence sharing identity equal to or higher than 95% with the amino acid sequence represented by SEQ ID NO: 180;

(C) antibody C which contains a heavy chain variable region containing a heavy chain CDR1 having an amino acid sequence represented by SEQ ID NO: 64 or an amino acid sequence sharing identity equal to or higher than 95% with the amino acid sequence represented by SEQ ID NO: 64, a heavy chain CDR2 having an amino acid sequence represented by SEQ ID NO: 66 or an amino acid sequence sharing identity equal to or higher than 95% with the amino acid sequence represented by SEQ ID NO: 66, and a heavy chain CDR3 having an amino acid sequence represented by SEQ ID NO: 68 or an amino acid sequence sharing identity equal to or higher than 95% with the amino acid sequence represented by SEQ ID NO: 68 and/or a light chain variable region containing a light chain CDR1 having an amino acid sequence represented by SEQ ID NO: 155 or an amino acid sequence sharing identity equal to or higher than 95% with the amino acid sequence represented by SEQ ID NO: 155, a light chain CDR2 having an amino acid sequence represented by SEQ ID NO: 157 or an amino acid sequence sharing identity equal to or higher than 95% with the amino acid sequence represented by SEQ ID NO: 157, and a light chain CDR3 having an amino acid sequence represented by SEQ ID NO: 159 or an amino acid sequence sharing identity equal to or higher than 95% with the amino acid sequence represented by SEQ ID NO: 159;

(A) antibody A which contains a heavy chain variable region containing a heavy chain CDR1 having an amino acid sequence represented by SEQ ID NO: 50 or an amino acid sequence sharing identity equal to or higher than 95% with the amino acid sequence represented by SEQ ID NO: 50, a heavy chain CDR2 having an amino acid sequence represented by SEQ ID NO: 52 or an amino acid sequence sharing identity equal to or higher than 95% with the amino acid sequence represented by SEQ ID NO: 52, and a heavy chain CDR3 having an amino acid sequence represented by SEQ ID NO: 54 or an amino acid sequence sharing identity equal to or higher than 95% with the amino acid sequence represented by SEQ ID NO: 54 and/or a light chain variable region containing a light chain CDR1 having an amino acid sequence represented by SEQ ID NO: 141 or an amino acid sequence sharing identity equal to or higher than 95% with the amino acid sequence represented by SEQ ID NO: 141, a light chain CDR2 having an amino acid sequence represented by SEQ ID NO: 143 or an amino acid sequence sharing identity equal to or higher than 95% with the amino acid sequence represented by SEQ ID NO: 143, and a light chain CDR3 having an amino acid sequence represented by SEQ ID NO: 145 or an amino acid sequence sharing identity equal to or higher than 95% with the amino acid sequence represented by SEQ ID NO: 145;

(K) antibody K which contains a heavy chain variable region containing a heavy chain CDR1 having an amino acid sequence represented by SEQ ID NO: 120 or an amino acid sequence sharing identity equal to or higher than 95% with the amino acid sequence represented by SEQ ID NO: 120, a heavy chain CDR2 having an amino acid sequence represented by SEQ ID NO: 122 or an amino acid sequence sharing identity equal to or higher than 95% with the amino acid sequence represented by SEQ ID NO: 122, and a heavy chain CDR3 having an amino acid sequence represented by SEQ ID NO: 124 or an amino acid sequence sharing identity equal to or higher than 95% with the amino acid sequence represented by SEQ ID NO: 124 and/or a light chain variable region containing a light chain CDR1 having an amino acid sequence represented by SEQ ID NO: 211 or an amino acid sequence sharing identity equal to or higher than 95% with the amino acid sequence represented by SEQ ID NO: 211, a light chain CDR2 having an amino acid sequence represented by SEQ ID NO: 213 or an amino acid sequence sharing identity equal to or higher than 95% with the amino acid sequence represented by SEQ ID NO: 213, and a light chain CDR3 having an amino acid sequence represented by SEQ ID NO: 215 or an amino acid sequence sharing identity equal to or higher than 95% with the amino acid sequence represented by SEQ ID NO: 215;

(D) antibody D which contains a heavy chain variable region containing a heavy chain CDR1 having an amino acid sequence represented by SEQ ID NO: 71 or an amino acid sequence sharing identity equal to or higher than 95% with the amino acid sequence represented by SEQ ID NO: 71, a heavy chain CDR2 having an amino acid sequence represented by SEQ ID NO: 73 or an amino acid sequence sharing identity equal to or higher than 95% with the amino acid sequence represented by SEQ ID NO: 73, and a heavy chain CDR3 having an amino acid sequence represented by SEQ ID NO: 75 or an amino acid sequence sharing identity equal to or higher than 95% with the amino acid sequence represented by SEQ ID NO: 75 and/or a light chain variable region containing a light chain CDR1 having an amino acid sequence represented by SEQ ID NO: 162 or an amino acid sequence sharing identity equal to or higher than 95% with the amino acid sequence represented by SEQ ID NO: 162, a light chain CDR2 having an amino acid sequence represented by SEQ ID NO: 164 or an amino acid sequence sharing identity equal to or higher than 95% with the amino acid sequence represented by SEQ ID NO: 164, and a light chain CDR3 having an amino acid sequence represented by SEQ ID NO: 166 or an amino acid sequence sharing identity equal to or higher than 95% with the amino acid sequence represented by SEQ ID NO: 166;

(G) antibody G which contains a heavy chain variable region containing a heavy chain CDR1 having an amino acid sequence represented by SEQ ID NO: 92 or an amino acid sequence sharing identity equal to or higher than 95% with the amino acid sequence represented by SEQ ID NO: 92, a heavy chain CDR2 having an amino acid sequence represented by SEQ ID NO: 94 or an amino acid sequence sharing identity equal to or higher than 95% with the amino acid sequence represented by SEQ ID NO: 94, and a heavy chain CDR3 having an amino acid sequence represented by SEQ ID NO: 96 or an amino acid sequence sharing identity equal to or higher than 95% with the amino acid sequence represented by SEQ ID NO: 96 and/or a light chain variable region containing a light chain CDR1 having an amino acid sequence represented by SEQ ID NO: 183 or an amino acid sequence sharing identity equal to or higher than 95% with the amino acid sequence represented by SEQ m NO: 183, a light chain CDR2 having an amino acid sequence represented by SEQ ID NO: 185 or an amino acid sequence sharing identity equal to or higher than 95% with the amino acid sequence represented by SEQ ID NO: 185, and a light chain CDR3 having an amino acid sequence represented by SEQ ID NO: 187 or an amino acid sequence sharing identity equal to or higher than 95% with the amino acid sequence represented by SEQ ID NO: 187;

(H) antibody H which contains a heavy chain variable region containing a heavy chain CDR1 having an amino acid sequence represented by SEQ ID NO: 99 or an amino acid sequence sharing identity equal to or higher than 95% with the amino acid sequence represented by SEQ ID NO: 99, a heavy chain CDR2 having an amino acid sequence represented by SEQ ID NO: 101 or an amino acid sequence sharing identity equal to or higher than 95% with the amino acid sequence represented by SEQ ID NO: 101, and a heavy chain CDR3 having an amino acid sequence represented by SEQ ID NO: 103 or an amino acid sequence sharing identity equal to or higher than 95% with the amino acid sequence represented by SEQ ID NO: 103 and/or a light chain variable region containing a light chain CDR1 having an amino acid sequence represented by SEQ ID NO: 190 or an amino acid sequence sharing identity equal to or higher than 95% with the amino acid sequence represented by SEQ ID NO: 190, a light chain CDR2 having an amino acid sequence represented by SEQ ID NO: 192 or an amino acid sequence sharing identity equal to or higher than 95% with the amino acid sequence represented by SEQ ID NO: 192; and a light chain CDR3 having an amino acid sequence represented by SEQ ID NO: 194 or an amino acid sequence sharing identity equal to or higher than 95% with the amino acid sequence represented by SEQ ID NO: 194;

(J) antibody J which contains a heavy chain variable region containing a heavy chain CDR1 having an amino acid sequence represented by SEQ ID NO: 113 or an amino acid sequence sharing identity equal to or higher than 95% with the amino acid sequence represented by SEQ ID NO: 113, a heavy chain CDR2 having an amino acid sequence represented by SEQ ID NO: 115 or an amino acid sequence sharing identity equal to or higher than 95% with the amino acid sequence represented by SEQ ID NO: 115, and a heavy chain CDR3 having an amino acid sequence represented by SEQ ID NO: 117 or an amino acid sequence sharing identity equal to or higher than 95% with the amino acid sequence represented by SEQ ID NO: 117 and/or a light chain variable region containing a light chain CDR1 having an amino acid sequence represented by SEQ ID NO: 204 or an amino acid sequence sharing identity equal to or higher than 95% with the amino acid sequence represented by SEQ ID NO: 204, a light chain CDR2 having an amino acid sequence represented by SEQ ID NO: 206 or an amino acid sequence sharing identity equal to or higher than 95% with the amino acid sequence represented by SEQ ID NO: 206, and a light chain CDR3 having an amino acid sequence represented by SEQ ID NO: 208 or an amino acid sequence sharing identity equal to or higher than 95% with the amino acid sequence represented by SEQ ID NO: 208;

(L) antibody L which contains a heavy chain variable region containing a heavy chain CDR1 having an amino acid sequence represented by SEQ ID NO: 127 or an amino acid sequence sharing identity equal to or higher than 95% with the amino acid sequence represented by SEQ ID NO: 127, a heavy chain CDR2 having an amino acid sequence represented by SEQ ID NO: 129 or an amino acid sequence sharing identity equal to or higher than 95% with the amino acid sequence represented by SEQ ID NO: 129, and a heavy chain CDR3 having an amino acid sequence represented by SEQ ID NO: 131 or an amino acid sequence sharing identity equal to or higher than 95% with the amino acid sequence represented by SEQ ID NO: 131 and/or a light chain variable region containing a light chain CDR1 having an amino acid sequence represented by SEQ ID NO: 218 or an amino acid sequence sharing identity equal to or higher than 95% with the amino acid sequence represented by SEQ ID NO: 218, a light chain CDR2 having an amino acid sequence represented by SEQ ID NO: 220 or an amino acid sequence sharing identity equal to or higher than 95% with the amino acid sequence represented by SEQ ID NO: 220, and a light chain CDR3 having an amino acid sequence represented by SEQ ID NO: 222 or an amino acid sequence sharing identity equal to or higher than 95% with the amino acid sequence represented by SEQ ID NO: 222; and (M) antibody M which contains a heavy chain variable region containing a heavy chain CDR1 having an amino acid sequence represented by SEQ ID NO: 134 or an amino acid sequence sharing identity equal to or higher than 95% with the amino acid sequence represented by SEQ ID NO: 134, a heavy chain CDR2 having an amino acid sequence represented by SEQ ID NO: 136 or an amino acid sequence sharing identity equal to or higher than 95% with the amino acid sequence represented by SEQ ID NO: 136, and a heavy chain CDR3 having an amino acid sequence represented by SEQ ID NO: 138 or an amino acid sequence sharing identity equal to or higher than 95% with the amino acid sequence represented by SEQ ID NO: 138 and/or a light chain variable region containing a light chain CDR1 having an amino acid sequence represented by SEQ ID NO: 225 or an amino acid sequence sharing identity equal to or higher than 95% with the amino acid sequence represented by SEQ ID NO: 225, a light chain CDR2 having an amino acid sequence represented by SEQ ID NO: 227 or an amino acid sequence sharing identity equal to or higher than 95% with the amino acid sequence represented by SEQ ID NO: 227, and a light chain CDR3 having an amino acid sequence represented by SEQ ID NO: 229 or an amino acid sequence sharing identity equal to or higher than 95% with the amino acid sequence represented by SEQ ID NO: 229.

12. The antibody described in any one of 1 to 11, in which a variable region VH of the antibody has a sequence represented by SEQ ID NO: 1, 3, 5, 7, 9, 11, 13, 15, 17, 19, 21, 23, or 25 or an amino acid sequence sharing identity equal to or higher than 90% with any of these amino acid sequences, and a variable region VL of the antibody has a sequence represented by SEQ ID NO: 2.4, 6, 8, 10, 12, 14, 16, 18, 20, 22, 24, or 26 or an amino acid sequence sharing identity equal to or higher than 90% with any of these amino acid sequences.

13. A cell containing a polynucleotide encoding the antibody described in any one of 1 to 12.

The present invention also includes the following aspect as another embodiment:

1A. An antibody that specifically recognizes a three-dimensional structure or a primary structure of an extracellular domain of a Claudin-5 protein.

2A. The antibody described in 1 that binds to none of extracellular domains of a Claudin-1 protein, a Claudin-2 protein, a Claudin-3 protein, a Claudia-4 protein, a Claudin-6 protein, and a Claudin-7 protein.

3A. The antibody described in 1 or 2 that specifically recognizes a domain ranging from the $28^{th}$ amino acid (proline) to the $80^{th}$ amino acid (alanine) from the N-terminal in a human CLDN-5 protein consisting of an amino acid sequence represented by SEQ ID NO: 27.

4A. The antibody described in any one of 1 to 3 of which a binding capacity to a protein 1-1-5 consisting of an amino acid sequence represented by SEQ ID NO: 45 is equal to or lower than ⅕ of a binding capacity thereof to a human Claudin-5 protein consisting of an amino acid sequence represented by SEQ ID NO: 27, wherein the protein 1-1-5 is the one where a first extracellular loop of the human Claudin-5 protein is substituted with a first loop of a human Claudin-1 protein.

5A. The antibody described in 4 of which a binding capacity to a human Claudin-5 protein point mutant D68E consisting of an amino acid sequence represented by SEQ ID NO: 41 is equal to or lower than ⅕ of a binding capacity thereof to a human Claudin-5 protein consisting of an amino acid sequence represented by SEQ ID NO: 27.

6A. The antibody described in 1 or 2 that specifically recognizes a domain ranging from the $147^{th}$ amino acid (phenylalanine) to the $163^{rd}$ amino acid (alanine) from the N-terminal in a human CLDN-5 protein consisting of an amino acid sequence represented by SEQ ID NO: 27.

7A. The antibody described in any one of 1, 2, or 6 of which a binding capacity to a protein 5-5-1 consisting of an amino acid sequence represented by SEQ ID NO: 48 is equal to or lower than ⅕ of a binding capacity thereof to a human Claudin-5 protein consisting of an amino acid sequence represented by SEQ ID NO: 27, in which the protein 5-5-1 is obtained by substituting a second extracellular loop of the human Claudin-5 protein with a second loop of the human Claudin-1 protein.

8A. The antibody described in 7 of which a binding capacity to a human Claudin-5 protein point mutant S151T consisting of an amino acid sequence represented by SEQ ID NO: 43 is equal to or lower than ⅕ of a binding capacity thereof to a human Claudin-5 protein consisting of an amino acid sequence represented by SEQ ID NO: 27.

9A. The antibody described in 1 or 2 that specifically recognizes a three-dimensional structure formed of a domain ranging from the $28^{th}$ amino acid (proline) to the $80^{th}$ amino acid (alanine) from the N-terminal and a domain ranging from the $147^{th}$ amino acid (phenylalanine) to the $163^{rd}$ amino acid (alanine) from the N-terminal in a human CLDN-5 protein consisting of an amino acid sequence represented by SEQ ID NO: 27.

10A. The antibody described in any one of 1, 2, or 9 of which a binding capacity to a mutant TM consisting of an amino acid sequence represented by SEQ ID NO: 44 is equal to or lower than ⅕ of a binding capacity thereof to a human Claudin-5 protein consisting of an amino acid sequence represented by SEQ ID NO: 27, wherein the mutant TM is the one where the human Claudin-5 protein except for an extracellular domain thereof is substituted with a mouse Claudin-5 protein.

11A. The antibody described in any one of 1 to 10 that is selected from the group consisting of the following antibodies A to M:

(A) antibody A which contains a heavy chain variable region containing a heavy chain CDR1 having an amino acid sequence represented by SEQ ID NO: 50 or an amino acid sequence sharing identity equal to or higher than 95% with the amino acid sequence represented by SEQ ID NO: 50, a heavy chain CDR2 having an amino acid sequence represented by SEQ ID NO: 52 or an amino acid sequence sharing identity equal to or higher than 95% with the amino acid sequence represented by SEQ ID NO: 52, and a heavy chain CDR3 having an amino acid sequence represented by SEQ ID NO: 54 or an amino acid sequence sharing identity equal to or higher than 95% with the amino acid sequence represented by SEQ ID NO: 54 and/or a light chain variable region containing a light chain CDR1 having an amino acid sequence represented by SEQ ID NO: 141 or an amino acid sequence sharing identity equal to or higher than 95% with the amino acid sequence represented by SEQ ID NO: 141, a light chain CDR2 having an amino acid sequence represented by SEQ ID NO: 143 or an amino acid sequence sharing identity equal to or higher than 95% with the amino acid sequence represented by SEQ ID NO: 143, and a light chain CDR3 having an amino acid sequence represented by SEQ ID NO: 145 or an amino acid sequence sharing identity equal to or higher than 95% with the amino acid sequence represented by SEQ ID NO: 145;

(B) antibody B which contains a heavy chain variable region containing a heavy chain CDR1 having an amino acid sequence represented by SEQ ID NO: 57 or an amino acid sequence sharing identity equal to or higher than 95% with the amino acid sequence represented by SEQ ID NO: 57, a heavy chain CDR2 having an amino acid sequence represented by SEQ ID NO: 59 or an amino acid sequence sharing identity equal to or higher than 95% with the amino acid sequence represented by SEQ ID NO: 59, and a heavy chain CDR3 having an amino acid sequence represented by SEQ ID NO: 61 or an amino acid sequence sharing identity equal to or higher than 95% with the amino acid sequence represented by SEQ ID NO: 61 and/or a light chain variable region containing a light chain CDR1 having an amino acid sequence represented by SEQ ID NO: 148 or an amino acid sequence sharing identity equal to or higher than 95% with the amino acid sequence represented by SEQ ID NO: 148, a light chain CDR2 having an amino acid sequence represented by SEQ ID NO: 150 or an amino acid sequence sharing identity equal to or higher than 95% with the amino acid sequence represented by SEQ ID NO: 150, and a light chain CDR3 having an amino acid sequence represented by SEQ ID NO: 152 or an amino acid sequence sharing identity equal to or higher than 95% with the amino acid sequence represented by SEQ ID NO: 152;

(C) antibody C which contains a heavy chain variable region containing a heavy chain CDR1 having an amino acid sequence represented by SEQ ID NO: 64 or an amino acid sequence sharing identity equal to or higher than 95% with the amino acid sequence represented by SEQ ID NO: 64, a heavy chain CDR2 having an amino acid sequence represented by SEQ ID NO: 66 or an amino acid sequence sharing identity equal to or higher than 95% with the amino acid sequence represented by SEQ ID NO: 66, and a heavy chain CDR3 having an amino acid sequence represented by SEQ ID NO: 68 or an amino acid sequence sharing identity equal to or higher than 95% with the amino acid sequence represented by SEQ ID NO: 68 and/or a light chain variable region containing a light chain CDR1 having an amino acid sequence represented by SEQ ID NO: 155 or an amino acid sequence sharing identity equal to or higher than 95% with the amino acid sequence represented by SEQ ID NO: 155, a light chain CDR2 having an amino acid sequence represented by SEQ ID NO: 157 or an amino acid sequence sharing identity equal to or higher than 95% with the amino acid sequence represented by SEQ ID NO: 157, and a light chain CDR3 having an amino acid sequence represented by SEQ ID NO: 159 or an amino acid sequence sharing identity equal to or higher than 95% with the amino acid sequence represented by SEQ ID NO: 159;

(D) antibody D which contains a heavy chain variable region containing a heavy chain CDR1 having an amino acid sequence represented by SEQ ID NO: 71 or an amino acid sequence sharing identity equal to or higher than 95% with the amino acid sequence represented by SEQ ID NO: 71, a heavy chain CDR2 having an amino acid sequence represented by SEQ ID NO: 73 or an amino acid sequence sharing identity equal to or higher than 95% with the amino acid sequence represented by SEQ ID NO: 73, and a heavy chain CDR3 having an amino acid sequence represented by SEQ ID NO: 75 or an amino acid sequence sharing identity equal to or higher than 95% with the amino acid sequence represented by SEQ ID NO: 75 and/or a light chain variable region containing a light chain CDR1 having an amino acid sequence represented by SEQ ID NO: 162 or an amino acid sequence sharing identity equal to or higher than 95% with the amino acid sequence represented by SEQ ID NO: 162, a light chain CDR2 having an amino acid sequence represented by SEQ ID NO: 164 or an amino acid sequence sharing identity equal to or higher than 95% with the amino acid sequence represented by SEQ ID NO: 164, and a light chain CDR3 having an amino acid sequence represented by SEQ ID NO: 166 or an amino acid sequence sharing identity equal to or higher than 95% with the amino acid sequence represented by SEQ ID NO: 166;

(E) antibody E which contains a heavy chain variable region containing a heavy chain CDR1 having an amino acid sequence represented by SEQ ID NO: 78 or an amino acid sequence sharing identity equal to or higher than 95% with the amino acid sequence represented by SEQ ID NO: 78, a heavy chain CDR2 having an amino acid sequence represented by SEQ ID NO: 80 or an amino acid sequence sharing identity equal to or higher than 95% with the amino acid sequence represented by SEQ ID NO: 80, and a heavy chain CDR3 having an amino acid sequence represented by SEQ ID NO: 82 or an amino acid sequence sharing identity equal to or higher than 95% with the amino acid sequence represented by SEQ ID NO: 82 and/or a light chain variable region containing a light chain CDR1 having an amino acid sequence represented by SEQ ID NO: 169 or an amino acid sequence sharing identity equal to or higher than 95% with the amino acid sequence represented by SEQ ID NO: 169, a light chain CDR2 having an amino acid sequence represented by SEQ ID NO: 171 or an amino acid sequence sharing identity equal to or higher than 95% with the amino acid sequence represented by SEQ ID NO: 171, and a light chain CDR3 having an amino acid sequence represented by SEQ ID NO: 173 or an amino acid sequence sharing identity equal to or higher than 95% with the amino acid sequence represented by SEQ II) NO: 173;

(F) antibody F which contains a heavy chain variable region containing a heavy chain CDR1 having an amino acid sequence represented by SEQ ID NO: 85 or an amino acid sequence sharing identity equal to or higher than 95% with the amino acid sequence represented by SEQ ID NO: 85, a heavy chain CDR2 having an amino acid sequence represented by SEQ ID NO: 87 or an amino acid sequence sharing identity equal to or higher than 95% with the amino acid sequence represented by SEQ ID NO: 87, and a heavy chain CDR3 having an amino acid sequence represented by SEQ ID NO: 89 or an amino acid sequence sharing identity equal to or higher than 95% with the amino acid sequence represented by SEQ ID NO: 89 and/or a light chain variable region containing a light chain CDR1 having an amino acid sequence represented by SEQ ID NO: 176 or an amino acid sequence sharing identity equal to or higher than 95% with the amino acid sequence represented by SEQ ID NO: 176, a light chain CDR2 having an amino acid sequence represented by SEQ ID NO: 178 or an amino acid sequence sharing identity equal to or higher than 95% with the amino acid sequence represented by SEQ ID NO: 178, and a light chain CDR3 having an amino acid sequence represented by SEQ ID NO: 180 or an amino acid sequence sharing identity equal to or higher than 95% with the amino acid sequence represented by SEQ ID NO: 180;

(G) antibody G which contains a heavy chain variable region containing a heavy chain CDR1 having an amino acid sequence represented by SEQ ID NO: 92 or an amino acid sequence sharing identity equal to or higher than 95% with the amino acid sequence represented by SEQ ID NO: 92, a heavy chain CDR2 having an amino acid sequence represented by SEQ ID NO: 94 or an amino acid sequence sharing identity equal to or higher than 95% with the amino acid sequence represented by SEQ ID NO: 94, and a heavy chain CDR3 having an amino acid sequence represented by SEQ ID NO: 96 or an amino acid sequence sharing identity equal to or higher than 95% with the amino acid sequence represented by SEQ ID NO: 96 and/or a light chain variable region containing a light chain CDR1 having an amino acid sequence represented by SEQ ID NO: 183 or an amino acid sequence sharing identity equal to or higher than 95% with the amino acid sequence represented by SEQ ID NO: 183, a light chain CDR2 having an amino acid sequence represented by SEQ ID NO: 185 or an amino acid sequence sharing identity equal to or higher than 95% with the amino acid sequence represented by SEQ ID NO: 185, and a light chain CDR3 having an amino acid sequence represented by SEQ ID NO: 187 or an amino acid sequence sharing identity equal to or higher than 95% with the amino acid sequence represented by SEQ ID NO: 187;

(H) antibody H which contains a heavy chain variable region containing a heavy chain CDR1 having an amino acid sequence represented by SEQ ID NO: 99 or an amino acid sequence sharing identity equal to or higher than 95% with the amino acid sequence represented by SEQ ID NO: 99, a heavy chain CDR2 having an amino acid sequence represented by SEQ ID NO: 101 or an amino acid sequence sharing identity equal to or higher than 95% with the amino acid sequence represented by SEQ ID NO: 101, and a heavy chain CDR3 having an amino acid sequence represented by SEQ ID NO: 103 or an amino acid sequence sharing identity equal to or higher than 95% with the amino acid sequence represented by SEQ ID NO: 103 and/or a light chain variable region containing a light chain CDR1 having an amino acid sequence represented by SEQ ID NO: 190 or an amino acid sequence sharing identity equal to or higher than 95% with the amino acid sequence represented by SEQ ID NO: 190, a light chain CDR2 having an amino acid sequence represented by SEQ ID NO: 192 or an amino acid sequence sharing identity equal to or higher than 95% with the amino acid sequence represented by SEQ ID NO: 192, and a light chain CDR3 having an amino acid sequence represented by SEQ ID NO: 194 or an amino acid sequence sharing identity equal to or higher than 95% with the amino acid sequence represented by SEQ ID NO: 194;

(I) antibody I which contains a heavy chain variable region containing a heavy chain CDR1 having an amino acid sequence represented by SEQ ID NO: 106 or an amino acid sequence sharing identity equal to or higher than 95% with the amino acid sequence represented by SEQ ID NO: 106, a heavy chain CDR2 having an amino acid sequence represented by SEQ ID NO: 108 or an amino acid sequence sharing identity equal to or higher than 95% with the amino acid sequence represented by SEQ ID NO: 108, and a heavy chain CDR3 having an amino acid sequence represented by SEQ ID NO: 110 or an amino acid sequence sharing identity equal to or higher than 95% with the amino acid sequence represented by SEQ ID NO: 110 and/or a light chain variable region containing a light chain CDR1 having an amino acid sequence represented by SEQ ID NO: 197 or an amino acid sequence sharing identity equal to or higher than 95% with the amino acid sequence represented by SEQ ID NO: 197, a light chain CDR2 having an amino acid sequence represented by SEQ ID NO: 199 or an amino acid sequence sharing identity equal to or higher than 95% with the amino acid sequence represented by SEQ ID NO: 199, and a light chain CDR3 having an amino acid sequence represented by SEQ ID NO: 201 or an amino acid sequence sharing identity equal to or higher than 95% with the amino acid sequence represented by SEQ ID NO: 201;

(J) antibody J which contains a heavy chain variable region containing a heavy chain CDR1 having an amino acid sequence represented by SEQ ID NO: 113 or an amino acid sequence sharing identity equal to or higher than 95% with the amino acid sequence represented by SEQ ID NO: 113, a heavy chain CDR2 having an amino acid sequence represented by SEQ ID NO: 115 or an amino acid sequence sharing identity equal to or higher than 95% with the amino acid sequence represented by SEQ ID NO: 115, and a heavy chain CDR3 having an amino acid sequence represented by SEQ ID NO: 117 or an amino acid sequence sharing identity equal to or higher than 95% with the amino acid sequence represented by SEQ ID NO: 117 and/or a light chain variable region containing a light chain CDR1 having an amino acid sequence represented by SEQ ID NO: 204 or an amino acid sequence sharing identity equal to or higher than 95% with the amino acid sequence represented by SEQ ID NO: 204, a light chain CDR2 having an amino acid sequence represented by SEQ ID NO: 206 or an amino acid sequence sharing identity equal to or higher than 95% with the amino acid sequence represented by SEQ ID NO: 206, and a light chain CDR3 having an amino acid sequence represented by SEQ ID NO: 208 or an amino acid sequence sharing identity equal to or higher than 95% with the amino acid sequence represented by SEQ ID NO: 208;

(K) antibody K which contains a heavy chain variable region containing a heavy chain CDR1 having an amino acid sequence represented by SEQ ID NO: 120 or an amino acid sequence sharing identity equal to or higher than 95% with the amino acid sequence represented by SEQ ID NO: 120, a heavy chain CDR2 having an amino acid sequence represented by SEQ ID NO: 122 or an amino acid sequence sharing identity equal to or higher than 95% with the amino acid sequence represented by SEQ ID NO: 122, and a heavy chain CDR3 having an amino acid sequence represented by SEQ ID NO: 124 or an amino acid sequence sharing identity equal to or higher than 95% with the amino acid sequence represented by SEQ ID NO: 124 and/or a light chain variable region containing a light chain CDR1 having an amino acid sequence represented by SEQ ID NO: 211 or an amino acid sequence sharing identity equal to or higher than 95% with the amino acid sequence represented by SEQ ID NO: 211, a light chain CDR2 having an amino acid sequence represented by SEQ ID NO: 213 or an amino acid sequence sharing identity equal to or higher than 95% with the amino acid sequence represented by SEQ ID NO: 213, and a light chain CDR3 having an amino acid sequence represented by SEQ ID NO: 215 or an amino acid sequence sharing identity equal to or higher than 95% with the amino acid sequence represented by SEQ ID NO: 215;

(L) antibody L which contains a heavy chain variable region containing a heavy chain CDR1 having an amino acid sequence represented by SEQ ID NO: 127 or an amino acid sequence sharing identity equal to or higher than 95% with the amino acid sequence represented by SEQ ID NO: 127, a heavy chain CDR2 having an amino acid sequence represented by SEQ ID NO: 129 or an amino acid sequence sharing identity equal to or higher than 95% with the amino acid sequence represented by SEQ ID NO: 129, and a heavy chain CDR3 having an amino acid sequence represented by SEQ ID NO: 131 or an amino acid sequence sharing identity equal to or higher than 95% with the amino acid sequence represented by SEQ ID NO: 131 and/or a light chain variable region containing a light chain CDR1 having an amino acid sequence represented by SEQ ID NO: 218 or an amino acid sequence sharing identity equal to or higher than 95% with the amino acid sequence represented by SEQ ID NO: 218, a light chain CDR2 having an amino acid sequence represented by SEQ ID NO: 220 or an amino acid sequence sharing identity equal to or higher than 95% with the amino acid sequence represented by SEQ ID NO: 220, and a light chain CDR3 having an amino acid sequence represented by SEQ ID NO: 222 or an amino acid sequence sharing identity equal to or higher than 95% with the amino acid sequence represented by SEQ ID NO: 222; and (M) antibody M which contains a heavy chain variable region containing a heavy chain CDR1 having an amino acid sequence represented by SEQ ID NO: 134 or an amino acid sequence sharing identity equal to or higher than 95% with the amino acid sequence represented by SEQ ID NO: 134, a heavy chain CDR2 having an amino acid sequence represented by SEQ ID NO: 136 or an amino acid sequence sharing identity equal to or higher than 95% with the amino acid sequence represented by SEQ ID NO: 136, and a heavy chain CDR3 having an amino acid sequence represented by SEQ ID NO: 138 or an amino acid sequence sharing identity equal to or higher than 95% with the amino acid sequence represented by SEQ ID NO: 138 and/or a light chain variable region containing a light chain CDR1 having an amino acid sequence represented by SEQ ID NO: 225 or an amino acid sequence sharing identity equal to or higher than 95% with the amino acid sequence represented by SEQ ID NO: 225, a light chain CDR2 having an amino acid sequence represented by SEQ ID NO: 227 or an amino acid sequence sharing identity equal to or higher than 95% with the amino acid sequence represented by SEQ ID NO: 227, and a light chain CDR3 having an amino acid sequence represented by SEQ ID NO: 229 or an amino acid sequence sharing identity equal to or higher than 95% with the amino acid sequence represented by SEQ ID NO: 229.

12A. The antibody described in any one of 1 to 11, in which a variable region VH of the antibody has a sequence represented by SEQ ID NO: 1, 3, 5, 7, 9, 11, 13, 15, 17, 19, 21, 23, or 25 or an amino acid sequence sharing identity equal to or higher than 90% with any of these amino acid sequences, and a variable region VL of the antibody has a sequence represented by SEQ ID NO: 2, 4, 6, 8, 10, 12, 14, 16, 18, 20, 22, 24, or 26 or an amino acid sequence sharing identity equal to or higher than 90% with any of these amino acid sequences.

13A. A human IgG1 chimeric antibody, a human IgG4 chimeric antibody, a human IgG1 mutant chimeric antibody, a human IgG4 mutant chimeric antibody, or a chimeric antibody obtained by modifying any of these, wherein these antibodies have the variable regions of the antibody described in 11 or 12.

14A. A humanized antibody or a modified humanized antibody having a complementarity determining region of the antibody described in 11 or 12.

15A. An Fab fragment, an F(ab')2 fragment, an Fv fragment, a minibody, scFv-Fc, scFv, a diabody, a triabody, or a tetrabody having the variable regions of the antibody described in 11 or 12.

16A. A cell containing a polynucleotide encoding the antibody or the fragment described in any one of 1 to 15.

17A. A hybridoma containing a polynucleotide encoding the antibody or the fragment described in any one of 1 to 15.

18A. A complex containing the antibody or the fragment described in any one of 1 to 15 and a medication.

19A. A reagent containing at least one kind component selected from the group consisting of the antibody or the fragment thereof described in any one of 1 to 15 and the complex described in 18.

20A. A drug containing at least one kind component selected from the group consisting of the antibody or the fragment thereof described in any one of 1 to 15 and the complex described in 18.

21A. The drug described in 20 that is for controlling the blood-brain barrier.

22A. The drug described in 20 that is for changing localization properties of a Claudin-5 protein.

Advantageous Effects of Invention

Unlike the conventional molecules binding to the extracellular domain of CLDN-5, a monoclonal antibody, which is obtained by the present invention and recognizes the extracellular domain of CLDN-5, exhibits high CLDN-5 specificity. Therefore, the antibody makes it possible to detect•isolate a small cell from a cell population expressing CLDN-5 without immobilizing•permeabilizing the cell. Furthermore, the antibody obtained by the present invention can also be used for scientific purposes. Although vascular endothelial cells including cerebrovascular endothelial cells are known as a heterogeneous group, in a case where the antibody obtained by the present invention is used, for example, it is possible to analyze the cells by grouping these cells based on the difference in expression amounts of CLDN-5. In other words, the antibody can be a reagent useful for understanding the structure of the blood-brain barrier or key clues of the pathological failure thereof.

The antibody developed by the present invention has an activity of controlling a barrier by a tight junction created by sufficient cerebrovascular endothelial cells. Therefore, for example, in a case where the antibody is administered in combination with a medication or administered in the form of a complex of the medication and the antibody, the penetration of the medication into the blood-brain barrier can be accelerated. Consequently, the medication can more effectively prevent or treat diseases such as central nervous system diseases.

According to the present invention, as a novel antibody, an antibody against a CLDN-5 extracellular domain can be provided. Furthermore, the present invention can contribute to the researches relating to CLDN-5, the blood-brain barrier, and the like.

BRIEF DESCRIPTION OF DRAWINGS

FIG. 1A illustrates a binding capacity to human CLDN, and FIG. 1B illustrates a binding capacity to mouse CLDN.

FIG. 2 illustrates FACS histograms showing the binding capacity of the anti-CLDN-5 antibodies obtained in Example 3-2) to CLDN-5 of various animal species. The top of the histograms shows the names of CLDN-5 of various animal species expressed in cells by using a retrovirus (h is the abbreviation for human, c is the abbreviation for crab-eating macaque, m is the abbreviation for mouse, and mock represents retrovirus-infected cell that does not express a CLDN protein). The antibodies used as primary antibodies are shown on the very left side of the histograms. In each of the histograms, the abscissa shows a fluorescence signal, and the ordinate shows a cell count. "Vehicle" means that the primary antibodies are not reacted.

FIG. 7A illustrates results obtained using MDCKII/mock, FIG. 7B illustrates results obtained using MDCKII/hCLDN-5. FIG. 7C shows results obtained using MDCKII/cCLDN-5, and FIG. 7D illustrates results obtained using MDCKII/mCLDN-5. The results obtained in a case where mouse antibodies are treated are shown on the left side, and the results obtained in a case where rat antibodies are treated are shown at the right side. Furthermore, the results obtained from a Vehicle-treated group and a C-CPEmt-treated group in the left and right graphs are common to both the graphs.

FIG. 8A illustrates results obtained using MDCKII/mock, FIG. 8B shows results obtained using MDCKII/hCLDN-5, FIG. 8C illustrates results obtained using MDCKII/cCLDN-5, and FIG. 8D illustrates results obtained using MDCKII/mCLDN-5. The results obtained in a case where mouse antibodies are treated are shown on the left side, and the results obtained in a case where rat antibodies are treated are shown on the right side. Furthermore, the results obtained from a Vehicle-treated group and a C-CPEmt-treated group in the left and right graphs are common to both the graphs.

FIG. 9 illustrates results obtained by treating cells, which are prepared by compelling MDCKII obtained in Example 4-4) to express CLDN-5 of various animal species by using a retrovirus, with the anti-CLDN-5 antibody and evaluating sodium fluorescein permeability thereof 12 hours after the treatment. The ordinate shows apparent permeability coefficients, and the abscissa shows the name and the concentration of each of test substances. "Vehicle" means that a liquid used for diluting antibodies is added. Each value is an average (n 3), and a bar represents a standard deviation. The graphs on the first line show results obtained using MDCKII/mock, the graphs on the second line show results obtained using MDCKII/hCLDN-5, the graphs on the third line show results obtained using MDCKII/cCLDN-5, and the graphs on the fourth line show results obtained using MDCKII/mCLDN-5. The results obtained in a case where mouse antibodies are treated are shown on the left side, and the results obtained in a case where rat antibodies are treated are shown on the right side. Furthermore, the results obtained from a Vehicle-treated group and a C-CPEmt-treated group in the left and right graphs on the same line are common to both the graphs.

DESCRIPTION OF EMBODIMENTS

1. Definition

Figure 1A:
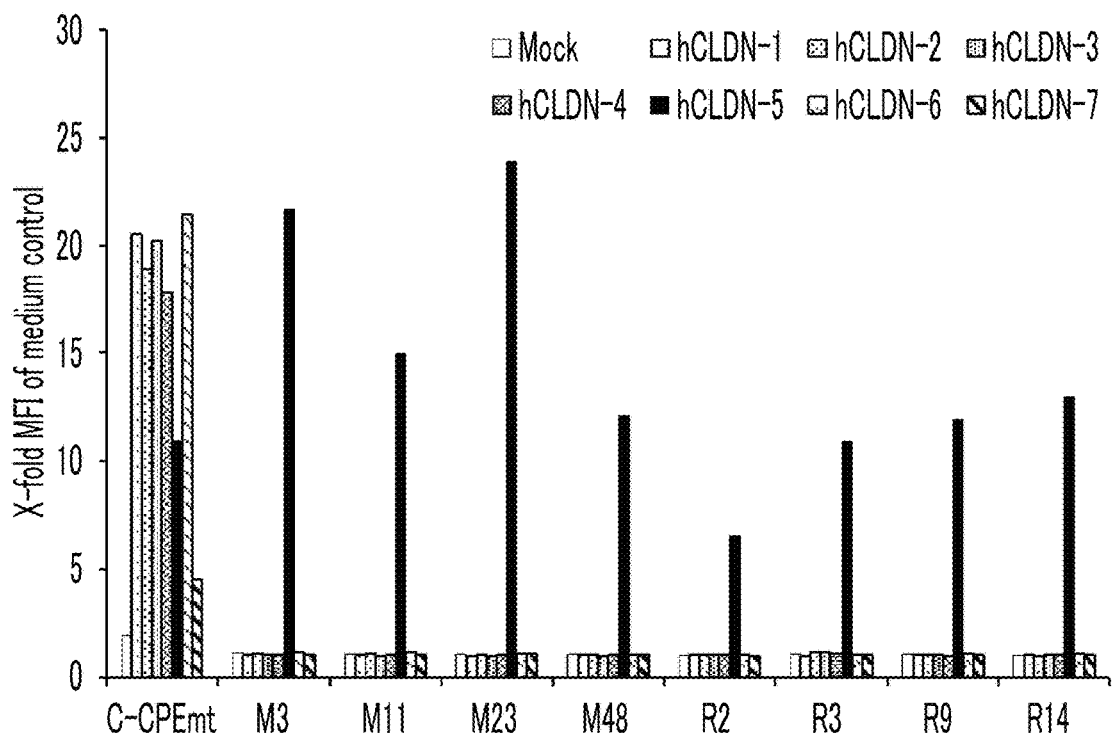
FIGS. 1A and 1B illustrate results of CLDN specificity of CLDN-5 antibodies obtained in Example 3-1). The ordinate shows values obtained by dividing the average fluorescence intensity, which is obtained in a case where each of the antibodies is allowed to react with each of the CLDN-expressing cells, by the average fluorescence intensity obtained in a case where a vehicle is allowed to react with each of the CLDN-expressing cells. The abscissa shows each of the antibodies, and each of the columns shows that each of the CLDN- or mock-expressing cells is allowed to react with the antibodies (mock represents a cell that does not express a CLDN protein).

In the present specification, expressions such as "Ganyuu" and "Hukumu" in Japanese have concepts such as "contain", "containing", "substantially consist of", and "consist only of".

"Identity" of amino acid sequences refers to a degree of coincidence between two or more comparable amino acid sequences. Accordingly the higher the coincidence between two given amino acid sequences, the higher the identity or analogy between the sequences. The level of identity of amino acid sequences is determined, for example, using FASTA as a sequence analysis tool and default parameters. Alternatively, the level of identity can be determined using the BLAST algorithm by Karlin and Altschul (Karlin S, Altschul S F. "Methods for assessing the statistical significance of molecular sequence features by using general scoring schemes" Proc Natl Acad Sci USA. 87:2264-2268 (1990) Karlin S, Altschul S F, "Applications and statistics for multiple high-scoring segments in molecular sequences." Proc Natl Acad Sci USA, 90:5873-7 (1993)). There is a program called BLASTX developed based on the BLAST algorithm. Specific analysis techniques thereof are known, and the website of National Center of Biotechnology Information (NCBI) (www.ncbi.nlm.nih.gov/) may be referred to. "Identity" of base sequences is also defined based on the above.

In the present specification, "conservative substitution" means that amino acid residues are substituted with other amino acid residues having similar side chains. For example, the substitution between amino acid residues having basic side chains such as lysine, arginine, and histidine is conservative substitution. In addition, the substitution between amino acid residues having an acidic side chain such as aspartic acid and glutamic acid; amino acid residues having an antistatic polar side chain such as glycine, asparagine, glutamine, serine, threonine, tyrosine, and cysteine; amino acid residues having a non-polar side chain such as alanine, valine, leucine, isoleucine, proline, phenylalanine, methionine, and tryptophan; amino acid residues having a β-branched side chain such as threonine, valine, and isoleucine; and amino acid residues having an aromatic side chain such as tyrosine, phenylalanine, tryptophan, and histidine is also conservative substitution.

In the present specification, "CDR" is the abbreviation for Complementarity Determining Region which is also called "Sohosei Kettei Ryouiki" in Japanese. CDR is a region which is present in a variable region of immunoglobulin and deeply involved in the specific binding of an antibody to an antigen. "Light chain CDR" is CDR present in a variable region of a light chain of immunoglobulin, and "heavy chain CDR" is CDR present in a variable region of a heavy chain of immunoglobulin.

In the present specification, "variable region" refers to a region containing CDR1 to CDR3 (hereinafter, simply described as "CDRs 1-3"). Although the arrangement order of CDRs 1-3 is not particularly limited, the variable region preferably means a region in which CDR1, CDR2, and CDR3 are arranged in this order from the N-terminal side to the C-terminal side or arranged in reverse order consecutively or through another amino acid sequence called framework region (FR) which will be described later. "Heavy chain variable region" is a region in which the heavy chain CDRs 1-3 are arranged, and "light chain variable region" is a region in which the light chains CDRs 1-3 are arranged.

As described above, a region other than the aforementioned CDRs 1.3 of each variable region is called framework region (FR). Particularly, a region between the N-terminal of a variable region and CDR1 is defined as FR1, a region between CDR1 and CDR2, is defined as FR2, a region between CDR2 and CDR3 is defined as FR3, and a region between CDR3 and the C-terminal of the variable region is defined as FR4.

FR also functions as a linker sequence linking the CDRs 1-3 which are particularly important as an antigen recognition sequence. FR is a region that contributes to the formation of a three-dimensional structure of the entire variable region.

In the present specification, various Claudin proteins will be described as "X CLDN-Y" or "X CLDN-Y protein" in some cases. X represents the origin species (h: human, c: crab-eating macaque, m: mouse), and Y represents Claudin protein number. For example, a human Claudin-5 protein is described as "hCLDN-5" or "hCLDN-5 protein".

2. Antibody

As an embodiment, the present invention relates to an antibody which specifically recognizes a three-dimensional structure or a primary structure of an extracellular domain of a CLDN-5 protein (in the present specification, the antibody will be described as "antibody according to an embodiment of the present invention" or "CLDN-5 extracellular domain antibody" or simply described as "anti-CLDN-5 antibody" or the like in some cases). Hereinafter, the antibody will be described.

The Claudin-5 protein is a gene expression product of Claudin-5 (referred to as CLDN-5, Cldn-5, CLDN5, Cldn5, or the like in some cases) that is a CLDN-5 protein expressed in a living organism. The origin species of the CLDN-5 protein is not particularly limited, and examples thereof include animals such as various mammals including a human being, a monkey, a mouse, a rat, a dog, a cat, a rabbit, a pig, a horse, a cow, a goat, a lamb, and a deer. Among these, a human being, a monkey (particularly a crab-eating macaque), and the like are preferable.

Amino acid sequences of CLDN-5 proteins derived from various species are known. Specifically, examples of human CLDN-5 proteins include a protein consisting of an amino acid sequence represented by SEQ ID NO: 27 and the like. Examples of crab-eating macaque CLDN-5 proteins include a protein consisting of an amino acid sequence represented by SEQ ID NO: 28 and the like. Examples of mouse CLDN-5 proteins include a protein consisting of an amino acid sequence represented by SEQ ID NO: 29 and the like.

As long as the original activity of the CLDN-5 protein is maintained, and the CLDN-5 protein is capable of forming a tight junction by interacting with each other through the extracellular loops thereof, the CLDN-5 protein may have an amino acid mutation such as substitution, deletion, addition, or insertion. As the mutation, from the viewpoint of further preventing the deterioration of activity, substitution is preferable, and conservative substitution is more preferable.

Specifically, as the CLDN-5 protein, for example, at least one kind of protein is preferable which is selected from the group consisting of a protein described below in (a) and a protein described below in (b):

(a) protein consisting of an amino acid sequence represented by any one of SEQ ID NO: 27, 28, or 29, and (b) protein which consists of an amino acid sequence sharing identity equal to or higher than 85% with the amino acid sequence represented by any one of SEQ ID NO: 27, 28, or 29 and has an ability to form a tight junction.

In (a) and (b) described above, amino acid sequences represented by SEQ ID NOS: 27 and 28 are preferable.

In (b) described above, the identity is more preferably equal to or higher than 90%, even more preferably equal to or higher than 95%, and still more preferably equal to or higher than 98%.

One of the examples of the protein described above in (b) is (b') protein that consists of an amino acid sequence, which has the substitution, deletion, addition, or insertion of one amino acid or a plurality of amino acids in the amino acid sequence represented by any one of SEQ ID NO: 27, 28, or 29, and has an hydrolytic activity on inositol phosphate bond. In (b) described above, the number of plurality of amino acids is 2 to 20 for example, preferably 2 to 10, more preferably 2 to 5, and even more preferably 2 or 3.

The extracellular domain of the CLDN-5 protein is not particularly limited as long as it is a region where the CLDN-5 protein is exposed to the outside of a cell in a state of being disposed in the cell membrane (preferably an endothelial cell membrane or a vascular endothelial cell membrane and more preferably a brain capillary endothelial cell membrane) by crossing the cell membrane 4 times. Furthermore, the extracellular domain of the CLDN-5 protein includes a first extracellular loop present on the N-terminal side and a second extracellular loop present on the C-terminal side. The extracellular domain, the first extracellular loop, and the second extracellular loop of each CLDN-5 protein are known, or can be easily determined using various transmembrane domain prediction tools (for example, SOSUI: harrier.nagahama-i-bio.ac.jp/sosui/) and the like.

Specifically, in a human CLDN-5 protein consisting of an amino acid sequence represented by SEQ ID NO: 27, for example, a domain (first extracellular loop) ranging from the $28^{th}$ amino acid (proline) to the $80^{th}$ amino acid (alanine) from the N-terminal and a domain (second extracellular loop) ranging from the 147th amino acid (phenylalanine) to the $163^{rd}$ amino acid (alanine) from the N-terminal are extracellular domains. In other CLDN-5 proteins, specific examples of extracellular domains include domains corresponding to the above. In the present specification, "corresponding domains" are domains found to correspond to the above in a case where the amino acid sequence of the human CLDN-5 protein and another CLDN-5 amino acid sequence are compared with each other by using a sequence analysis tool (PASTA. BLAST, or the like).

The antibody according to the embodiment of the present invention specifically recognizes the three-dimensional structure or the primary structure of the extracellular domain of the CLDN-5 protein. In other words, the antibody according to the embodiment of the present invention binds or is capable of binding to the three-dimensional structure or the primary structure of the extracellular domain of the CLDN-5 protein.

In a case where the recognition domain of the antibody according to the embodiment of the present invention is a primary structure, the recognition domain is consecutive amino acid sequences. In a case where the recognition domain of the antibody according to the embodiment of the present invention is a three-dimensional structure, the recognition domain may be consecutive amino acid sequences or a plurality of inconsecutive amino acid sequences.

The number of amino acid residues constituting the recognition domain of the antibody according to the embodiment of the present invention is not particularly limited, and is, for example, equal to or smaller than 40, equal to or smaller than 35, 6 to 30, 6 to 25, 6 to 20, 6 to 15, or 6 to 10.

Specifically, examples of domains preferred as the recognition domain of the antibody according to the embodiment of the present invention include a domain in the first extracellular loop (a primary structure or a three-dimensional structure), a domain in the second extracellular loop (a primary structure or a three-dimensional structure), a three-dimensional structure formed of the first extracellular loop and/or the second extracellular loop, and the like. Specifically examples of more preferred domains include a domain in the second extracellular loop (a primary structure or a three-dimensional structure).

Examples of the domain in the first extracellular loop, which is a specific example preferred as the recognition domain of the antibody according to the embodiment of the present invention, include a domain ranging from the $28^{th}$ amino acid (proline) to the $80^{th}$ amino acid (alanine) from the N-terminal in the human CLDN-5 protein consisting of the amino acid sequence represented by SEQ ID NO: 27. Preferred examples thereof include a domain which contains the $68^{th}$ amino acid (aspartic acid) from the N-terminal. In other CLDN-5 proteins, specific examples of the recognition domain include domains corresponding to the above.

Examples of the domain in the second extracellular loop, which is a specific example preferred as the recognition domain of the antibody according to the embodiment of the present invention, include a domain ranging from the 147$^{th}$ amino acid (phenylalanine) to the 163$^{rd}$ amino acid (alanine) from the N-terminal in the human CLDN-5 protein consisting of the amino acid sequence represented by SEQ ID NO: 27, Preferred examples thereof include a domain which contains the 151$^{st}$ amino acid (serine) from the N-terminal. In other CLDN-5 proteins, specific examples of the recognition domain include domains corresponding to the above.

In a case where the antibody according to the embodiment of the present invention recognizes the domain in the first extracellular loop as a recognition domain and is an antibody against the human CLDN-5 protein as a preferred embodiment, examples thereof include an antibody of which a binding capacity to a protein (1-1-5: Example 3-4), which consists of an amino acid sequence represented by SEQ ID NO: 45 and is the one where the first extracellular loop of the human CLDN-5 protein is substituted with a sequence of a human CLDN-1 protein, is equal to or lower than 1/5, 1/20, 1/100, 1/500, 1/2,000, or 1/10,000 of a binding capacity thereof to the human CLDN-5 protein consisting of the amino acid sequence represented by SEQ ID NO: 27.

In a case where the antibody according to the embodiment of the present invention recognizes the domain in the first extracellular loop as a recognition domain and is an antibody against the human CLDN-5 protein as a preferred embodiment, examples thereof include an antibody of which a binding capacity to a human CLDN-5 protein point mutant D68E (Example 3-5) consisting of an amino acid sequence represented by SEQ ID NO: 41 is equal to or lower than 1/5, 1/20, 1/100, 1/500, 1/2,000, or 1/10,000 of a binding capacity thereof to the human CLDN-5 protein consisting of the amino acid sequence represented by SEQ ID NO: 27.

In a case where the antibody according to the embodiment of the present invention is an antibody against the human CLDN-5 protein that recognizes the domain in the first extracellular loop as a recognition domain, as a preferred embodiment, examples thereof include an antibody having a binding capacity to a protein (5-5-1: Example 3-4) which consists of an amino acid sequence represented by SEQ ID NO: 48 and is the one where the second extracellular loop of the human CLDN-5 protein is substituted with the sequence of the human CLDN-1 protein.

In a case where the antibody according to the embodiment of the present invention recognizes the domain in the second extracellular loop as a recognition domain and is an antibody against the human CLDN-5 protein as a preferred embodiment, examples thereof include an antibody of which a binding capacity to the protein (5-5-1: Example 3-4), which consists of the amino acid sequence represented by SEQ ID NO: 48 and is the one where the second extracellular loop of the human CLDN-5 protein is substituted with the sequence of the human CLDN-1 protein, is equal to or lower than 1/5, 1/20, 1/100, 1/500, 1/2,000, or 1/10,000 of a binding capacity thereof to the human CLDN-5 protein consisting of the amino acid sequence represented by SEQ ID NO: 27.

In a case where the antibody according to the embodiment of the present invention recognizes the domain in the second extracellular loop as a recognition domain and is an antibody against the human CLDN-5 protein as a preferred embodiment, examples thereof include an antibody of which a binding capacity to a human CLDN-5 protein point mutant S151T (Example 3-5) consisting of an amino acid sequence represented by SEQ ID NO: 43 is equal to or lower than 1/5, 1/20, 1/100, 1/500, 1/2,000, or 1/10,000 of a binding capacity thereof to the human CLDN-5 protein consisting of the amino acid sequence represented by SEQ ID NO: 27.

In a case where the antibody according to the embodiment of the present invention is an antibody against the human CLDN-5 protein that recognizes the domain in the second extracellular loop as a recognition domain, as a preferred embodiment, examples thereof include an antibody having a binding capacity to the protein (1-1-5: Example 3-4) which consists of the amino acid sequence represented by SEQ ID NO: 45 and is the one where the first extracellular loop of the human CLDN-5 protein is substituted with the sequence of the human CLDN-1 protein.

It should be noted that the binding capacity of a test antibody to a target CLDN protein can be investigated by staining a cell supposed to express the target CLDN protein with fluorescence by using the test antibody (or a solution used for diluting the antibody) and performing FACS assay on the fluorescence-stained cell in the same manner as in Example 1-4, The sum of fluorescence signals from the cell can be regarded as the binding capacity of the test antibody to the target CLDN protein. In a case where the sum of fluorescence signals obtained using the test antibody is equal to or greater than the sum of fluorescence signals obtained using a dilution of the antibody (Vehicle) by 1.5 folds, 2 folds, 5 folds, 10 folds, 20 folds, 50 folds, 100 folds, 200 folds, 500 folds, 1,000 folds, 5,000 folds, or 10,000 folds, it is possible to determine that the test antibody has "binding capacity" to the target protein. Regarding the binding capacity, the same is true for the following description.

Examples of the three-dimensional structure formed of the first extracellular loop and/or the second extracellular loop that is a specific example preferred as the recognition domain of the antibody according to the embodiment of the present invention include a three-dimensional structure formed of a domain ranging from the 28$^{th}$ amino acid (proline) to the 80$^{th}$ amino acid (alanine) from the N-terminal in the human CLDN-5 protein consisting of the amino acid sequence represented by SEQ ID NO: 27 and a domain ranging from the 147$^{th}$ amino acid (phenylalanine) to the 163$^{rd}$ amino acid (alanine) from the N-terminal in the same human CLDN-5 protein. For example, the three-dimensional structure is preferably a three-dimensional structure formed of a domain ranging from the 28$^{th}$ amino acid (proline) to the 67$^{th}$ amino acid (tyrosine) from the N-terminal and the domain ranging from the 147$^{th}$ amino acid (phenylalanine) to the 163$^{rd}$ amino acid (alanine) from the N-terminal, more preferably a three-dimensional structure formed of a domain ranging from the 28$^{th}$ amino acid (proline) to the 55$^{th}$ amino acid (valine) from the N-terminal and the domain ranging from the 147$^{th}$ amino acid (phenylalanine) to the 163$^{rd}$ amino acid (alanine) from the N-terminal, and even more preferably a three-dimensional structure formed of a domain ranging from the 28$^{th}$ amino acid (proline) to the 48$^{th}$ amino acid (lysine) from the N-terminal and the domain ranging from the 147th amino acid (phenylalanine) to the 163$^{rd}$ amino acid (alanine) from the N-terminal. In other CLDN-5 proteins, specific examples of the recognition domain include domains corresponding to the above.

In a case where the antibody according to the embodiment of the present invention recognizes a three-dimensional structure formed of the first extracellular loop and/or the second extracellular loop as a recognition domain and is an antibody against the human CLDN-5 protein as a preferred embodiment, examples thereof include an antibody of which a binding capacity to a mutant (TM: Example 3-5), which consists of an amino acid sequence represented by SEQ ID NO: 44 and is the one where an amino acid of mouse CLDN-5 is introduced into a transmembrane domain of the human CLDN-5 protein, is equal to or lower than 1/5, 1/20, 1/100, 1/500, 1/2,000, or 1/10,000 of a binding capacity thereof to the human CLDN-5 protein consisting of the amino acid sequence represented by SEQ ID NO: 27.

In a case where the antibody according to the embodiment of the present invention is an antibody against the human CLDN-5 protein that recognizes a three-dimensional structure formed of the first extracellular loop and/or the second extracellular loop as a recognition domain, as a preferred embodiment, examples thereof include an antibody of which a binding capacity to a human CLDN-5 protein mutant (1-5-5 and 5-1-5: Example 3-4) consisting of an amino acid sequences represented by SEQ ID NOS: 46 and 47 is equal to or lower than 1/5, 1/20, 1/100, 1/500, 1/2,000, or 1/10,000 of a binding capacity thereof to the human CLDN-5 protein consisting of the amino acid sequence represented by SEQ ID NO: 27.

It is preferable that the antibody according to the embodiment of the present invention has higher binding specificity to the CLDN-5 protein. In a case where the antibody has higher binding specificity to the CLDN-5 protein, it is possible to further reduce the side effects caused by the opening of a tight junction other than the blood-brain barrier. In this respect, as the antibody according to the embodiment of the present invention, for example, an antibody is preferable of which a binding capacity to a CLDN family protein other than the CLDN-5 protein is equal to or lower than 1/5 of a binding capacity thereof to the CLDN-5 protein.

Examples of "CLDN family protein other than the CLDN-5 protein" as a comparison target for determining the binding capacity include CLDN-1, CLDN-3, CLDN-4, CLDN-6, CLDN-7, and the like in a case where the CLDN family protein is a human protein. In a case where the CLDN family protein is a mouse protein, examples thereof include CLDN-1, CLDN-2, CLDN-3, CLDN-4, and the like. For determining the binding capacity, as a comparison target, one kind of CLDN family protein may be used singly, two or more kinds of CLDN family proteins may be used in any combination, or all the CLDN family proteins may be used.

From the viewpoint of specificity to the CLDN-5 protein, it is preferable that the antibody according to the embodiment of the present invention binds to none of the extracellular domains of human and mouse CLDN-1 proteins, human and mouse CLDN-2 proteins, human and mouse CLDN-3 proteins, human and mouse CLDN-4 proteins, a human CLDN-6 protein, and a human CLDN-7 protein.

A dissociation constant (Kd) of the antibody according to the embodiment of the present invention is not particularly limited. Kd is equal to or smaller than $1\times10^{-7}$ (M for example, preferably equal to or smaller than $3\times10^{-8}$ (M), more preferably equal to or smaller than $1\times10^{-8}$ (M), and even more preferably equal to or smaller than $5\times10^{-9}$ (M).

As the antibody according to the embodiment of the present invention, from the viewpoint of binding capacity to the CLDN-5 protein, blood-brain barrier control activity, and the like, for example, the following antibodies A to M are preferable. As the antibodies A to M, for example, a mouse anti-CLDN-5 antibody 5 clone and a rat anti-CLDN-5 antibody 8 clone are preferable. The antibodies are named M3, M11, M23, M29, M48, R2, R3, R8, R9, R11, R14, R20, and R28 based on the names of hybridoma clones of the antibodies. Among these, M48 and R9 are preferable. Hereinafter, the antibodies A to M will be described.

Antibody A

The antibody A contains a heavy chain variable region which contains a heavy chain CDR1 having an amino acid sequence represented by SEQ ID NO: 50 or an amino acid sequence sharing identity equal to or higher than 95% with the amino acid sequence represented by SEQ ID NO: 50, a heavy chain CDR2 having an amino acid sequence represented by SEQ ID NO: 52 or an amino acid sequence sharing identity equal to or higher than 95% with the amino acid sequence represented by SEQ ID NO: 52, and a heavy chain CDR3 having an amino acid sequence represented by SEQ ID NO: 54 or an amino acid sequence sharing identity equal to or higher than 95% with the amino acid sequence represented by SEQ ID NO: 54 and/or a light chain variable region containing a light chain CDR1 having an amino acid sequence represented by SEQ ID NO: 141 or an amino acid sequence sharing identity equal to or higher than 95% with the amino acid sequence represented by SEQ ID NO: 141, a light chain CDR2 having an amino acid sequence represented by SEQ ID NO: 143 or an amino acid sequence sharing identity equal to or higher than 95% with the amino acid sequence represented by SEQ ID NO: 143, and a light chain CDR3 having an amino acid sequence represented by SEQ ID NO: 145 or an amino acid sequence sharing identity equal to or higher than 95% with the amino acid sequence represented by SEQ ID NO: 145.

The antibody A just needs to contain at least the heavy chain and light chain CDRs 1 to 3, and may further contain FR of the heavy chain variable region and the light chain variable region. Examples of sequences of FR1 to FR4 of the heavy chain variable region, sequences of FR1 to FR4 of the light chain variable region, a complete sequence of the heavy chain variable region, and a complete sequence of the light chain variable region include sequences of the antibody M3 described in Tables 2 and 4 or amino acid sequences sharing identity equal to or higher than 95% with the above sequences. More specifically, examples of the antibody A include the antibody M3.

M3

The mouse anti-CLDN-5 antibody M3 has an amino acid sequence represented by SEQ ID NO: 1 as the complete sequence of the heavy chain variable region (sequence in which FR1. CDR1, FR2, CDR2. FR3, CDR3, and FR4 are arranged in this order from the N-terminal side), and has an amino acid sequence represented by SEQ ID NO: 2 as the complete sequence of the light chain variable region (sequence in which FR1, CDR1, FR2, CDR2, FR3, CDR3, and FR4 are arranged in this order from the N-terminal side). Presumably, this antibody may recognize the three-dimensional structure of the second extracellular loop. Furthermore, presumably, this antibody may recognize the three-dimensional structure created by the transmembrane domain of hCLDN-5.

Antibody B

The antibody B contains a heavy chain variable region containing a heavy chain CDR1 having an amino acid sequence represented by SEQ ID NO: 57 or an amino acid sequence sharing identity equal to or higher than 95% with the amino acid sequence represented by SEQ ID NO: 57, a heavy chain CDR2 having an amino acid sequence represented by SEQ ID NO: 59 or an amino acid sequence sharing identity equal to or higher than 95% with the amino acid sequence represented by SEQ ID NO: 59, and a heavy chain CDR3 having an amino acid sequence represented by SEQ ID NO: 61 or an amino acid sequence sharing identity equal to or higher than 95% with the amino acid sequence represented by SEQ ID NO: 61 and/or a light chain variable region containing a light chain CDR1 having an amino acid sequence represented by SEQ ID NO: 148 or an amino acid sequence sharing identity equal to or higher than 95% with the amino acid sequence represented by SEQ ID NO: 148, a light chain CDR2 having an amino acid sequence represented by SEQ ID NO: 150 or an amino acid sequence sharing identity equal to or higher than 95% with the amino acid sequence represented by SEQ ID NO: 150, and a light chain CDR3 having an amino acid sequence represented by SEQ ID NO: 152 or an amino acid sequence sharing identity equal to or higher than 95% with the amino acid sequence represented by SEQ ID NO: 152.

The antibody B just needs to contain at least the heavy chain and light chain CDRs 1 to 3, and may further contain FR of the heavy chain variable region and the light chain variable region. Examples of sequences of FR1 to FR4 of the heavy chain variable region, sequences of FR1 to FR4 of the light chain variable region, a complete sequence of the heavy chain variable region, and a complete sequence of the light chain variable region include sequences of the antibody M11 described in Tables 2 and 4 or amino acid sequences sharing identity equal to or higher than 95% with the above sequences. More specifically, examples of the antibody B include the antibody M11.

M11

The mouse anti-CLDN-5 antibody M11 has an amino acid sequence represented by SEQ ID NO: 3 as the complete sequence of the heavy chain variable region (sequence in which FR1, CDR1, FR2, CDR2, FR3. CDR3, and FR4 are arranged in this order from the N-terminal side), and has an amino acid sequence represented by SEQ ID NO: 4 as the complete sequence of the light chain variable region (sequence in which FR1, CDR1, FR2, CDR2, FR3, CDR3, and FR4 are arranged in this order from the N-terminal side). Presumably, this antibody may recognize the three-dimensional structure of the first extracellular loop.

Antibody C

The antibody C contains a heavy chain variable region containing a heavy chain CDR1 having an amino acid sequence represented by SEQ ID NO: 64 or an amino acid sequence sharing identity equal to or higher than 95% with the amino acid sequence represented by SEQ ID NO: 64, a heavy chain CDR2 having an amino acid sequence represented by SEQ ID NO: 66 or an amino acid sequence sharing identity equal to or higher than 95% with the amino acid sequence represented by SEQ ID NO: 66, and a heavy chain CDR3 having an amino acid sequence represented by SEQ ID NO: 68 or an amino acid sequence sharing identity equal to or higher than 95% with the amino acid sequence represented by SEQ ID NO: 68 and/or a light chain variable region containing a light chain CDR1 having an amino acid sequence represented by SEQ ID NO: 155 or an amino acid sequence sharing identity equal to or higher than 95% with the amino acid sequence represented by SEQ ID NO: 155, a light chain CDR2 having an amino acid sequence represented by SEQ ID NO: 157 or an amino acid sequence sharing identity equal to or higher than 95% with the amino acid sequence represented by SEQ ID NO: 157, and a light chain CDR3 having an amino acid sequence represented by SEQ ID NO: 159 or an amino acid sequence sharing identity equal to or higher than 95% with the amino acid sequence represented by SEQ ID NO: 159.

The antibody C just needs to contain at least the heavy chain and light chain CDRs 1 to 3, and may further contain FR of the heavy chain variable region and the light chain variable region. Examples of sequences of FR1 to FR4 of the heavy chain variable region, sequences of FR1 to FR4 of the light chain variable region, a complete sequence of the heavy chain variable region, and a complete sequence of the light chain variable region include sequences of the antibody M23 described in Tables 2 and 4 or amino acid sequences sharing identity equal to or higher than 95% with the above sequences. More specifically, examples of the antibody C include the antibody M23.

M23

The mouse anti-CLDN-5 antibody M23 has an amino acid sequence represented by SEQ ID NO: 5 as the complete sequence of the heavy chain variable region (sequence in which FR1, CDR1, FR2, CDR2, FR3, CDR3, and FR4 are arranged in this order from the N-terminal side), and has an amino acid sequence represented by SEQ ID NO: 6 as the complete sequence of the light chain variable region (sequence in which FR1, CDR1, FR2, CDR2, FR3, CDR3, and FR4 are arranged in this order from the N-terminal side). Presumably, this antibody may recognize the three-dimensional structure of the second extracellular loop.

Antibody D

The antibody D contains a heavy chain variable region containing a heavy chain CDR1 having an amino acid sequence represented by SEQ ID NO: 71 or an amino acid sequence sharing identity equal to or higher than 95% with the amino acid sequence represented by SEQ ID NO: 71, a heavy chain CDR2 having an amino acid sequence represented by SEQ ID NO: 73 or an amino acid sequence sharing identity equal to or higher than 95% with the amino acid sequence represented by SEQ ID NO: 73, and a heavy chain CDR3 having an amino acid sequence represented by SEQ ID NO: 75 or an amino acid sequence sharing identity equal to or higher than 95% with the amino acid sequence represented by SEQ ID NO: 75 and/or a light chain variable region containing a light chain CDR1 having an amino acid sequence represented by SEQ ID NO: 162 or an amino acid sequence sharing identity equal to or higher than 95% with the amino acid sequence represented by SEQ ID NO: 162, a light chain CDR2 having an amino acid sequence represented by SEQ ID NO: 164 or an amino acid sequence sharing identity equal to or higher than 95% with the amino acid sequence represented by SEQ ID NO: 164, and a light chain CDR3 having an amino acid sequence represented by SEQ ID NO: 166 or an amino acid sequence sharing identity equal to or higher than 95% with the amino acid sequence represented by SEQ ID NO: 166.

The antibody D just needs to contain at least the heavy chain and light chain CDRs 1 to 3, and may further contain FR of the heavy chain variable region and the light chain variable region. Examples of sequences of FR1 to FR4 of the heavy chain variable region, sequences of FIR to FR4 of the light chain variable region, a complete sequence of the heavy chain variable region, and a complete sequence of the light chain variable region include sequences of the antibody M29 described in Tables 2 and 4 or amino acid sequences sharing identity equal to or higher than 95% with the above sequences. More specifically, examples of the antibody D include the antibody M29.

M29

The mouse anti-CLDN-5 antibody M29 has an amino acid sequence represented by SEQ ID NO: 7 as the complete sequence of the heavy chain variable region (sequence in which FR1, CDR1, FR2. CDR2, FR3, CDR3, and FR4 are arranged in this order from the N-terminal side), and has an amino acid sequence represented by SEQ ID NO: 8 as the complete sequence of the light chain variable region (sequence in which FR1, CDR1, FR2, CDR2, FR3, CDR3, and FR4 are arranged in this order from the N-terminal side). Presumably, this antibody may recognize the second extracellular loop.

Antibody E

The antibody E contains a heavy chain variable region containing a heavy chain CDR1 having an amino acid sequence represented by SEQ ID NO: 78 or an amino acid sequence sharing identity equal to or higher than 95% with the amino acid sequence represented by SEQ ID NO: 78, a heavy chain CDR2 having an amino acid sequence represented by SEQ ID NO: 80 or an amino acid sequence sharing identity equal to or higher than 95% with the amino acid sequence represented by SEQ ID NO: 80, and a heavy chain CDR3 having an amino acid sequence represented by SEQ ID NO: 82 or an amino acid sequence sharing identity equal to or higher than 95% with the amino acid sequence represented by SEQ ID NO: 82 and/or a light chain variable region containing a light chain CDR1 having an amino acid sequence represented by SEQ ID NO: 169 or an amino acid sequence sharing identity equal to or higher than 95% with the amino acid sequence represented by SEQ ID NO: 169, a light chain CDR2 having an amino acid sequence represented by SEQ ID NO: 171 or an amino acid sequence sharing identity equal to or higher than 95% with the amino acid sequence represented by SEQ ID NO: 171, and a light chain CDR3 having an amino acid sequence represented by SEQ ID NO: 173 or an amino acid sequence sharing identity equal to or higher than 95% with the amino acid sequence represented by SEQ ID NO: 173.

The antibody E just needs to contain at least the heavy chain and light chain CDRs 1 to 3, and may further contain FR of the heavy chain variable region and the light chain variable region. Examples of sequences of FR1 to FR4 of the heavy chain variable region, sequences of FR1 to FR4 of the light chain variable region, a complete sequence of the heavy chain variable region, and a complete sequence of the light chain variable region include sequences of the antibody M48 described in Tables 2 and 4 or amino acid sequences sharing identity equal to or higher than 95% with the above sequences. More specifically, examples of the antibody E include the antibody M48.

M48

The mouse anti-CLDN-5 antibody M48 has an amino acid sequence represented by SEQ ID NO: 9 as the complete sequence of the heavy chain variable region (sequence in which FR1, CDR1, FR2, CDR2, FR3, CDR3, and FR4 are arranged in this order from the N-terminal side), and has an amino acid sequence represented by SEQ ID NO: 10 as the complete sequence of the light chain variable region (sequence in which FR1, CDR1, FR2, CDR2, FR3, CDR3, and FR4 are arranged in this order from the N-terminal side). Presumably, this antibody may recognize the three-dimensional structure of the second extracellular loop.

Antibody F

The antibody F contains a heavy chain variable region containing a heavy chain CDR1 having an amino acid sequence represented by SEQ ID NO: 85 or an amino acid sequence sharing identity equal to or higher than 95% with the amino acid sequence represented by SEQ ID NO: 85, a heavy chain CDR2 having an amino acid sequence represented by SEQ ID NO: 87 or an amino acid sequence sharing identity equal to or higher than 95% with the amino acid sequence represented by SEQ ID NO: 87, and a heavy chain CDR3 having an amino acid sequence represented by SEQ ID NO: 89 or an amino acid sequence sharing identity equal to or higher than 95% with the amino acid sequence represented by SEQ ID NO: 89 and/or a light chain variable region containing a light chain CDR1 having an amino acid sequence represented by SEQ ID NO: 176 or an amino acid sequence sharing identity equal to or higher than 95% with the amino acid sequence represented by SEQ ID NO: 176, a light chain CDR2 having an amino acid sequence represented by SEQ ID NO: 178 or an amino acid sequence sharing identity equal to or higher than 95% with the amino acid sequence represented by SEQ ID NO: 178, and a light chain CDR3 having an amino acid sequence represented by SEQ ID NO: 180 or an amino acid sequence sharing identity equal to or higher than 95% with the amino acid sequence represented by SEQ ID NO: 180.

The antibody F just needs to contain at least the heavy chain and light chain CDRs 1 to 3, and may further contain FR of the heavy chain variable region and the light chain variable region. Examples of sequences of FR1 to FR4 of the heavy chain variable region, sequences of FR1 to FR4 of the light chain variable region, a complete sequence of the heavy chain variable region, and a complete sequence of the light chain variable region include sequences of the antibody R2 described in Tables 2 and 4 or amino acid sequences sharing identity equal to or higher than 95% with the above sequences. More specifically, examples of the antibody F include the antibody R2.

R2

The rat anti-CLDN-5 antibody R2 has an amino acid sequence represented by SEQ ID NO: 11 as the complete sequence of the heavy chain variable region (sequence in which FR1, CDR1, FR2, CDR2, FR3, CDR3, and FR4 are arranged in this order from the N-terminal side), and has an amino acid sequence represented by SEQ ID NO: 12 as the complete sequence of the light chain variable region (sequence in which FR1, CDR1, FR2, CDR2, FR3, CDR3, and FR4 are arranged in this order from the N-terminal side). Presumably, this antibody may recognize the three-dimensional structure of the first extracellular loop.

Antibody G

The antibody G contains a heavy chain variable region containing a heavy chain CDR1 having an amino acid sequence represented by SEQ ID NO: 92 or an amino acid sequence sharing identity equal to or higher than 95% with the amino acid sequence represented by SEQ ID NO 92, a heavy chain CDR2 having an amino acid sequence represented by SEQ ID NO: 94 or an amino acid sequence sharing identity equal to or higher than 95% with the amino acid sequence represented by SEQ II) NO: 94, and a heavy chain CDR3 having an amino acid sequence represented by SEQ ID NO: 96 or an amino acid sequence sharing identity equal to or higher than 95% with the amino acid sequence represented by SEQ ID NO: 96 and/or a light chain variable region containing a light chain CDR1 having an amino acid sequence represented by SEQ ID NO: 183 or an amino acid sequence sharing identity equal to or higher than 95% with the amino acid sequence represented by SEQ ID NO: 183, a light chain CDR2 having an amino acid sequence represented by SEQ ID NO: 185 or an amino acid sequence sharing identity equal to or higher than 95% with the amino acid sequence represented by SEQ ID NO: 185, and a light chain CDR3 having an amino acid sequence represented by SEQ ID NO: 187 or an amino acid sequence sharing identity equal to or higher than 95% with the amino acid sequence represented by SEQ ID NO: 187.

The antibody G just needs to contain at least the heavy chain and light chain CDRs 1 to 3, and may further contain FR of the heavy chain variable region and the light chain variable region. Examples of sequences of FR1 to FR4 of the heavy chain variable region, sequences of FR1 to FR4 of the light chain variable region, a complete sequence of the heavy chain variable region, and a complete sequence of the light chain variable region include sequences of the antibody R3 described in Tables 2 and 4 or amino acid sequences sharing identity equal to or higher than 95% with the above sequences. More specifically, examples of the antibody G include the antibody R3.

R3

The rat anti-CLDN-5 antibody R3 has an amino acid sequence represented by SEQ ID NO: 13 as the complete sequence of the heavy chain variable region (sequence in which FR1, CDR1, FR2, CDR2, FR3, CDR3, and FR4 are arranged in this order from the N-terminal side), and has an amino acid sequence represented by SEQ ID NO: 14 as the complete sequence of the light chain variable region (sequence in which FR1, CDR1, FR2, CDR2, FR3, CDR3, and FR4 are arranged in this order from the N-terminal side). Presumably, this antibody may recognize the three-dimensional structure of the second extracellular loop.

Antibody H

The antibody H contains a heavy chain variable region containing a heavy chain CDR1 having an amino acid sequence represented by SEQ ID NO: 99 or an amino acid sequence sharing identity equal to or higher than 95% with the amino acid sequence represented by SEQ ID NO: 99, a heavy chain CDR2 having an amino acid sequence represented by SEQ ID NO: 101 or an amino acid sequence sharing identity equal to or higher than 95% with the amino acid sequence represented by SEQ ID NO: 101, and a heavy chain CDR3 having an amino acid sequence represented by SEQ ID NO: 103 or an amino acid sequence sharing identity equal to or higher than 95% with the amino acid sequence represented by SEQ ID NO: 103 and/or a light chain variable region containing a light chain CDR1 having an amino acid sequence represented by SEQ ID NO: 190 or an amino acid sequence sharing identity equal to or higher than 95% with the amino acid sequence represented by SEQ ID NO: 190, a light chain CDR2 having an amino acid sequence represented by SEQ ID NO: 192 or an amino acid sequence sharing identity equal to or higher than 95% with the amino acid sequence represented by SEQ ID NO: 192, and a light chain CDR3 having an amino acid sequence represented by SEQ ID NO: 194 or an amino acid sequence sharing identity equal to or higher than 95% with the amino acid sequence represented by SEQ ID NO: 194.

The antibody H just needs to contain at least the heavy chain and light chain CDRs 1 to 3, and may further contain FR of the heavy chain variable region and the light chain variable region. Examples of sequences of FR1 to FR4 of the heavy chain variable region, sequences of FR1 to FR4 of the light chain variable region, a complete sequence of the heavy chain variable region, and a complete sequence of the light chain variable region include sequences of the antibody R8 described in Tables 3 and 5 or amino acid sequences sharing identity equal to or higher than 95% with the above sequences. More specifically, examples of the antibody H include the antibody R8.

R8

The rat anti-CLDN-5 antibody R8 has an amino acid sequence represented by SEQ ID NO: 15 as the complete sequence of the heavy chain variable region (sequence in which FR1, CDR1, FR2, CDR2, FR3, CDR3, and FR4 are arranged in this order from the N-terminal side), and has an amino acid sequence represented by SEQ ID NO: 16 as the complete sequence of the light chain variable region (sequence in which FR1. CDR1, CDR2, FR3, CDR3, and FR4 are arranged in this order from the N-terminal side).

Antibody I

The antibody I contains a heavy chain variable region containing a heavy chain CDR1 having an amino acid sequence represented by SEQ ID NO: 106 or an amino acid sequence sharing identity equal to or higher than 95% with the amino acid sequence represented by SEQ ID NO: 106, a heavy chain CDR2 having an amino acid sequence represented by SEQ ID NO: 108 or an amino acid sequence sharing identity equal to or higher than 95% with the amino acid sequence represented by SEQ ID NO: 108, and a heavy chain CDR3 having an amino acid sequence represented by SEQ ID NO: 110 or an amino acid sequence sharing identity equal to or higher than 95% with the amino acid sequence represented by SEQ ID NO: 110 and/or a light chain variable region containing a light chain CDR1 having an amino acid sequence represented by SEQ ID NO: 197 or an amino acid sequence sharing identity equal to or higher than 95% with the amino acid sequence represented by SEQ ID NO: 197, a light chain CDR2 having an amino acid sequence represented by SEQ ID NO: 199 or an amino acid sequence sharing identity equal to or higher than 95% with the amino acid sequence represented by SEQ ID NO: 199, and a light chain CDR3 having an amino acid sequence represented by SEQ ID NO: 201 or an amino acid sequence sharing identity equal to or higher than 95% with the amino acid sequence represented by SEQ ID NO: 201.

The antibody I just needs to contain at least the heavy chain and light chain CDRs 1 to 3, and may further contain FR of the heavy chain variable region and the light chain variable region. Examples of sequences of FR1 to FR4 of the heavy chain variable region, sequences of FR1 to FR4 of the light chain variable region, a complete sequence of the heavy chain variable region, and a complete sequence of the light chain variable region include sequences of the antibody R9 described in Tables 3 and 5 or amino acid sequences sharing identity equal to or higher than 95% with the above sequences. More specifically, examples of the antibody I include the antibody R9.

R9

The rat anti-CLDN-5 antibody R9 has an amino acid sequence represented by SEQ ID NO: 17 as the complete sequence of the heavy chain variable region (sequence in which FR1, CDR1, FR2, CDR2, FR3, CDR3, and FR4 are arranged in this order from the N-terminal side), and has an amino acid sequence represented by SEQ ID NO: 18 as the complete sequence of the light chain variable region (sequence in which FR1, CDR1, FR2. CDR2, FR3, CDR3, and FR4 are arranged in this order from the N-terminal side). Presumably, this antibody may recognize the primary structure of the second extracellular loop.

Antibody J

The antibody J contains a heavy chain variable region containing a heavy chain CDR1 having an amino acid sequence represented by SEQ ID NO: 113 or an amino acid sequence sharing identity equal to or higher than 95% with the amino acid sequence represented by SEQ ID NO: 113, a heavy chain CDR2 having an amino acid sequence represented by SEQ ID NO: 115 or an amino acid sequence sharing identity equal to or higher than 95% with the amino acid sequence represented by SEQ ID NO: 115, and a heavy chain CDR3 having an amino acid sequence represented by SEQ ID NO: 117 or an amino acid sequence sharing identity equal to or higher than 95% with the amino acid sequence represented by SEQ ID NO: 117 and/or a light chain variable region containing a light chain CDR1 having an amino acid sequence represented by SEQ ID NO: 204 or an amino acid sequence sharing identity equal to or higher than 95% with the amino acid sequence represented by SEQ ID NO: 204, a light chain CDR2 having an amino acid sequence represented by SEQ ID NO: 206 or an amino acid sequence sharing identity equal to or higher than 95% with the amino acid sequence represented by SEQ ID NO: 206, and a light chain CDR3 having an amino acid sequence represented by SEQ ID NO: 208 or an amino acid sequence sharing identity equal to or higher than 95% with the amino acid sequence represented by SEQ ID NO: 208.

The antibody J just needs to contain at least the heavy chain and light chain CDRs 1 to 3, and may further contain FR of the heavy chain variable region and the light chain variable region. Examples of sequences of FR1 to FR4 of the heavy chain variable region, sequences of FR1 to FR4 of the light chain variable region, a complete sequence of the heavy chain variable region, and a complete sequence of the light chain variable region include sequences of the antibody R11 described in Tables 3 and 5 or amino acid sequences sharing identity equal to or higher than 95% with the above sequences. More specifically, examples of the antibody J include the antibody R11.

R11

The rat anti-CLDN-5 antibody R11 has an amino acid sequence represented by SEQ ID NO: 19 as the complete sequence of the heavy chain variable region (sequence in which FR1, CDR1, FR2, CDR2, FR3, CDR3, and FR4 are arranged in this order from the N-terminal side), and has an amino acid sequence represented by SEQ ID NO: 20 as the complete sequence of the light chain variable region (sequence in which FR1, CDR1, FR2, CDR2, FR3, CDR3, and FR4 are arranged in this order from the N-terminal side).

Antibody K

The antibody K contains a heavy chain variable region containing a heavy chain CDR1 having an amino acid sequence represented by SEQ ID NO: 120 or an amino acid sequence sharing identity equal to or higher than 95% with the amino acid sequence represented by SEQ ID NO: 120, a heavy chain CDR2 having an amino acid sequence represented by SEQ ID NO: 122 or an amino acid sequence sharing identity equal to or higher than 95% with the amino acid sequence represented by SEQ ID NO: 122, and a heavy chain CDR3 having an amino acid sequence represented by SEQ ID NO: 124 or an amino acid sequence sharing identity equal to or higher than 95% with the amino acid sequence represented by SEQ ID NO: 124 and/or a light chain variable region containing a light chain CDR1 having an amino acid sequence represented by SEQ ID NO: 211 or an amino acid sequence sharing identity equal to or higher than 95% with the amino acid sequence represented by SEQ ID NO: 211, a light chain CDR2 having an amino acid sequence represented by SEQ ID NO: 213 or an amino acid sequence sharing identity equal to or higher than 95% with the amino acid sequence represented by SEQ ID NO: 213, and a light chain CDR3 having an amino acid sequence represented by SEQ ID NO: 215 or an amino acid sequence sharing identity equal to or higher than 95% with the amino acid sequence represented by SEQ ID NO: 215.

The antibody K just needs to contain at least the heavy chain and light chain CDRs 1 to 3, and may further contain FR of the heavy chain variable region and the light chain variable region. Examples of sequences of FR1 to FR4 of the heavy chain variable region, sequences of FR1 to FR4 of the light chain variable region, a complete sequence of the heavy chain variable region, and a complete sequence of the light chain variable region include sequences of the antibody R14 described in Tables 3 and 5 or amino acid sequences sharing identity equal to or higher than 95% with the above sequences. More specifically, examples of the antibody K include the antibody R14.

R14

The rat anti-CLDN-5 antibody R14 has an amino acid sequence represented by SEQ ID NO: 21 as the complete sequence of the heavy chain variable region (sequence in which FR1, CDR1, FR2, CDR2, FR3, CDR3, and FR4 are arranged in this order from the N-terminal side), and has an amino acid sequence represented by SEQ ID NO: 22 as the complete sequence of the light chain variable region (sequence in which FR1, CDR1, FR2, CDR2, FR3, CDR3, and FR4 are arranged in this order from the N-terminal side). Presumably, this antibody may recognize the primary structure and the three-dimensional structure of the second extracellular loop. Furthermore, presumably, this antibody may recognize the three-dimensional structure created by the transmembrane domain of hCLDN-5.

Antibody L

The antibody L contains a heavy chain variable region containing a heavy chain CDR1 having an amino acid sequence represented by SEQ ID NO: 127 or an amino acid sequence sharing identity equal to or higher than 95% with the amino acid sequence represented by SEQ ID NO: 127, a heavy chain CDR2 having an amino acid sequence represented by SEQ ID NO: 129 or an amino acid sequence sharing identity equal to or higher than 95% with the amino acid sequence represented by SEQ ID NO: 129, and a heavy chain CDR3 having an amino acid sequence represented by SEQ ID NO: 131 or an amino acid sequence sharing identity equal to or higher than 95% with the amino acid sequence represented by SEQ ID NO: 131 and/or a light chain variable region containing a light chain CDR1 having an amino acid sequence represented by SEQ ID NO: 218 or an amino acid sequence sharing identity equal to or higher than 95% with the amino acid sequence represented by SEQ ID NO: 218, a light chain CDR2 having an amino acid sequence represented by SEQ ID NO: 220 or an amino acid sequence sharing identity equal to or higher than 95% with the amino acid sequence represented by SEQ ID NO: 220, and a light chain CDR3 having an amino acid sequence represented by SEQ ID NO: 222 or an amino acid sequence sharing identity equal to or higher than 95% with the amino acid sequence represented by SEQ ID NO: 222.

The antibody L just needs to contain at least the heavy chain and light chain CDRs 1 to 3, and may further contain FR of the heavy chain variable region and the light chain variable region. Examples of sequences of FR1 to FR4 of the heavy chain variable region, sequences of FR1 to FR4 of the light chain variable region, a complete sequence of the heavy chain variable region, and a complete sequence of the light chain variable region include sequences of the antibody R20 described in Tables 3 and 5 or amino acid sequences sharing identity equal to or higher than 95% with the above sequences. More specifically, examples of the antibody L include the antibody R20.

R20

The rat anti-CLDN-5 antibody R20 has an amino acid sequence represented by SEQ ID NO: 23 as the complete sequence of the heavy chain variable region (sequence in which FR1, CDR1, FR2, CDR2, FR3, CDR3, and FR4 are arranged in this order from the N-terminal side), and has an amino acid sequence represented by SEQ ID NO: 24 as the complete sequence of the light chain variable region (sequence in which FR1, CDR1, FR2, CDR2, FR3, CDR3, and FR4 are arranged in this order from the N-terminal side).

Antibody M

The antibody M contains a heavy chain variable region containing a heavy chain CDR1 having an amino acid sequence represented by SEQ ID NO: 134 or an amino acid sequence sharing identity equal to or higher than 95% with the amino acid sequence represented by SEQ ID NO: 134, a heavy chain CDR2 having an amino acid sequence represented by SEQ ID NO: 136 or an amino acid sequence sharing identity equal to or higher than 95% with the amino acid sequence represented by SEQ ID NO: 136, and a heavy chain CDR3 having an amino acid sequence represented by SEQ ID NO: 138 or an amino acid sequence sharing identity equal to or higher than 95% with the amino acid sequence represented by SEQ ID NO: 138 and/or a light chain variable region containing a light chain CDR1 having an amino acid sequence represented by SEQ ID NO: 225 or an amino acid sequence sharing identity equal to or higher than 95% with the amino acid sequence represented by SEQ ID NO: 225, a light chain CDR2 having an amino acid sequence represented by SEQ ID NO: 227 or an amino acid sequence sharing identity equal to or higher than 95% with the amino acid sequence represented by SEQ ID NO: 227, and a light chain CDR3 having an amino acid sequence represented by SEQ ID NO: 229 or an amino acid sequence sharing identity equal to or higher than 95% with the amino acid sequence represented by SEQ ID NO: 229.

The antibody M just needs to contain at least the heavy chain and light chain CDRs 1 to 3, and may further contain FR of the heavy chain variable region and the light chain variable region. Examples of sequences of FR1 to FR4 of the heavy chain variable region, sequences of FR1 to FR4 of the light chain variable region, a complete sequence of the heavy chain variable region, and a complete sequence of the light chain variable region include sequences of the antibody R28 described in Tables 3 and 5 or amino acid sequences sharing identity equal to or higher than 95% with the above sequences. More specifically, examples of the antibody M include the antibody R28.

R28

The rat anti-CLDN-5 antibody R28 has an amino acid sequence represented by SEQ ID NO: 25 as the complete sequence of the heavy chain variable region (sequence in which FR1. CDR1, FR2, CDR2, FR3, CDR3, and FR4 are arranged in this order from the N-terminal side), and has an amino acid sequence represented by SEQ ID NO: 26 as the complete sequence of the light chain variable region (sequence in which FR1, CDR1, FR2, CDR2, FR3, CDR3, and FR4 are arranged in this order from the N-terminal side).

In the above preferred examples (SEQ ID NOS: 1 to 26) of the complete sequences of the heavy chain variable region and the light chain variable region of the antibodies M3, M11. M23, M29, M48, R2, R3, R8, R9, R11, R14, R20, and R28, the amino acid sequences may have mutations. For example, sequences sharing identity which is preferably equal to or higher than 90%, more preferably equal to or higher than 95%, even more preferably equal to or higher than 98%, and still more preferably equal to or higher than 99% with the preferred examples (SEQ ID NOS: 1 to 26) can also be adopted as complete sequences of the heavy chain variable region and the light chain variable region of the antibodies M3, M11, M23, M29, M48, R2, R3, R8, R9, R11, R14, R20, and R28. Although the mutation may occur in any portion, in a case where the attenuation of antibody affinity is not a goal, it is preferable that the mutation occurs in a portion other than CDR.

The antibody according to the embodiment of the present invention may be a monoclonal antibody or a polyclonal antibody. However, from the viewpoint of the value of Kd, specificity, and the like, it is preferable that the antibody is a monoclonal antibody.

The molecular weight of the antibody according to the embodiment of the present invention is not particularly limited. The lower limit of the molecular weight is 20,000 for example, preferably 50,000, more preferably 100,000, and even more preferably 120,000. The upper limit thereof is 1,000,000 for example, preferably 500,000, and more preferably 200,000.

The structure of the antibody according to the embodiment of the present invention is not particularly limited. The antibody according to the embodiment of the present invention may or may not contain a constant region. In a case where the antibody contains a constant region, the antibody may contain all of the heavy chain constant regions (CH1, CH2, and CH3) and a light chain constant region (CL). Alternatively, the antibody may contain any one kind of constant region among the above or contain two or more kinds of constant regions in combination among the above.

Specifically, examples of the structure of the antibody according to the embodiment of the present invention include immunoglobulin, Fab, F(ab')$_2$, a minibody, scFv-Fc, Fv, scFv, a diabody, a triabody, or a tetrabody, and the like. Among these, from the viewpoint of effects of the present invention, immunoglobulin is preferable.

Immunoglobulin has a structure that is a combination of two structures each of which includes one heavy chain having a heavy chain variable region and a heavy chain constant region and one light chain having a light chain variable region and a light chain constant region.

Fab contains a heavy chain fragment containing CH1 in a heavy chain variable region and a heavy chain constant region and a light chain containing a light chain variable region and a light chain constant region (CL), and has a structure established in a case where the heavy chain variable region and the light chain variable region are combined by the non-covalent intermolecular interaction described above or bonded to each other through a disulfide bond. In Fab, thiol groups in cysteine residues present in CH1 and CL may form a disulfide bond.

F(ab')$_2$ contains two pairs of Fab described above, and has a structure established by the formation of a disulfide bond between thiol groups in cysteine residues contained in CH1s.

The minibody has a structure established by the combination of two fragments, each of which includes a heavy chain variable region constituting scFV described below and CH3 bonded thereto, through the non-covalent intermolecular interaction between CH3s.

scFv-Fc has a structure established by the combination of two antibody fragments containing scFv described below, CH2, and CH3 through the non-covalent intermolecular interaction between CH3s similarly to the minibody, in which a disulfide bond is formed between thiol groups in cysteine residues contained in CH3.

Fv is also referred to as the smallest structural unit of an antibody, and has a structure established by the combination of a heavy chain variable region and a light chain variable region through the non-covalent intermolecular interaction. In Fv, a disulfide bond may be formed between thiol groups in cysteine residues present in the heavy chain variable region and the light chain variable region.

scFv has a structure in which the C-terminal of a heavy chain variable region and the N-terminal of a light chain variable region are linked to each other through a linker or a structure in which the N-terminal of a heavy chain variable region and the C-terminal of a light chain variable region are linked to each other through a linker. scFv is also called single-chain antibody.

The diabody, the triabody, and the tetrabody form a dimer, a trimer, and a tetramer respectively by the scFv described above, and have a structure in which variable regions are combined by the non-covalent intermolecular interaction similarly to Fv or the like in a structurally stable state.

In a case where the antibody according to the embodiment of the present invention is immunoglobulin, the class thereof is not particularly limited. Examples of the class include IgA, IgD, IgE, IgG, IgM, and subclasses of these. For example, IgG and IgM classes and the like are preferable. For example, IgG is preferable, IgG2 is more preferable, and IgG2a is even more preferable.

The source of the antibody according to the embodiment of the present invention is not particularly limited. The antibody according to the embodiment of the present invention can be, for example, a human-derived antibody, a mouse-derived antibody, a rat-derived antibody, a rabbit-derived antibody, a monkey-derived antibody, a chimpanzee-derived antibody, or the like. Furthermore, the antibody according to the embodiment of the present invention may be a chimeric antibody (for example, an antibody obtained by substituting the amino acid sequence of a constant region of an antibody derived from a non-human living organism (mouse or the like) with the amino acid sequence of a constant region of a human-derived antibody), a humanized antibody, a fully humanized antibody, or the like.

For example, the antibody according to the embodiment of the present invention can be manufactured according to a conventional method or a method based on the conventional method as long as a human CLDN-5 protein-expressing plasmid represented by SEQ ID NO: 27 is used as an immunogen (manufacturing method 1). Specifically, in a case where the antibody according to the embodiment of the present invention is a polyclonal antibody, by immunizing a non-human animal such as a domestic rabbit with the plasmid, the antibody can be obtained from the serum of the immunized animal according to a common method. In contrast, in a case where the antibody according to the embodiment of the present invention is a monoclonal antibody, by immunizing a non-human animal such as a mouse with the plasmid and performing cell fusion between lymphocytes collected from the obtained lymph nodes or spleen and myeloma cells, the antibody can be obtained from the prepared hybridoma cells (Current protocols in Molecular Biology edit. Ausubel et al. (1987) Publish. John Wiley and Sons. Section 11.4~11.11).

The target animal to be immunized with the plasmid is not particularly limited as long as it is an animal capable of producing antibodies. As the target animal, for example, animals with autoimmune diseases (in the case of mouse, for example; a BXSB mouse and the like) are preferable.

In a case where at least the amino acid sequence of CDR of the antibody according to the embodiment of the present invention is already known, the antibody according to the embodiment of the present invention can be manufactured by a method (manufacturing method 2) including a step of culturing a host transformed by a polynucleotide encoding the antibody according to the embodiment of the present invention and collecting fractions containing the antibody according to the embodiment of the present invention.

The polynucleotide encoding the antibody according to the embodiment of the present invention is not particularly limited as long as the polynucleotide contains the antibody according to the embodiment of the present invention in an expressible state. The polynucleotide may contain other sequences in addition to the sequence encoding the antibody according to the embodiment of the present invention. Examples of those other sequences include a secretory signal peptide-encoding sequence disposed close to the sequence encoding the antibody according to the embodiment of the present invention, a promoter sequence, an enhancer sequence, a repressor sequence, an insulator sequence, a replication origin, a drug-resistant gene-encoding sequence, and the like. Furthermore, the polynucleotide encoding the antibody according to the embodiment of the present invention may be a linear polynucleotide or a cyclic polynucleotide (vector or the like).

Specific examples of the polynucleotide according to an embodiment of the present invention include (I) polynucleotide having a base sequence encoding at least one kind of domain selected from the group consisting of the heavy chain, the heavy chain variable region, and the heavy chains CDRs 1-3 of the antibody according to the embodiment of the present invention, (II) polynucleotide having a base sequence encoding at least one kind of domain selected from the group consisting of the light chain, the light chain variable region, and the light chains CDRs 1-3 of the antibody according to the embodiment of the present invention, (III) polynucleotide containing a nucleic acid which has a base sequence encoding at least one kind of domain selected from the group consisting of the heavy chain, the heavy chain variable region, and the heavy chains CDRs 1-3 of the antibody according to the embodiment of the present invention and has a base sequence encoding at least one kind of domain selected from the group consisting of the light chain, the light chain variable region, and the light chains CDRs 1-3 of the antibody according to the embodiment of the present invention, and the like.

The host is not particularly limited, and examples thereof include an insect cell, a eukaryotic cell, a mammal cell, and the like. Among these, from the viewpoint of more efficiently expressing the antibody, an HEK cell, a CHO cell, an NS0 cell, an SP2/0 cell, a P3U1 cell, or the like as the mammal cell is preferable.

The methods of transformation, culture, and collection are not particularly limited, and the methods known in the antibody manufacturing can be adopted.

After being collected, the antibody according to the embodiment of the present invention may be purified if necessary. The purification can be performed by the methods known in the antibody manufacturing, such as chromatography and dialysis.

3. Complex

As an embodiment, the present invention relates to a complex of the antibody according to an embodiment of the present invention and a medication (in the present specification, the complex will be described as "complex according to an embodiment of the present invention" as well in some cases). Hereinafter, the complex will be described.

The medication is not particularly limited and can be appropriately selected according to the purpose. Examples of the medication include physiologically active substances such as a nucleic acid, a polynucleotide, a gene, analogues of these, glycosaminoglycan and a derivative thereof, oligosaccharide, polysaccharide and a derivative thereof, a protein, and a peptide; pharmacologically active substances such as an antineuralgic agent, an antiviral agent, an anticancer agent, an antibiotic, an enzyme, an antioxidant, an anti-inflammatory, steroid, an angiotensin converting-enzyme inhibitor, a vasodilator, a smooth muscle cell proliferation and/or migration inhibitor, a platelet aggregation inhibitor, an anticoagulant, a chemical mediator liberation inhibitor, an immunodepressant, a lipid uptake inhibitor, a hormone, an angiotensin receptor antagonist, a vascular endothelial cell growth factor or a vascular endothelial cell growth inhibitor, an aldose reductase inhibitor, a lipoxygenase inhibitor, an immunostimulator, a Millard reaction inhibitor, an amyloidosis inhibitor, a Nitric Oxide Synthase (NOS) inhibitor, an Advanced glycation endproducts (ACEs) inhibitor, neurological disease-related antibodies such as an anti-Aβ antibody and an anti-Tau antibody, and a radical scavenger, and the like. The complex according to the embodiment of the present invention contains the antibody according to the embodiment of the present invention as a partial structure. Accordingly, the complex can more efficiently permeate the blood-brain barrier. Therefore, among the above medications, the antineuralgic agent (for example, a medication used for treating and/or diagnosing central nervous system diseases) is preferable.

Specific examples of the antineuralgic agent include antidepressants such as anxiolytics including Constan, Sepazon, Cercine, Serenal, Solanax, Depas, Balance, Meilax, Rize, Rivotril, Lexotan, Wypax, Sadiel, Grandaxin, and Erispan; antidepressants including Anafranil, Tofranil, Tryptanol, Amoxan, Amplit, Prothiaden, Tecipul, Tetramide, Ludiomil, Desyrel, Reslin, Abilit, Dogmatyl, Miradol, Ritalin, Depromel, Paxil, Luvox, and Toledomin; anti-insomnia drugs including Amoban, Halcion, Evamyl, Myslee, Rhythmy, Lendormin, Loramet, Silece, Doral, Benzalin, Eurodin, Rohypnol, Insumin, Somelin, Dalmate, Phenobal, and Isomytal; tranquilizers including Wintermin, Contomin, Neuleptil, Hirnamin, PZC, Melleril, Impromen, Serenace, Orap, Cremin, Clofekton, Defekton, Forit, Lodopin, and Atarax; drugs for bipolar disorder including Limas and Tegretol; anticonvulsants including Ethotoin, Phenytoin, acetylpheneturide, Primidone, Sultiame, Ethosuximide, Clonazepam, Carbamazepine, sodium valproate, and Zonisamide; agents for treating parkinson's disease including Levodopa, pergolide mesilate, amantadine hydrochloride, trihexyphenidyl hydrochloride, piroheptine hydrochloride, mazaticol hydrochloride, methixene hydrochloride, Biperiden, Profenamine, and Droxidopa, and the like.

The complex according to the embodiment of the present invention is formed in a manner in which the antibody of according to the embodiment of the present invention and a medication are directly bonded to each other or indirectly bonded to each other through a linker or the like. The mode of bonding is not particularly limited, and examples thereof include a covalent bond, a coordinate bond, an ionic bond, and the like. Furthermore, the surface of microparticles such as liposomes may be modified with the antibody according to the embodiment of the present invention such that the medication is incorporated into the microparticles. The antibody according to the embodiment of the present invention and the medication can be bonded to each other by known methods or methods based on the known methods according to the mode of bonding.

A covalent bond can be formed, for example, by reacting functional groups contained in each of the antibody according to the embodiment of the present invention and the medication or reacting introduced functional groups if necessary. Examples of combinations of the functional groups include an amino group and a carboxyl group, a carboxyl group and a hydroxy group, a maleimide group and a thiol group, a thiol group and a thiol group, a hydrazide group and a ketone group, a hydrazide group and an aldehyde group, an amino group and an aldehyde group, a thiol group and a carboxyl group, an amino group and a squaric acid derivative, a dienyl aldehyde group and an amino group, a haloester and a thiol group, an azide and an alkyne, and the like.

4. Drug

As an embodiment, the present invention relates to a drug containing at least one kind of component selected from the group consisting of the antibody according to an embodiment of the present invention and the complex according to an embodiment of the present invention (in the present specification, the drug will be described as "drug according to an embodiment of the present invention" as well in some cases).

The antibody according to the embodiment of the present invention can accelerate the permeation of materials into the blood-brain barrier by opening a junction between cerebrovascular endothelial cells. Therefore, the antibody according to the embodiment of the present invention and the complex according to the embodiment of the present invention can be suitably used as active components of drugs, particularly, drugs used for controlling (inhibiting) the blood-brain barrier, controlling (inhibiting) the barrier function of a cerebrovascular endothelial cell layer, accelerating the permeation of medications into the blood-brain barrier, controlling the local variation of CLDN-5 proteins (that is, changing localization of CLDN-5 generally present in an intercellular space so as to weaken the adhesion of the intercellular space), and the like.

In a case where the drug according to the embodiment of the present invention contains the antibody according to an embodiment of the present invention but does not contain the complex according to an embodiment of the present invention, by using the drug in combination with a medication, the permeation of the medication into the blood-brain barrier can be accelerated. Furthermore, in a case where the drug according to an embodiment of the present invention contains the complex according to the embodiment of the present invention, by using the drug as it is or using the drug in combination with a medication, the permeation of the medication in the complex or the permeation of the medication used in combination into the blood-brain barrier can be accelerated.

The content of active components in the drug according to the embodiment of the present invention can be appropriately set in consideration of the type of disease to be treated, the intended therapeutic effect, the administration method, the treatment period, the patient's age, the patient's body weight, and the like. For example, the content of active components in the drug according to the embodiment of the present invention can be about 0.0001 parts by weight to 100 parts by weight to the total amount, which is 100 parts by weight, of the drug according to the embodiment of the present invention.

As long as the desired effects are obtained, the drug according to the embodiment of the present invention can be administered in any form without particular limitation. The drug can be administered to mammals including a human being through any administration route between oral administration and parenteral administration (for example, intravenous injection, intramuscular injection, subcutaneous injection, rectal administration, transdermal administration, and local administration). The drug is preferably given by parenteral administration, and more preferably given by intravenous injection. The formulation for oral administration and parenteral administration and a manufacturing method thereof are known to those skilled in the art. By mixing the active components with a pharmaceutically accepted carrier or the like, the drug can be manufactured according to common methods.

Examples of the formulation for parenteral administration include a preparation for injection (for example, a preparation for instillation, a preparation for intravenous injection, a preparation for intramuscular injection, a preparation for subcutaneous injection, and a preparation for intracutaneous injection), an external preparation (for example, an ointment, a cataplasm, a lotion), a suppository, an inhalant, eye drops, an eye ointment, nasal drops, ear drops, a liposome preparation, and the like. For example, the preparation for injection is prepared by dissolving antibodies or cells in distilled water for injection. If necessary, a solubilizer, a buffer, a pH adjuster, an isotonizing agent, an analgesic, a preservative, a stabilizer, and the like can be added thereto. The drug can also be made into a freeze-dried formulation to be prepared at the time of use.

The drug according to the embodiment of the present invention can additionally contain other components capable of improving the blood-brain barrier control (inhibition) activity, the activity of controlling (inhibiting) the barrier function of the cerebrovascular endothelial cell layer, the activity of accelerating the permeation of a medication into the blood-brain barrier, and the like. Examples of such components include an occludin antibody and the like.

The drug according to the embodiment of the present invention can additionally contain other pharmaceutical agents effective for treating or preventing diseases. If necessary, the drug according to the embodiment of the present invention can also be mixed with components such as a germicide, an anti-inflammatory, a cell activator, vitamins, and amino acids.

In the carrier used for making the drug according to the embodiment of the present invention into a preparation, it is possible to use an excipient, a binder, a disintegrant, a lubricant, a colorant, or a flavoring agent generally used in the field of related art or to use a stabilizer, an emulsifier, an absorption promoter, a surfactant, a pH adjuster, an antiseptic, an antioxidant, an extender, a moistening agent, a surface activator, a dispersant, a buffer, a preservative, a solubilizer, an analgesic, and the like if necessary.

The dose of the drug according to the embodiment of the present invention can be determined by a clinician based on various factors such as the administration route, the type of disease, the extent of symptoms, the age, sex, and body weight of the patient, the severity of disease, the pharmacological knowledge such as pharmacokinetics and toxicological characteristics, whether or not a medication delivery system is used, whether the drug is used as a portion of a combination with another medication, and the like. For example, a daily dose of the drug according to the embodiment of the present invention can be about 1 μg/kg (body weight) to 10 g/kg (body weight). The administration of the drug according to the embodiment of the present invention can be scheduled in consideration of the same factors as those considered to determine the dose. For example, the drug can be administered once a day to once a month at the daily dose described above.

5. Reagent

As an embodiment, the present invention relates to a reagent containing at least one kind of component selected from the group consisting of the antibody according to an embodiment of the present invention and the complex according to an embodiment of the present invention (in the present specification, the reagent will be referred to as "reagent according to an embodiment of the present invention" as well in some cases). More specifically, the present invention relates to a reagent for detecting a CLDN-5-expressing cell or solubilized CLDN-5 and the like. Herein, "reagent" also includes "test drug" for performing a test, detection, diagnosis, and the like by detecting CLDN-5 and the like.

The reagent according to an embodiment of the present invention may be in the form of a composition containing at least one kind of component selected from the group consisting of the antibody according to an embodiment of the present invention and the complex according to an embodiment of the present invention. If necessary, the composition may contain other components. Examples of those other components include a base, a carrier, a solvent, a dispersant, an emulsifier, a buffer, a stabilizer, an excipient, a binder, a disintegrant, a lubricant, a thickener, a moisturizer, a colorant, a flavoring, a chelating agent, and the like.

The reagent according to the embodiment of the present invention may be in the form of a kit containing at least one kind of component selected from the group consisting of the antibody according to an embodiment of the present invention and the complex according to an embodiment of the present invention. The kit may contain a container, a reagent, and the like used for performing detection, separation, and the like of a CLDN-5-expressing cell and solubilized CLDN-5. Examples of the container and the reagent include a test tube, a microtiter plate, agarose particles, latex particles, a column for purification, a labeling antibody, standard reagents (positive control and negative control), a reagent for extracting exosome (WO2016/088689A), and the like.

EXAMPLES

Hereinafter, the present invention will be specifically described based on examples, but the present invention is not limited to the examples.

Example 1) Preparation of Antibody

Example 1-1) Cell Fusion

A DNA fragment consisting of a sequence encoding a wild-type human CLDN-5 protein (SEQ ID NO: 27) was inserted into a protein expression vector pcDNA3.1 (Thermo Fisher Scientific. V79020) or the like for mammal cells, thereby preparing a plasmid for immunization. By using the prepared plasmid for immunization, subcutaneous immunization was performed. BXSB mice and Wistar rats found to exhibit an increase in serum antibodies by immunization were finally immunized. After the final immunization, lymph node cells were collected from the animals according to a common method and fused with mouse myeloma, cells (P3U1). The cells obtained after fusion were seeded in ten 96-well plates and cultured for 10 days in a culture medium 1* in 10% $CO_2$ at 37° C.

*Culture medium 1: Hybridoma SFM (Thermo Fisher Scientific, 12045084)+1× BM condimed H1 Hybridoma cloning supplement (Roche, 1088947), 1×HAT supplement (Thermo Fisher Scientific, 21060017), 1× Penicillin-Streptomycin solution (Wako, 168-23191).

Example 1-2) Preparation of Cell for Screening

A DNA fragment consisting of a wild-type human CLDN-5 protein (SEQ ID NO: 27)-encoding sequence was inserted into a pCX4pur vector (manufactured by Osaka Bioscience Institute), thereby obtaining a vector for preparing a retrovirus. Packaging cells (Phoenix A cells) were seeded in each of the wells of a 12-well plate at $0.5 \times 10^5$ cells and cultured for 24 hours. Then, by using 3 µL of X-treme GENE HP DNA (Roche Diagnosis, 06366244001), 0.5 µg of a pCL ampho vector and 0.5 µg of the vector for preparing a retrovirus were transinfected to the phoenix A cells. After 24 hours, the medium was replaced, and the cells were further cultured for 24 hours. The culture supernatant containing retroviruses was collected and filtered through a filter having a pore size of 0.45 µm so as to remove foreign substances, and polybrene (Sigma-Aldrich, H9268-5G) was added thereto such that a concentration thereof became 3 µg/mL. By using the obtained solution, human fibrosarcoma-derived cells (HT-1080 cells) were cultured for 24 hours. Thereafter, by using 10% FBS-supplemented DMEM in a 10 cm dish containing 5 µg/mL puromycin (InvivoGen, ant-pr-1), the obtained cells were cultured for 2 days in 5% $CO_2$ at 37° C. Subsequently, uninfected cells were removed. The cell caused to express only a puromycin-resistant gene was named HT-1080/mock, and the cell caused to express the puromycin-resistant gene and hCLDN-5 was named HT-1080/hCLDN-5.

Example 1-3) Construction of Hybridoma Producing Specific Monoclonal Antibodies

After the culture, the culture supernatant was collected from all the 96-well plates and subjected to cell-ELISA using HT-1080/hCLDN-5. During the Cell-ELISA, the HT-1080/hCLDN-5 caused to adhere to the surface of the 96-well plate was stained with the collected culture supernatant and HRP-labeled anti-rat IgG antibodies and allowed to react with a fluorogenic substrate Amplex Red reagent (Thermo Fisher Scientific, A12222), and the fluorescence intensity thereof was measured using a plate reader.

Furthermore, on the culture supernatant from the wells determined as being positive, flowcytometry (FCM) was performed as below. Specifically, HT-1080/mock and HT-1080/hCLDN-5 were stained with the culture supernatant and PE-labeled anti-rat IgG antibodies and subjected to FCM.

From the well determined as being positive by FCM, hybridoma cells were collected and treated to be monoclonal cells. Specifically, the hybridoma cells in each of the FCM-positive wells were seeded in one 96-well plate at 1.2 cells/well and cultured in the culture medium 1 for 10 to 12 days in 10% $CO_2$ at 37° C. After culture, the culture supernatant was collected from the entire 96-well plate and subjected to cell-ELISA described above using HT-1080/hCLDN-5.

From the wells confirmed to be positive by cell-ELISA, wells in which the formation of a single colony was observed under a microscope were selected, and the expansion culture of the colony was sequentially performed in a 24-well plate and a 6-well plate. After the culture, the culture supernatant was collected from the 6-well plate and subjected to FCM using HT 1080/mock and HT-1080/hCLDN-5 described above.

One clone found to have strong shift intensity by FCM was selected from each of the wells having not yet been treated to make monoclonal cells, expanded to a 15 cm dish, and cultured in 10% $CO_2$ at 37° C. After the culture, a cell stock was prepared using a cell banker 1 (ZENOAQ, CB011) containing the collected cells. Furthermore, by using the culture supernatant at the time of preparing the stock, an Iso Strip Mouse Monoclonal Antibody Isotyping Kit (Roche, 11493027001), and a Rat Monoclonal Antibody Isotyping Test Kit (Bio-Rad, RMT1), the class and subclass of the antibodies were determined.

The determined class and subclass of each of the antibodies are described in the following Table 1.

TABLE 1

|  | Species | Heavy chain/light chain |
|---|---|---|
| M3 | Mouse | IgG2b/$_K$ |
| M11 | Mouse | IgG2b/$_K$ |
| M23 | Mouse | IgG2b/$_K$ |
| M29 | Mouse | IgG3/$_K$ |
| M48 | Mouse | IgG3/$_K$ |
| R2 | Rat | IgG2a/$_K$ |
| R3 | Rat | IgG2a/$_K$ |
| R8 | Rat | IgG2b/$_K$ |
| R9 | Rat | IgG2b/$_K$ |
| R11 | Rat | IgG2b/$_K$ |
| R14 | Rat | IgG2a/$_K$ |
| R20 | Rat | IgG2a/$_K$ |
| R28 | Rat | IgG2a/$_K$ |

Example 1-4) Purification of Antibody

Pristane (Funakoshi Co., Ltd., 980-60542) (0.5 mL) was administered to the abdominal cavity of a Balb/c nu/nu mouse, and after 1 week, the constructed hybridoma cells ($1 \times 10^7$ cells) were administered into the abdominal cavity. Seven to ten days after the administration, ascites was rapidly built up in the mouse administered with the hybridoma. Therefore, a point in time when the abdominal swelling will be maximized was estimated, and the ascites was collected under anesthesia. The ascites was collected into a 15 mL tube and subjected to centrifugation (3,000 rpm, 10 min) so as to remove unwanted substances. The ascites was preserved at −80° C.

A Starting buffer* in an amount triple the amount of the ascites was added to the ascites, left to stand for 20 minutes, and then subjected to centrifugation (3,000 rpm, 30 minutes) and filtered through a membrane filter having a pore size of 0.8 µm so as to remove insoluble matters. The obtained sample was loaded on a protein G (GE healthcare, 17061801) column (column length 0.7×5 cm) thoroughly equilibrated by the Starting buffer. After the sample solution was completely discharged, the column was washed with 30 mL of the Starting buffer. Then, 10 mL of an Elution buffer* was passed through the column such that the antibodies were eluted. By using a fraction collector, fractions each including 50 drops of the effluent were collected. At this time, 50 µL of a Neutralize buffer* was added in advance to each fraction of the fraction collector. The obtained antibody fractions were subjected to dialysis in PBS (Slide A Lyzer 20 kMWCO, Thermo Fisher Scientific, 66003) under the condition of 4° C. Hereinafter, the names of the purified monoclonal antibodies will be the same as the names of the hybridomas described above (for example, an antibody obtained from a hybridoma M3 is described as "antibody M3" or simply described as "M3").

*Starting buffer: 20 mM sodium phosphate buffer, pH 7.0
*Elution buffer: 100 mM glycine HCl, pH 2.7 *Neutralize buffer: 1.0 M tris HCl, pH 9.0.

Example 2) Determination of Amino Acid Sequence of Antibody

Based on the genomic information on the hybridomas cloned in Example 1), the amino acid sequences of the antibodies were determined. For the antibodies, the amino acid sequence of each of the domains (CDRs 1-3 and FRs 1-4) in the heavy chain variable region are shown in Table 2 and Table 3, and the amino acid sequence of each of the domains (CDRs 1-3 and FRs 1-4) in the light chain variable region are shown in Table 4 and Table 5. In Tables 2 to 5, the amino acids were represented by sing letter codes, the top left side of each sequence is the N-terminal side, the number in the parenthesis represents SEQ ID NO of the sequence, and "Complete" represents a complete sequence (sequence in which FR1, CDR1, FR2, CDR2, FR3, CDR3, and FR4 are arranged in this order from the N-terminal side) of a heavy chain variable region or a light chain variable region.

TABLE 2

Heavy chain variable region

| mAb | FR1 | CDR1 | FR2 | CDR2 | FR3 | CDR3 | FR4 | Complete |
|---|---|---|---|---|---|---|---|---|
| M3 | EVQLQQS GPELVKP GASVKIS CKAS (49) | GYSFTGY (50) | YMNWVK QSPEKSL EWIGDI (51) | NPSTGG (52) | ATYNQKF KAKATLT VDKSSST AYMQLKS LTSEDSA VFYCAL (63) | YSNYGFV Y (54) | WGQGTL VTVSA (55) | (1) |
| M11 | QVQLKQS GPGLVQP SQSLSIT CTVS (56) | GFSLIRY (57) | GVHWVR QSPGKGL EWLGVK (58) | WSGGS (59) | TDYNGAF KSRLSISK DNSKSQV FFKMNSL QADDTAI YYCAR (60) | GLDGYYV PDV (61) | WGTGTS VTVS (62) | (3) |
| M23 | EVQLQQS GPVLVKP GPSVMIS CKAS (63) | GFTFTDY (64) | YMHWVK QSHGKSL EWIGLV (65) | YPYNGG (66) | TDYNQKF KGKATLT VDTSSST AYMELNS LTSEDSA VYYCAR (67) | CLYDGLY FYAMDY (68) | WGQGTS VTVSS (69) | (5) |
| M29 | EVQLVES GGGLVQ PKGSLKL SCAAS (70) | GFTFNIY (71) | AMHWVR QAPGKGL EWVARI (72) | RSKSSNY A (73) | TYYVDSV KDRFIISR DDSQSM LYLQVNN LKTEDTA MYYCVR (74) | EGNWDC FDY (75) | WGQGTT LTVSS (76) | (7) |
| M48 | QAYLQQS GAELVRP GASVKMS CKAS (77) | GYTFTSY (78) | NMHWVK KTRRQGL EWIGAI (79) | SPGNGN (80) | TSYNQKF KGKATLT VDKSSST AYMQLSS LTSEDSA VYFCAR (81) | DDGYYG ALDY (82) | WGQGTS VTVSS (83) | (9) |
| R2 | QVQLKES GPGLVQP SQTLSLT CTVS (84) | GLSLIRN (85) | SVSWIRQ PPGKGLE WMGVI (86) | WSNGG (87) | TEYNSTV KSRLSISR DTSKNQV FLKMNSL QTEDSA MFFCAR (88) | TPDGYYP YFDY (89) | WGQGVM VTVSS (90) | (11) |
| R3 | EVQLVES GGGLVQ PGRSLKL SCAAS (91) | GFTFDY (92) | YMAWVR QAPKKGL EWVASI (93) | SYEGRN (94) | TYYGDSV KGRFTIS RDNAKST LYLQMKS LRSEDTA TYYCTR (95) | HPRRYFD Y (96) | WGQGVM VTVSS (97) | (13) |

TABLE 3

Heavy chain variable region

| mAb | FR1 | CDR1 | FR2 | CDR2 | FR3 | CDR3 | FR4 | Complete |
|---|---|---|---|---|---|---|---|---|
| R8 | VKVVESG GGLVQP | GFTFSDY (99) | FMAVVR Q$PKKGL (101) | NYGGSR | TYYEDSV KGRFTIS | HPHRLFD Y (103) | WGQGVM VTVSS | (15) |

TABLE 3-continued

Heavy chain variable region

| mAb | FR1 | CDR1 | FR2 | CDR2 | FR3 | CDR3 | FR4 | Complete |
|---|---|---|---|---|---|---|---|---|
| | GRSMKLS CAAS(98) | | EVVVASI (100) | | RDNAKST LYLQMNS LRSEDTA TYYCAR (102) | | (104) | |
| R9 | QVTLKES GPGILQP SHTLSLT CSFS (105) | GFSLNTY GV(106) | GVNWIRQ PSGKGLE MASI (107) | WWFIGK (108) | TYINPSLK NRLTVSK DPSNNQA FLEVTNV DPADTAT YYCAH (109) | ARAQLLD Y(110) | WGQGVM VTVSS (111) | (17) |
| R11 | EVQLVES GGGLVQ PGRSRKL SCAAS (112) | GFTFNNY (113) | GMAWVR QAPTKGL EWVASI (114) | TNSGYT (115) | TYYRDSV KGRFTIS RDNAKNA LYLQMDS LRSEDTA TYYCTT (116) | GGYGGY FPLFDY (117) | WGHGVM VTVSS (118) | (19) |
| R14 | QVTLKES GPGILQP SHTLSLT CSFS (119) | GFSLSTY GM(120) | GVSWIRQ PSGKGLE WLASI (121) | WWNGR (122) | TYTNPSL MSRLTVS KDTSTNQ AFLRVTS VETADTA TYYCAH (123) | TPYDYSN LGWFTY (124) | WGQGTL VTVSS (125) | (21) |
| R20 | EVQLVES GGGLVQ PGRSMKL SCAVS (126) | GFTFSDY (127) | YMAWVR QAPKKGL EWVASI (128) | SYEGRN (129) | TYYGDSV KGRFTIS RDNAKNT LYLQMNS LRSEDTA TYYCAR (130) | HPRRYFD F(131) | WGPGTM VTVSS (132) | (23) |
| R28 | EVQLVES GGGLVQ PGRSLKL SCAAS (133) | GFTFSDY (134) | FMAWVR QAPKKGL EWVASI (135) | NYEGSR (136) | TYYGDSV KDRFTIS RDNTKTT LYLQMTS LRSEDTA TYYCAR (137) | HPRRYFD F(138) | WGQGVM VTVSS (139) | (25) |

TABLE 4

Light chain variable region

| MAb | FR1 | CDR1 | FR2 | CDR2 | FR3 | CDR3 | FR4 | Complete |
|---|---|---|---|---|---|---|---|---|
| M3 | DVVMTQT PLTLSVT LGQPASI SC(140) | KSSQSLL YSDGKTY LN(141) | WLLQRP GQSPKRL IY(142) | LVSKLDS (143) | GVPDRFT GSGSGT DFTLKISR VEAEDLG LYYC (144) | VQGIHFP RT(145) | FGGGTKL EIK(146) | (2) |
| M11 | DIVMTQS HKFMSTS VGDRVSI TC(147) | KASQDVS TNVA (148) | WYQQKP GQSPTLLI Y(149) | WASTRH T(150) | GVPDRFT GSGSGT DYTLTISS VQAFDLA LYYC (151) | QQHYST PLT(152) | FGAGTKL ELRR (153) | (4) |
| M23 | DIVMSQS PSSLAVS AGEKVTM TC(154) | KSSQSLL NSRARKN YLA(155) | WYQQKA GQSPKLL MY(156) | WASTRE S(157) | GVPDRFT ASGSGTD FTLTISSV QAEDLAV FYC(158) | KQSYNLP WT(159) | FGGGTKL EIKR (160) | (6) |

TABLE 4-continued

| | Light chain variable region | | | | | | | |
|---|---|---|---|---|---|---|---|---|
| MAb | FR1 | CDR1 | FR2 | CDR2 | FR3 | CDR3 | FR4 | Complete |
| M29 | DIVMSQSPSSLPVSVGQKVTMTC(161) | KSSQSLLYTSNQKNYLA(162) | WYQQKPGQSPKLLIY(163) | WASTRES(164) | GVPDRFTGSGSGTDFTLTISSVKAEDLAIYYC(165) | QQYYRYHT(166) | FGGGTRLEIK(167) | (8) |
| M48 | DIVLTQSPATLSVIPGESVSLSC(168) | RASQGISTSIH(169) | WYQQKSNESPRLLIR(170) | YASQSIS(171) | RIPSRFSGSGSGTDFTLTINGVESEDLSVYYC(172) | QQSYNLPLT(173) | FGSGTKLEI(174) | (10) |
| R2 | DIVLTQSPATLSVTPGESVSLSC(175) | RASQGISTSIH(176) | WYQQKSNESPRLLIR(177) | YASQSIS(178) | RIPSRFSGSGSGTDFTLTINGVESEDLSVYYC(179) | QQSYNLPLT(180) | FGSGTKLEI(181) | (12) |
| R3 | DIVMTQSPSSLAVSAGETVTMNC(182) | RSSQSLFSSGDQKKFLA(183) | WYQQKPGQSPKLLIS(184) | LASTRES(185) | GVPDRFIGSGSGTDFTLTINNMQAEDLAIYYC(186) | QQHYDIPYT(187) | FGAGTKLEL(188) | (14) |

TABLE 5

| | Light chain variable region | | | | | | | |
|---|---|---|---|---|---|---|---|---|
| | FR1 | CDR1 | FR2 | CDR2 | FR3 | CDR3 | FR4 | Complete |
| R8 | DIVMTQSPSFLAVSVGETVTINC(189) | KSSQSFLSSGNQENYLA(190) | WYQQKPGQSPKLLIH(191) | LASTRES(192) | GVPDRFIGSGSGTDFTLTISSMQAEDVAIYYC(193) | QQHYDIPYT(194) | FGAGTKLEL(195) | (16) |
| R9 | DIVMTQTPSSQAVSAGEKVTMSC(196) | KSSQSLLYSGDQKNYLA(197) | WYQQKPGQSPKLLIY(198) | LTSTRES(199) | GVPDRFIGSGSGTDFTLTISSVQAEDLADYYC(200) | QQHYSYPLT(201) | FGSGTKLEI(202) | (18) |
| R11 | DVVMTQTPVSLSVSLGGQTSISC(203) | RSSQSLFHSDGNTYLY(204) | WYLRKPGQSPQLLIY(205) | KVSNRFS(206) | GVPDRFSGSGSGTDFTLKISRVEPEDLGLYYC(207) | YQGTHYPPT(208) | FGSGTKLE(209) | (20) |
| R14 | DILMTQTPSSQAVSAGEKVTVSC(210) | KSSQSLLYSGDQKSYLA(211) | WYQQKPGQSPKLLIY(212) | LASTRKS(213) | GVPDRFIGSGSGTDFTLTISSVQAEDLADYYC(214) | QQHYTYPLT(215) | FGSGTKLEI(216) | (22) |
| R20 | DIVMTQSPSSLAVSAGETVTINC(217) | KSSQSLLFSGDQENHLA(218) | WYQQKAGQSAKLLIY(219) | WASTRES(220) | GVPDRFIGSGSGADFTLTISSMQAEDRATYYC(221) | QQNYDIPYT(222) | FGAGTKLEL(223) | (24) |

TABLE 5-continued

Light chain variable region

| | FR1 | CDR1 | FR2 | CDR2 | FR3 | CDR3 | FR4 | Complete |
|---|---|---|---|---|---|---|---|---|
| R28 | DIVMTQS PSSLAVS AGETVTI NC(224) | KSSRSLF SSGYQE NYLA (225) | WYQQKP GQSPKM LIY(226) | LASTRES (227) | GVPDRFI GSGSGT DFTLTINT LQAEDLAI YYC(228) | QQHYDIP YT(229) | FGAGTKL EL(230) | (26) |

Example 3) Analysis of Binding Specificity of Antibody

Example 3-1) Evaluation of CLDN Specificity

By the insertion of a DNA fragment consisting of an hCLDN-1 protein (SEQ ID NO: 30)-encoding sequence, an hCLDN-2 protein (SEQ ID NO: 31)-encoding sequence, an hCLDN-3 protein (SEQ ID NO 32)-encoding sequence, an hCLDN-4 protein (SEQ ID NO: 33)-encoding sequence, an hCLDN-6 protein (SEQ ID NO: 34)-encoding sequence, an hCLDN-7 protein (SEQ ID NO: 35)-encoding sequence, an mCLDN-1 protein (SEQ ID NO: 37)-encoding sequence, an mCLDN-2 protein (SEQ ID NO: 38)-encoding sequence, an mCLDN-3 protein (SEQ ID NO: 39)-encoding sequence, or an mCLDN-5 protein (SEQ ID NO: 29)-encoding sequence, vectors for preparing a retrovirus were obtained. By using these vectors and the vector for preparing a retrovirus prepared in Example 1-2), various CLDN protein-expressing cells were prepared. By using these cells and a culture supernatant of hybridomas producing antibodies as primary antibodies, FACS assay was performed by the following method.

The obtained CLDN-expressing cells were seeded in a 10 cm dish, and on the next day, the cells were collected. The primary antibodies (100 μL) were added to the obtained 1.0×10⁵ cells and allowed to react for 1 hour at 4° C. At this time, a mixed solution of a C-CPE mutant (C-CPEmt) and a mouse anti-His tag antibody (Abcam) used in Non-Patent Literature 3 was used as positive control. The cells were washed three times with 0.2% BSA-PBS, then mixed with 100 μL of a secondary antibody solution (FITC conjugated goat anti-mouse IgG or anti-rat IgG (Jackson Immune Research, 115-095-003 or 112-095-003) 400×diluted with 1% BSA-PBS, and allowed to react for 1 hour at 4° C. The cells were washed with 0.2% BSA-TBS and then analyzed using FACS caliber (BD Bioscience).

Figure 1B:
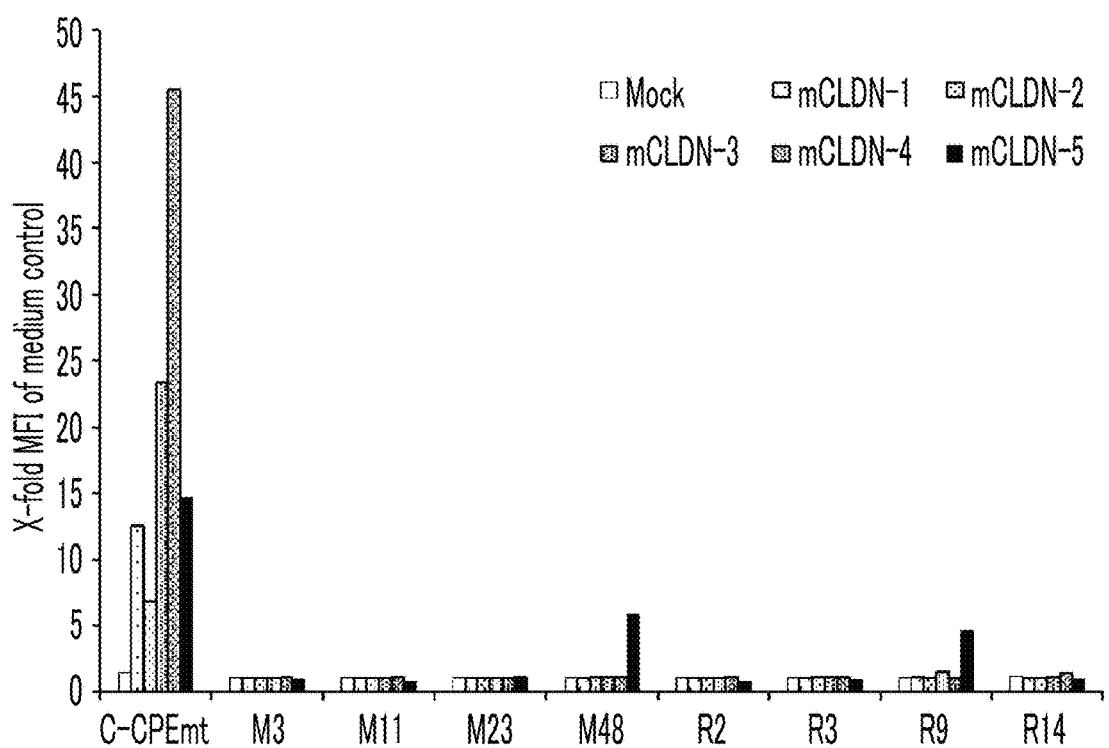

FIG. 1A illustrates the reactivity of each of the antibody clones with each human CLDN. FIG. 1B illustrates the reactivity of each of the antibody clones with each mouse CLDN. As being illustrated in FIG. 1A, the obtained anti-CLDN-5 antibody reacted only with hCLDN-5. As being illustrated in FIG. 1B, the obtained anti-CLDN-5 antibody did not exhibit strong reactivity with the mouse CLDN. M48 and R9 exhibited binding capacity to mCLDN-5 although the binding capacity was extremely low.

Example 3-2) Evaluation of Cross-Species Activity of CLDN-5

In the same manner as in Example 1-2), a DNA fragment consisting of a cCLDN-5 protein (SEQ ID NO: 28)-encoding sequence or an mCLDN-5 protein (SEQ ID NO: 29)-encoding sequence was inserted into a pCX4pur vector, thereby obtaining vectors for preparing a retrovirus. By using these vectors with the vector for preparing a retrovirus prepared in Example 1-2), various animal species CLDN-5 protein-expressing cells were prepared. By using these cells and the antibodies (antibody concentration: 5 μg/mL, as primary antibody), FACS assay was performed in the same manner as in 3-1). FIG. 2 illustrates histograms in which the abscissa shows the fluorescence signal and the ordinate shows the cell count.

As being illustrated in FIG. 2, the obtained anti-CLDN-5 antibody exhibited a high binding capacity to hCLDN-5 and cCLDN-5. Furthermore, R9 exhibited a binding capacity to mCLDN-5 although the binding capacity was extremely low.

Example 3-3) Determination of Kd Value of Antibody

By using HT-1080/hCLDN-5 and 100 μL of the anti-CLDN-5 antibody at each concentration diluted with 1.0% BSA-PBS, FACS assay was performed in the same manner as in Example 3-1). By plotting MFI obtained by the FACS assay on the Y-axis, a saturation binding curve was created, and a 50% saturation binding concentration was determined, thereby calculating a value of Kd. At this time, the equation of saturation binding-one site-specific binding of Graph Pad prism 7 (Graph Pad Software) was used. The values of Kd of the antibodies are shown in Table 6.

TABLE 6

| | Kd (nM) | |
|---|---|---|
| | Lot 1 | Lot 2 |
| M3 | 3.89 ± 0.63 | 6.41 ± 1.82 |
| M11 | 8.72 ± 1.40 | 9.68 ± 2.28 |
| M23 | 3.77 ± 0.76 | 2.78 ± 1.56 |
| M48 | 29.10 ± 7.16 | 8.47 ± 2.83 |
| R2 | 20.11 ± 5.59 | 20.68 ± 3.27 |
| R3 | 7.19 ± 3.60 | 2.44 ± 1.32 |
| R9 | 3.78 ± 2.02 | 2.75 ± 1.85 |
| R14 | 4.66 ± 0.33 | 8.42 ± 1.95 |

Example 3-4) Epitope Analysis by hCLDN-5/hCLDN-1 Chimeric CLDN

Figure 4:
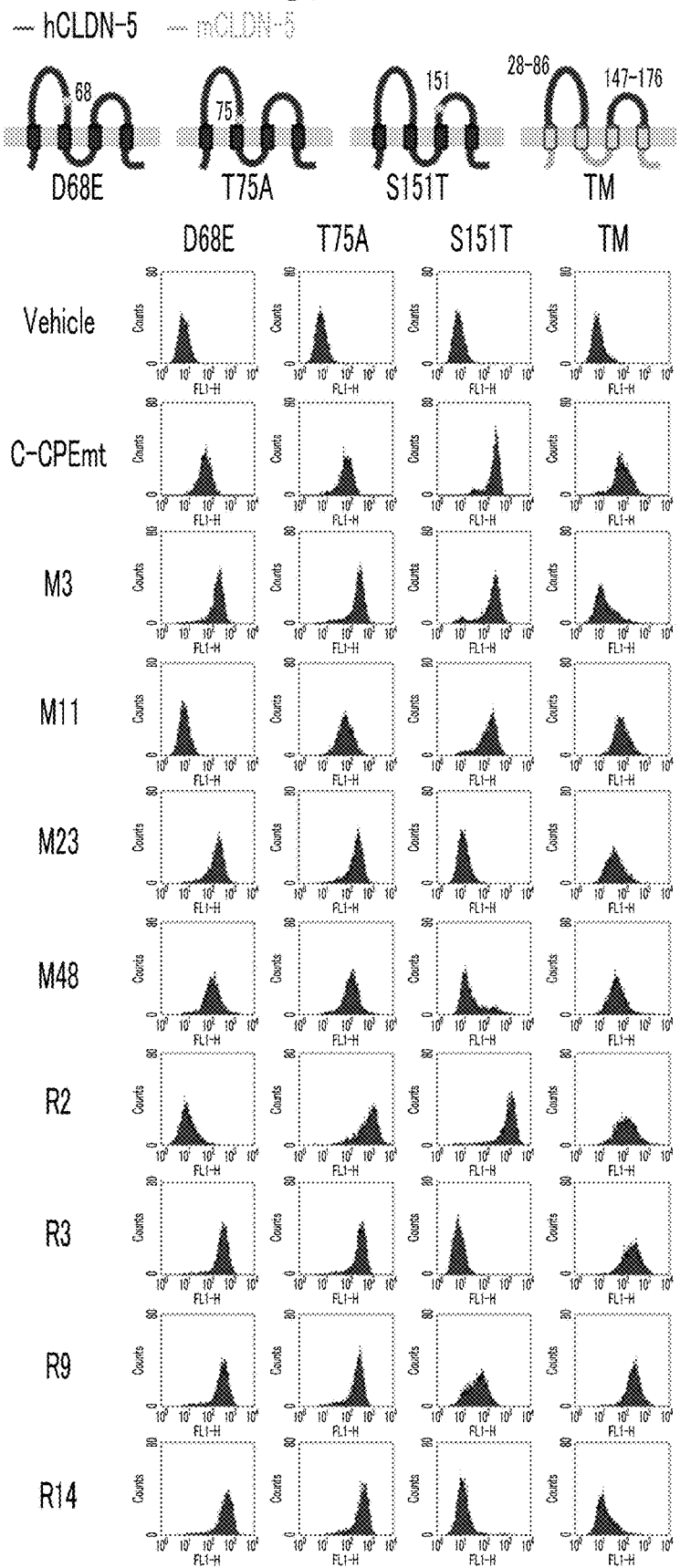
FIG. 4 illustrates FACS histograms showing which portion is necessary for the anti-CLDN-5 antibodies obtained in Example 3-5) to recognize CLDN-5. The names of CLDN-5 mutants, which are obtained by substituting the extracellular domain of CLDN-5 expressed in cells by using a retrovirus with the extracellular domain of CLDN-1, are shown at the top of the histograms, and the CLDN-5 mutants are schematically illustrated on the names. The antibodies used as primary antibodies are shown on the very left side of the histograms. In each of the histograms, the abscissa shows a fluorescence signal, and the ordinate shows a cell count, "Vehicle" means that the primary antibodies are not reacted.

In the same manner as in Example 1-2), a DNA fragment encoding chimeric proteins of a wild-type human CLDN-5 protein and a wild-type human CLDN-5 protein [1-1-5: a protein obtained by substituting the first extracellular loop in the human CLDN-5 protein with the sequence of the human CLDN-1 protein (SEQ ID NO: 45). 1-5-5: a protein obtained by substituting approximately ½ of the first extracellular loop on the N-terminal side in the human CLDN-5 protein with the sequence of the human CLDN-1 protein (SEQ ID NO: 46). 5-1-5: a protein obtained by substituting approximately ½ of the first extracellular loop on the C-terminal side in the human CLDN-5 protein with the sequence of the human CLDN-1 protein (SEQ ID NO: 47), 5-5-1: a protein obtained by substituting the second extracellular loop in the human CLDN-5 protein with the sequence of the human CLDN-1 protein (SEQ ID NO: 48)] was inserted into a pCX4pur vector, thereby obtaining vectors for preparing a retrovirus. By using these vectors and the vector for preparing a retrovirus prepared in Example 1-2), various chimeric CLDN protein-expressing cells were prepared. By using these cells and the antibodies (antibody concentration: 5 μg/mL, as primary antibody), FACS assay was performed in the same manner as in Example 3-1). FIG. 4 illustrates histograms in which the abscissa shows the fluorescence signal and the ordinate shows the cell count.

Figure 3:
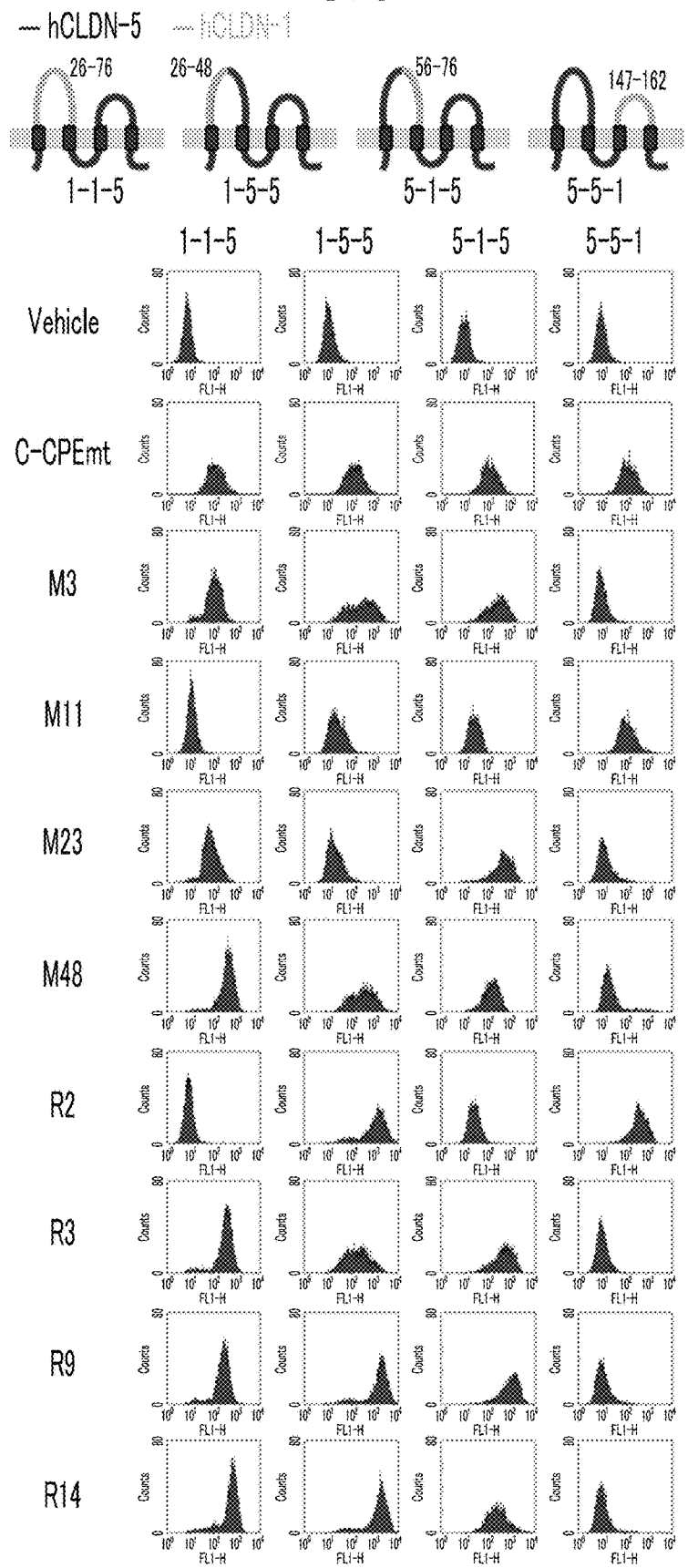
FIG. 3 illustrates FACS histograms showing to which extracellular domain the anti-CLDN-5 antibodies obtained in Example 3-4) bind between the first and second extracellular domains of CLDN-5. The names of CLDN-5 mutants, which are, obtained by substituting the extracellular domain of CLDN-5 expressed in cells by using a retrovirus with the extracellular domain of CLDN-1, are shown on the top of the histograms, and the CLDN-5 mutants are schematically illustrated on the names. The antibodies used as primary antibodies are shown at the very left side of the histograms. In each of the histograms, the abscissa shows a fluorescence signal, and the ordinate shows a cell count. "Vehicle" means that the primary antibodies are not reacted.

From FIG. 3, it has been found that the antibodies M11 and R2 recognize the first extracellular loop because these antibodies are incapable of recognizing 1-1-5 but capable of recognizing 5-5-1, and the antibodies M3, M23, M48, R3, R9, and R14 recognize the second extracellular loop because these antibodies are incapable of recognizing 5-5-1 but capable of recognizing 1-1-5. Furthermore, it has been found that although the antibodies M11 and R2 recognize the first extracellular loop, R2 is capable of recognizing 1-5-5 while M11 is incapable of recognizing 1-5-5, and accordingly, these antibodies recognize different three-dimensional structures of CLDN-5.

Example 3-5) Epitope Analysis by hCLDN-5/mCLDN-5 Chimeric CLDN

In the same manner as in Example 1-2), a DNA fragment encoding a point mutant of an hCLDN-5 protein [D68E: a protein obtained by mutating the $68^{th}$ amino acid (aspartic acid) from the N-terminal in the hCLDN-5 protein into glutamic acid (amino acid at the corresponding position in the mCLDN-5 protein) (SEQ ID NO: 41), T75A: a protein obtained by mutating the 75th amino acid (threonine) from the N-terminal in the mCLDN-5 protein into alanine (amino acid at the corresponding position in the mCLDN-5 protein) (SEQ ID NO: 42), S151T: a protein obtained by mutating the $151^{st}$ amino acid (serine) from the N-terminal in the hCLDN-5 protein into threonine (amino acid at the corresponding position in the mCLDN-5 protein) (SEQ ID NO: 43)] and a domain substitution product [TM: a protein obtained by substituting the hCLDN-5 protein, except for the $28^{th}$ to $86^{th}$ amino acids from the N-terminal containing the first extracellular loop domain in the hCLDN-5 protein and the $147^{th}$ to $176^{th}$ amino acids from the N-terminal containing the second extracellular loop domain in the hCLDN-5 protein, with amino acids at the corresponding positions in the mCLDN-5 protein (SEQ ID NO: 44)] was inserted into a Pcx4pur vector, thereby obtaining vectors for preparing a retrovirus. By using these vectors and the vector for preparing a retrovirus prepared in Example 1-2), various chimeric CLDN protein-expressing cells were prepared. By using these cells and the antibodies (antibody concentration: 5 μg/mL, as primary antibodies). FACS assay was performed in the same manner as in Example 3-1). FIG. 3 illustrates histograms in which the abscissa shows the fluorescence signal and the ordinate shows the cell count.

From FIG. 4, it has been revealed that M3 and R14 recognize the three-dimensional structure created by the transmembrane domain of hCLDN-5, M11 and R2 recognize the domain around the $68^{th}$ amino acid from the N-terminal present in the first extracellular loop, and M23, M48, R3, R9, and R14 recognize the domain around the $151^{st}$ amino acid from the N-terminal present in the second extracellular loop.

Example 3-6) Checking Western Blotting Operability

Cell lysates were prepared from HT-1080/mock and HT-1080/hCLDN-5 obtained in Example 1-2), and the lysates were separated by SDS-PAGE under a reducing condition. By using the antibodies (antibody concentration: 10 μg/mL) obtained in Example 1 as primary antibodies, western blotting was performed according to the conventional method. As primary antibodies, commercial monoclonal antibodies (4C3C2, Invitrogen, 35-2500) recognizing the C-terminal of CLDN-5 were used as positive control, and β actin antibodies (Sigma Aldrich, A1978) were used as loading control. The results are illustrated in FIG. 5.

Figure 5:
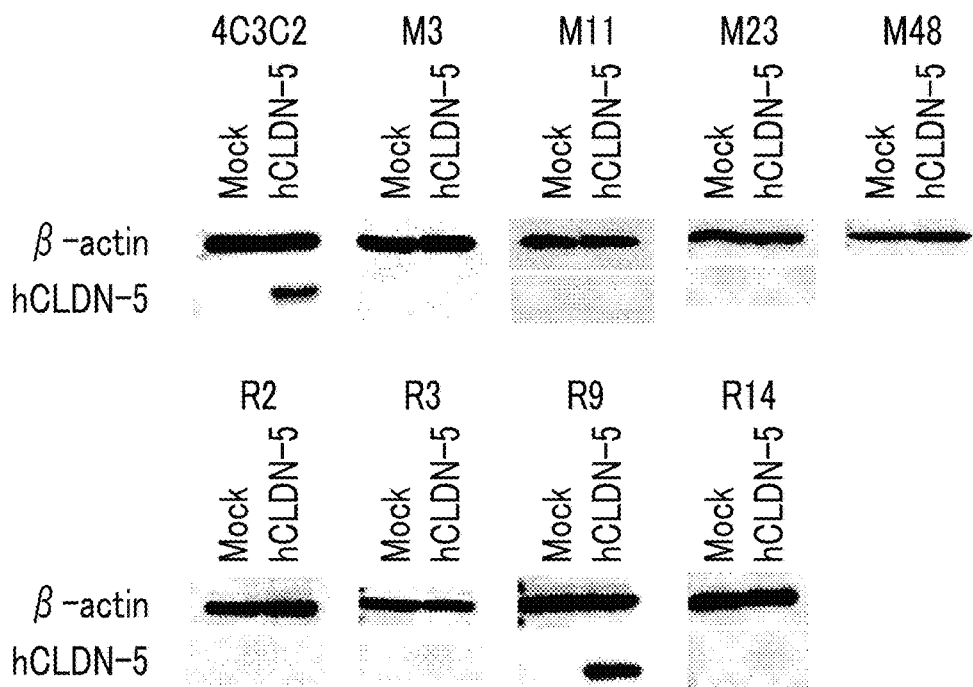
FIG. 5 illustrates western blotting images showing the CLDN-5 primary structure recognizability of the anti-CLDN-5 antibodies obtained in Example 3-6). The primary antibodies used are shown at the top of the images, and the used cells are shown under the primary antibodies. The names of proteins represented by bands are shown on the left side of the images.

As is evident from FIG. 5, the antibody R9 strongly recognized a linear peptide while the antibody R14 weakly recognized a linear peptide. It was confirmed that the antibodies which do not exhibit western blotting operability recognize the three-dimensional structure of CLDN-5.

Example 4) Evaluation of Barrier Control Activity of Antibody by Using CLDN-5 Compulsory Expression System Example 4-1) Preparation of Cell In the same manner as in Example 1-2), a DNA fragment consisting of a cCLDN-5 protein (SEQ ID NO: 28)-encoding sequence or an mCLDN-5 protein (SEQ ID NO: 29)-encoding sequence was inserted into a pCX4pur vector, thereby obtaining vectors for preparing a retrovirus. By using these vectors and the vector for preparing a retrovirus prepared in Example 1-2), various animal CLDN-5 protein-expressing MDCKII cells were prepared (MDCKII/mock, MDCKII/hCLDN-5, MDCKII/cCLDN-5, and MDCKII/mCLDN-5). These cells were cultured in a culture medium 3*.

*Culture medium 3: DMEM (NISSUI)+10% FBS (NICHIREI CORPORATION.), 50 μg/mL Penicillin/Streptomycin (NACALAI TESQUE, INC., 26253-84), 2 mM L-Glutamine (NACALAI TESQUE, INC., 04260-64).

Example 4-2) Measurement Transepithelial/Transendothelial Electrical Resistance (TEER) of CLDN-5 Compulsory Expression System A single-layer culture insert (BD Falcon, 353095) as a permeable membrane with bottom surface made of polyethylene terephthalate (pore size: 0.4 μm, $1.6 \times 10^6$ pores/cm$^2$) was set in each of the wells of a 24-well plate, and the MDCKII/mock, MDCKII/hCLDN-5, MDCKII/cCLDN-5, and MDCKII/mCLDN-5 cells prepared in Example 4-1) were cultured on the membrane. After the cells were found to become confluent through microscopic observation, TEER was evaluated on a daily bases by using a MILLICELL ERS resistance measurement system (Milipore).

Figure 6:
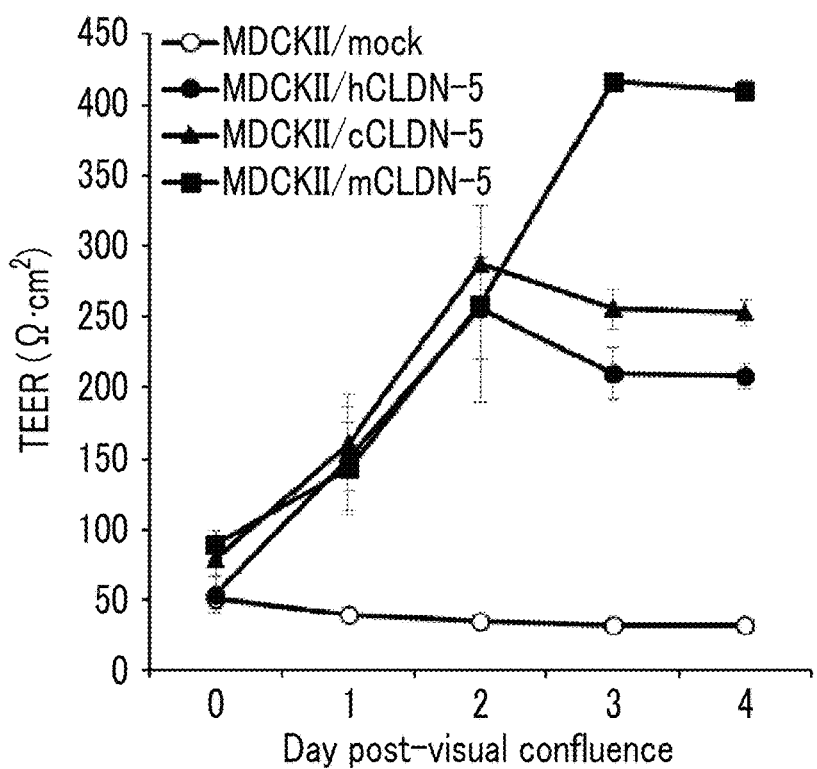
FIG. 6 illustrates results of daily variation of TEER of cells prepared by compelling MDCKII obtained in Example 4-2) to express CLDN-5 of various animal species by using a retrovirus. The ordinate shows TEER, and the abscissa shows the number of days elapsing after the cells become confluent.

As is evident from FIG. 6, while TEER of the MDCKII/mock cells was stabilized at a low value (approximately 30 to 40 Ω·cm$^2$), TEER of the MDCKII/hCLDN-5, MDCKII/cCLDN-5, and MDCKII/mCLDN-5 cells was stabilized at a high value (approximately 200 to 220, 240 to 260, and 390 to 420 Ω·cm$^2$ respectively).

Figure 7A:
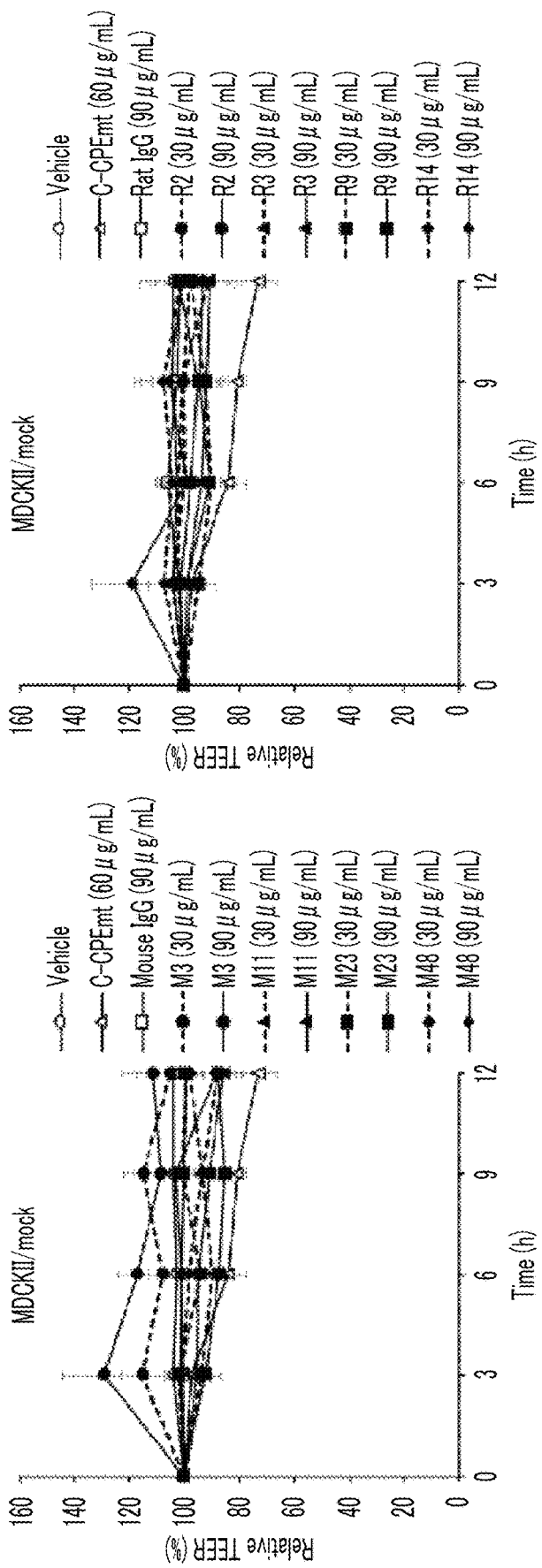
FIGS. 7A to 7D illustrate results of temporal variation of TEER observed in a case where cells, which are prepared by compelling MDCKII obtained in Example 4-3) to express CLDN-5 of various animal species by using a retrovirus, are treated with the anti-CLDN-5 antibody. The abscissa shows time elapsing after the addition of a test substance, and the ordinate shows a value obtained by dividing the value of TEER measured at each time by a value of TEER measured at the start of test and converting the obtained value into a percentage. The concentration shown in each graph represents a concentration of each test substance in a medium. "Vehicle" means that a liquid used for diluting antibodies is added. Each plot is an average (n a 3), and a bar represents a standard deviation.
Figure 7B:
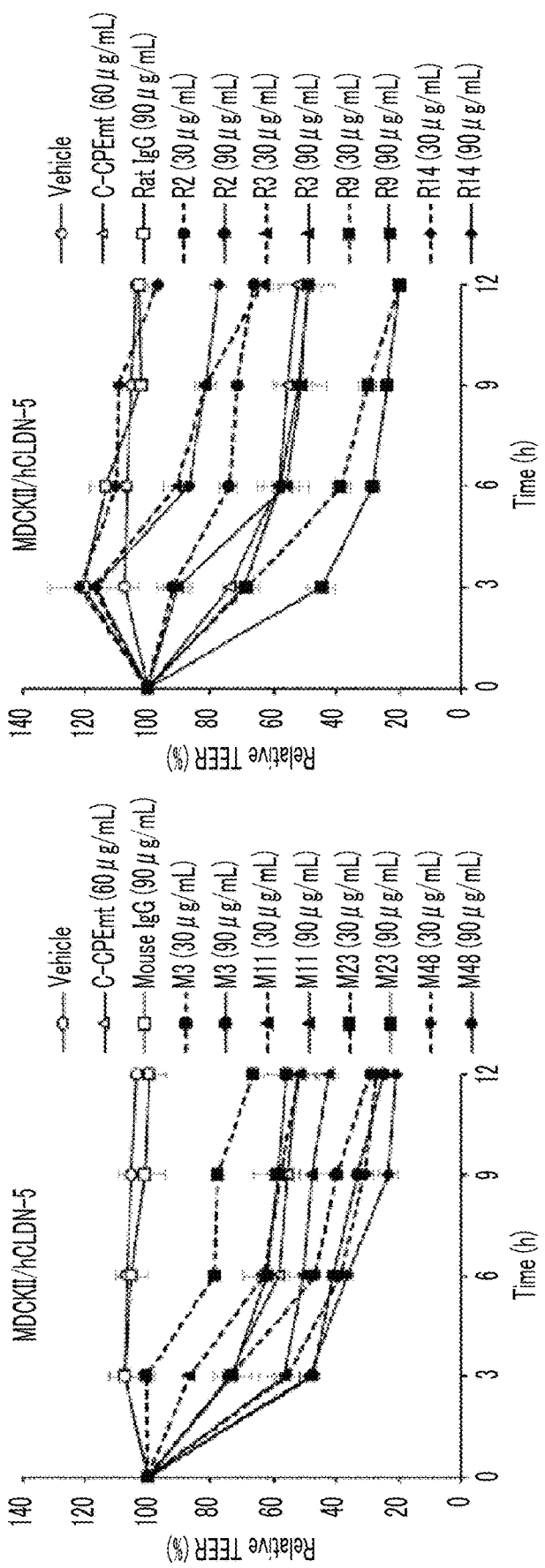
Figure 7C:
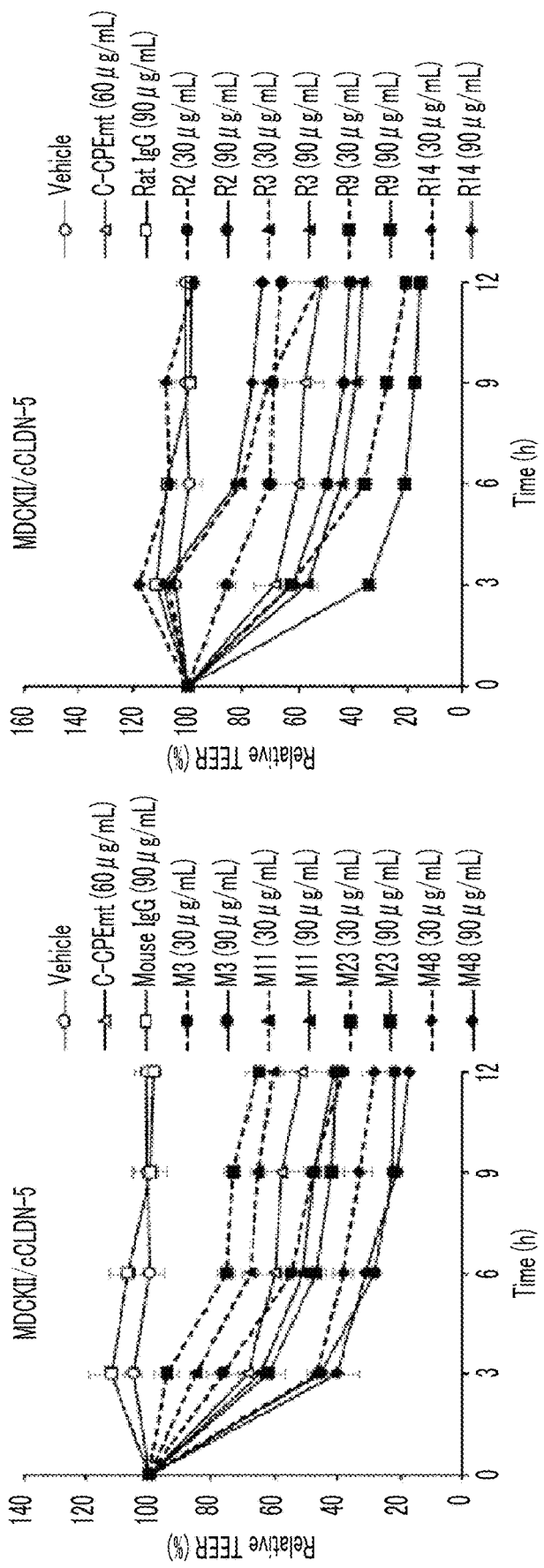
Figure 7D:
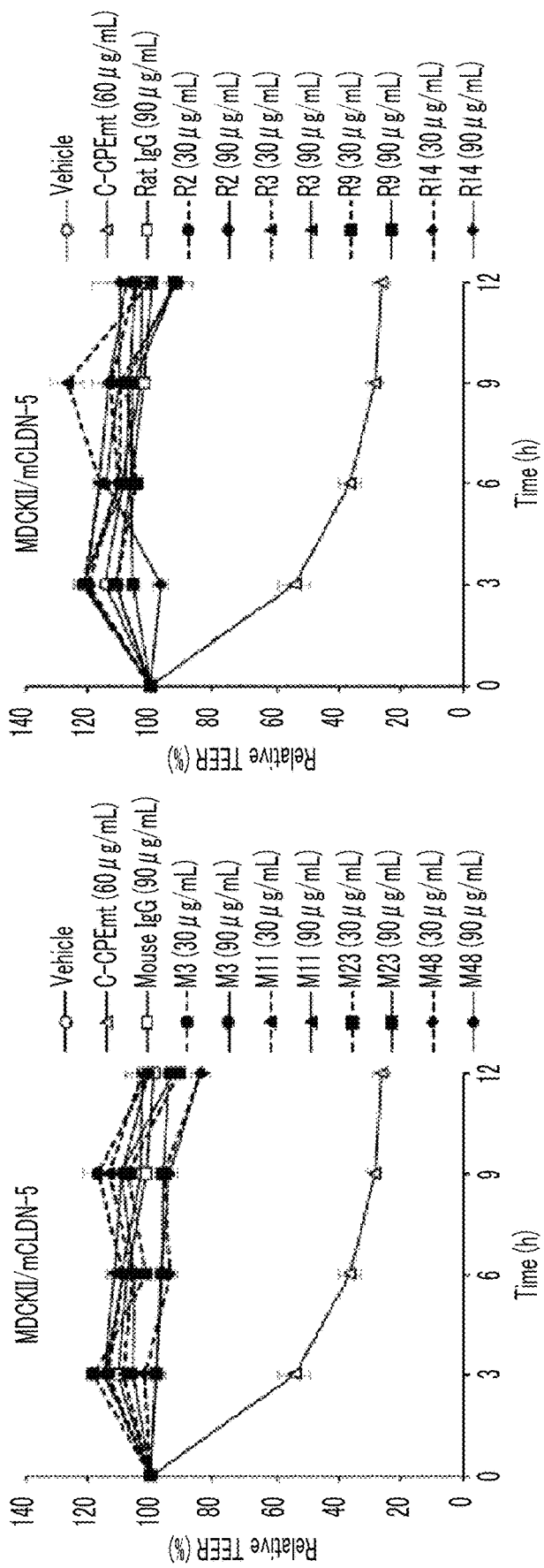
Figure 8A:
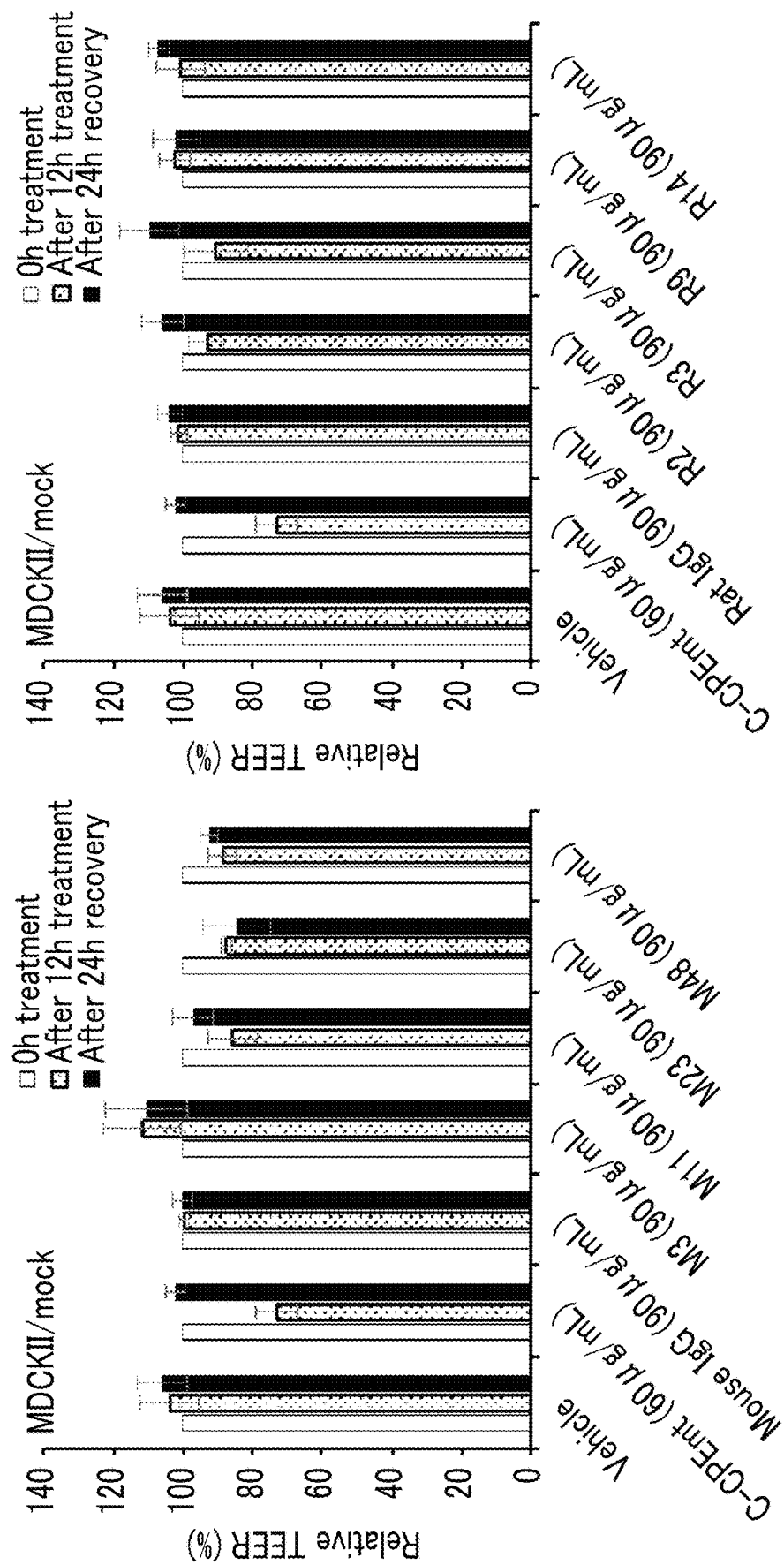
FIGS. 8A to 8D illustrate results obtained by treating cells, which are prepared by compelling MDCKII obtained in Example 4-3) to express CLDN-5 of various animal species by using a retrovirus, with the anti-CLDN-5 antibody, replacing the medium 12 hours after the treatment, culturing the cells for 24 hours, and then measuring TEER. The abscissa shows a value obtained by dividing the value of TEER measured at each time by the value of TEER at the start of test and converting the obtained value into a percentage. The ordinate shows the name and the concentration of each of the test substances. The columns show TEER measured at the start of test, immediately before replacing media, and 24 hours after the replacement of media. "Vehicle" means that a liquid used for diluting antibodies is added. Each value is an average (n=3), and a bar represents a standard deviation.
Figure 8B:
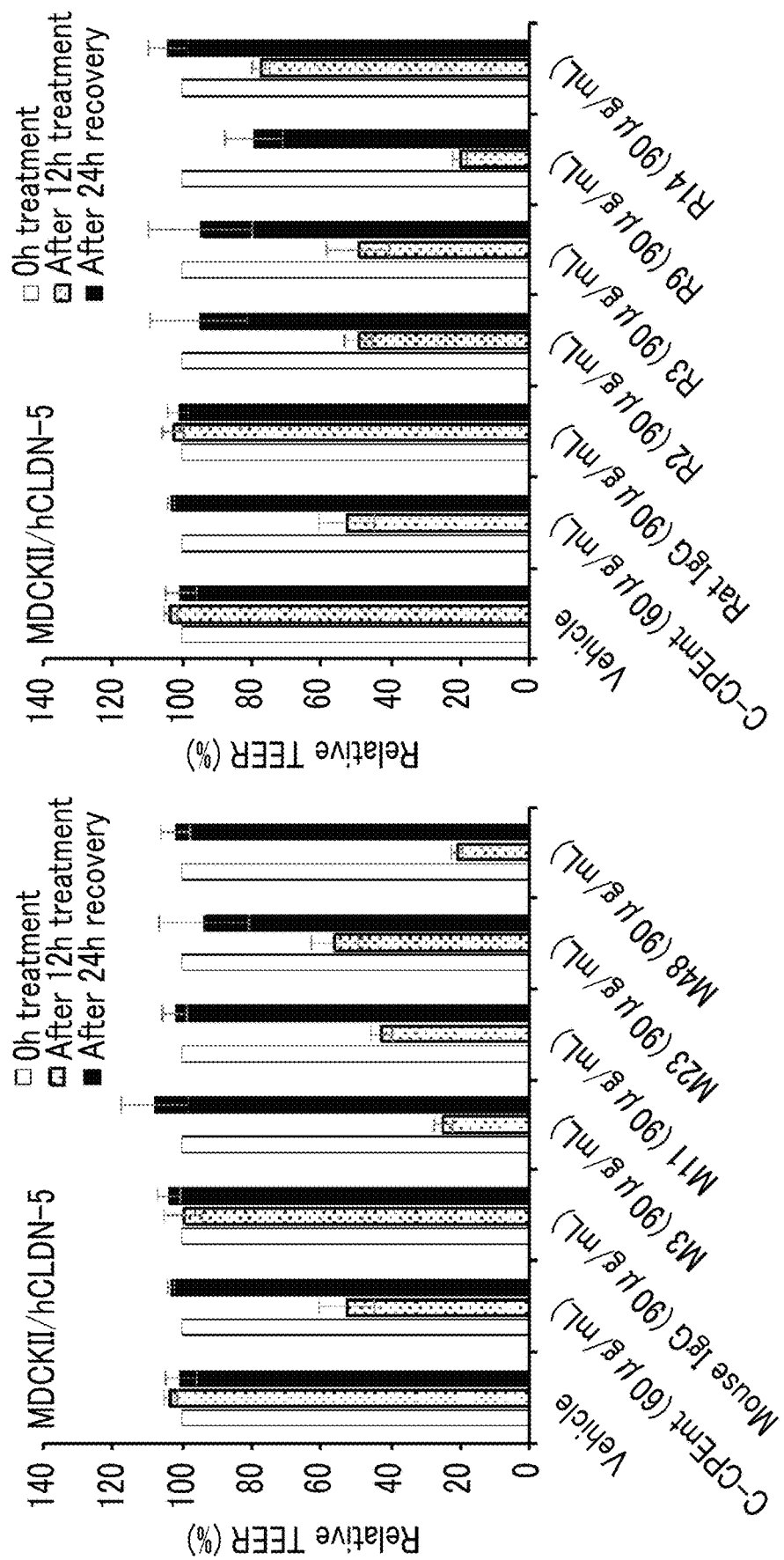
Figure 8C:
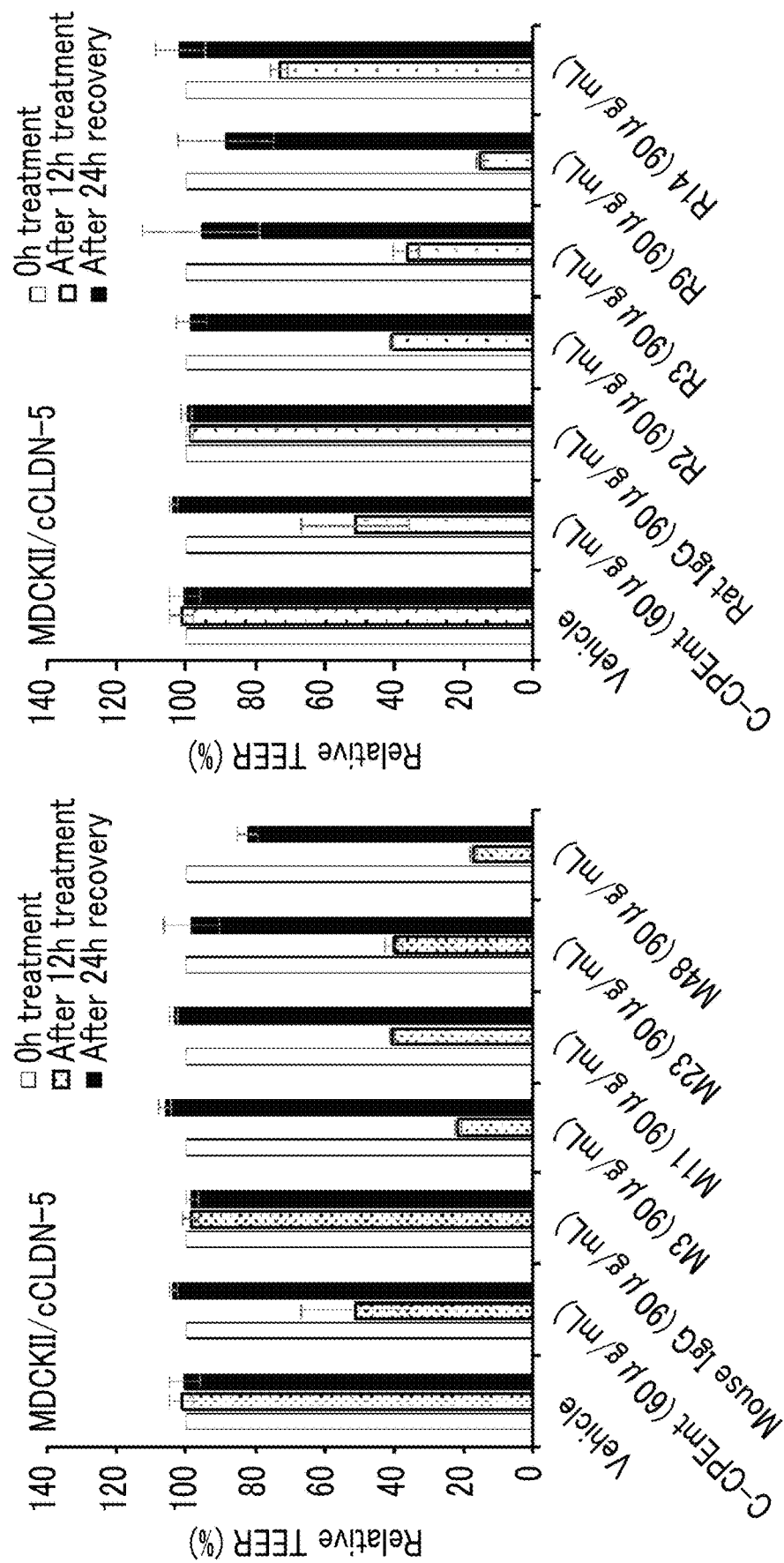
Figure 8D:
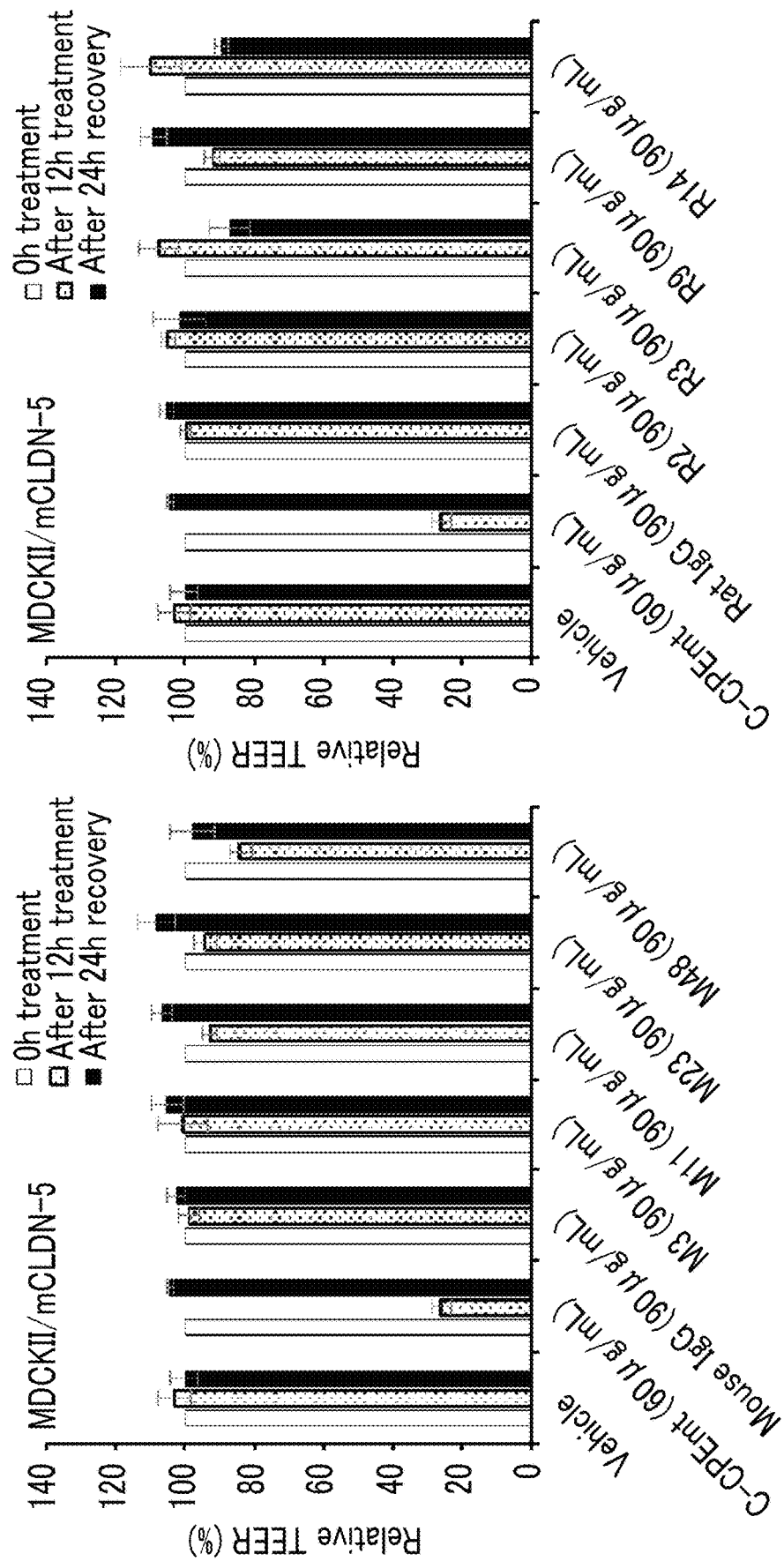

Example 4-3) Evaluation of Influence of Antibody Treatment on TEER of CLDN-5 Compulsory Expression System Cells were cultured in the same manner as in Example 4-2). After the value of TEER was stabilized, the antibodies obtained in Example 1-4), control IgG, or the solution used for diluting the antibodies was added to culture wells on the lower side in an amount of 90 µL. As positive control, C-CPEmt used in Non-Patent Literature 3 was used. Then, by using the MILLICELL ERS resistance measurement system (Milipore). TEER was temporally evaluated. The results are illustrated in FIGS. 7A to 7D. Furthermore, 12 hours after the addition of the antibodies, the cells were washed three times with the culture medium 3 and continuously cultured for 24 hours in the culture medium 3, and whether TEER changing by the addition of the antibodies is reversibly restored was evaluated. The results are illustrated in FIG. 7B.

As is evident from FIGS. 7A to 7D, while C-CPEmt as positive control induced a reduction in TEER in all of the MDCKII/mock, MDCKII/hCLDN-5, MDCKII/cCLDN-5, and MDCKII/mCLDN-5, the anti-CLDN-5 antibody induced a reduction in TEER only in MDCKII/hCLDN-5 and MDCKII/cCLDN-5. This trend correlates with the cross-species activity of the anti-CLDN-5 antibody. It has been revealed that the TEER reducing activity of the antibody is dependent on the dose of the antibody, and there are antibodies such as M3, M48, and R9 having an activity of greatly reducing TEER.

As is evident from FIG. 8A to FIG. 8D, in a case where the antibodies are fully removed from the culture medium immediately after the antibody treatment and then cultured for 24 hours, TEER reduced by each of the anti-CLDN-5 antibodies can be restored to a value equivalent to TEER measured before the addition of the antibodies. This shows that the anti-CLDN-5 antibody reversibly acts.

Example 4-4) Evaluation of Influence of Antibody Treatment on Material Permeability of CLDN-5 Compulsory Expression System Cells were cultured in the same manner as in Example 4-2). After the value of TEER was stabilized, the antibodies obtained in Example 1-4), C-CPEmt, control IgG, or the solution used for diluting the antibodies was added to culture wells on the lower side in an amount of 90 µL. As positive control. C-CPEmt obtained in Non-Patent Literature 3 was used. 12 Hours after the addition of the antibodies, the cells were moved to a 24-well plate containing a test medium* by using a single-layer culture insert, and the medium of the insert was replaced with the test medium. Then, the single-layer culture insert was moved to the 24-well plate kept warm on a HIENAI plate warmer containing the test medium, the medium of the insert was replaced with the test medium containing 100 µg/mL sodium fluorescein (Wako Pure Chemical Industries, Ltd.) or 10 mg/mL 4 kDa FITC-dextran (Sigma Aldrich), and the cells were measured for 30 minutes (the operation was individually performed for each insert). Thereafter, the test medium in the culture wells on the lower side was collected, and the fluorescence intensity in the medium was measured using TriSTAR LB 941 (Berthold Technologies). An apparent permeability coefficient (Papp) was calculated by the following equation; Papp (cm/s)=(amount of medium in culture well×concentration of sodium fluorescein permeating into the culture well)/(surface area of permeable membrane of insert×concentration of fluorescent material added to insert×experiment time). FIG. 9 illustrates the results obtained in a case where sodium fluorescein was added, and FIG. 10 illustrates the results obtained in a case where 4 kDa FITC-dextran was added.

As is evident from FIG. 9, while C-CPEmt as positive control improved the permeability of sodium fluorescein in all of the MDCKII/mock, MDCKII/hCLDN-5, MDCKII/cCLDN-5, and MDCKII/mCLDN-5, the anti-CLDN-5 antibody improved the permeability of sodium fluorescein only in MDCKII/hCLDN-5 and MDCKII/cCLDN-5. This trend correlates with the cross-species activity of the anti-CLDN-5 antibody. The sodium fluorescein permeability-improving activity of the antibody is dependent on dose.

Figure 10:
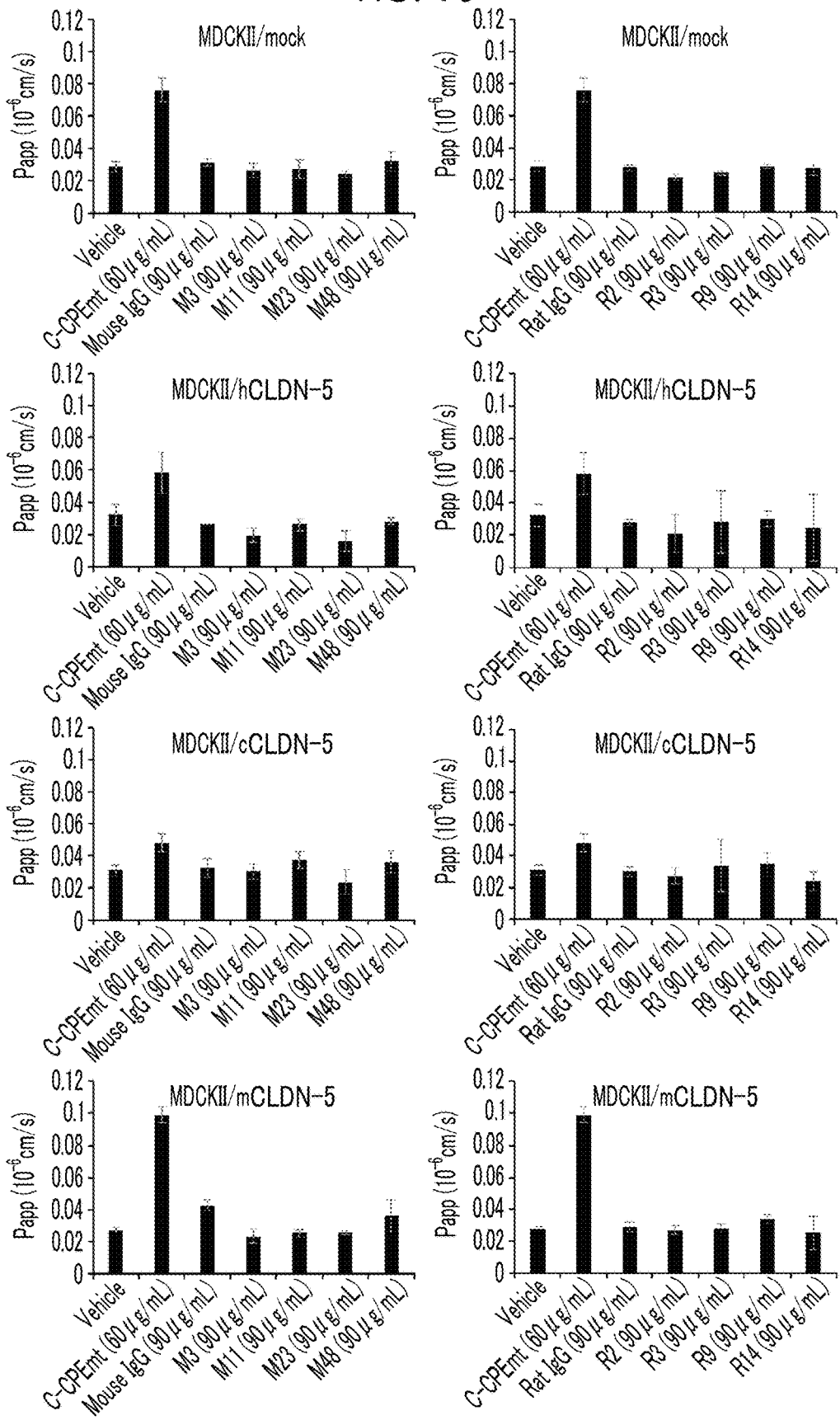
FIG. 10 illustrates results obtained by treating cells, which are prepared by compelling MDCKII obtained in Example 4.4) to express CLDN-5 of various animal species by using a retrovirus, with the anti-CLDN-5 antibody and evaluating 4 kDa FITC-dextran permeability thereof 12 hours after the treatment. The ordinate shows apparent permeability coefficients, and the abscissa shows the name and the concentration of each of the test substances, "Vehicle" means that a liquid used for diluting antibodies is added. Each value is an average (n=3), and a bar represents a standard deviation. The graphs on the first line show results obtained using MDCKII/mock, the graphs on the second line show results obtained using MDCKII/hCLDN-5, the graphs on the third line show results obtained using MDCKII/cCLDN-5, and the graphs on the fourth line show results obtained using MDCKII/mCLDN-5. The results obtained in a case where mouse antibodies are treated are shown on the left side, and the results obtained in a case where rat antibodies are treated are shown on the right side. Furthermore, the results obtained from a Vehicle-treated group and a C-CPEmt-treated group in the left and right graphs on the same line are common to both the graphs.

As is evident from FIG. 10, while C-CPEmt as positive control improved the permeability of 4 kDa FITC-dextran in all of the MDCKII/mock, MDCKII/hCLDN-5, MDCKII/cCLDN-5, and MDCKII/mCLDN-5, the anti-CLDN-5 antibody did not improve the permeability of 4 kDa FITC-dextran. *Test medium: DMEM (NISSUI)+50 µg/mL Penicillin/Streptomycin (NACALAI TESQUE, INC., 26253-84), 2 mM L-Glutamine (NACALAI TESQUE, INC., 04260-64).

Example 5) Evaluation of Barrier Control Activity of Antibody by Using Blood-Brain Barrier Simulation System Example 5-1) Evaluation of Influence of Antibody Treatment on TEER of Blood-Brain Barrier Simulation System By using a culture (monkey BBB kit, manufactured by PharmaCo-Cell Company Ltd.) simulating the blood-brain barrier, the barrier function control activity was evaluated. The culture has a structure in which an insert, which is a permeable membrane (pore size: 3.0 µm, $1.6 \times 10^6$ pores/$cm^2$) with bottom surface made of polyethylene terephthalate, is set in culture wells. On the upper side of the bottom surface of the insert a single layer-like sheet composed of brain capillary endothelial cells of a monkey is formed, and on the lower side of the bottom surface of the insert, a cell sheet composed of rat pericytes is formed. Furthermore, on the bottom surface of the culture wells, a cell sheet composed of rat astrocytes is formed. The culture was performed using the dedicated medium attached.

After the value of TEER of the culture was found to reach 150 Ω·cm, the antibodies obtained in Example 1-4), C-CPEmt, a control IgG solution, or a liquid used for diluting the antibodies was added in an amount of 30 µL to the medium of the insert (blood vessel). After the addition, the temporal change in the value of TEER was measured. The results are illustrated in FIG. 11.

Figure 11:
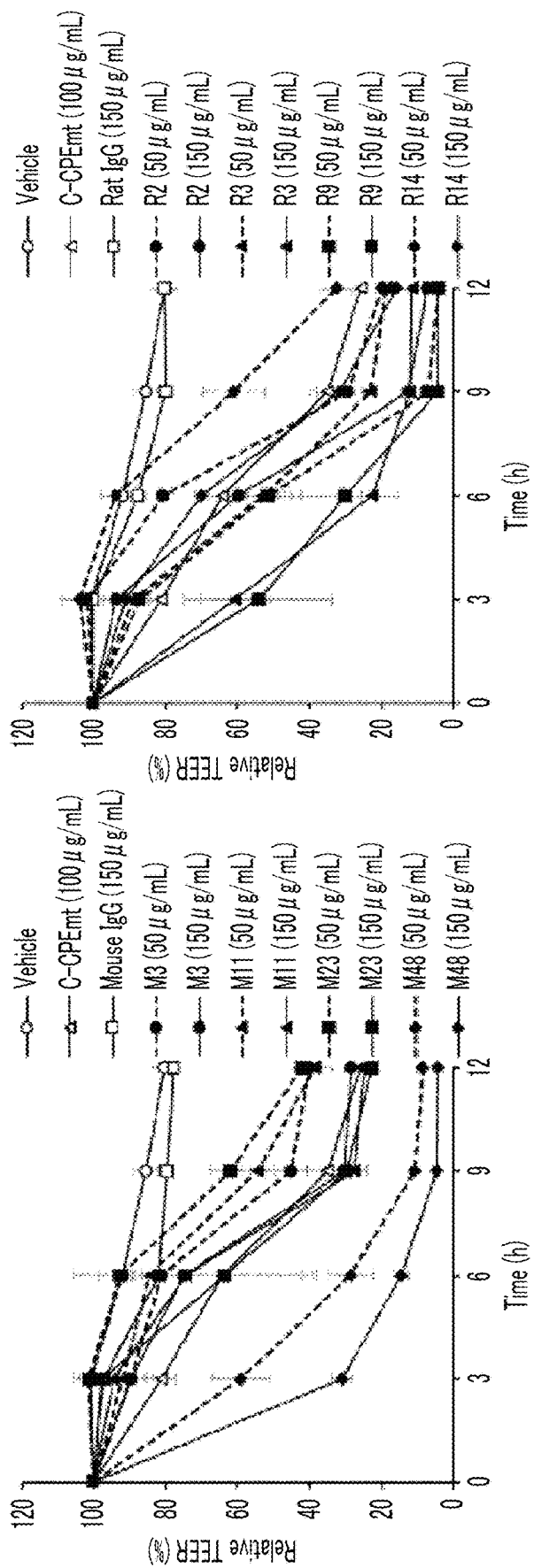
FIG. 11 illustrates results of temporal variation of TEER observed in a case where a blood-brain barrier simulation system obtained in Example 5-1) is treated with the anti-CLDN-5 antibody. The abscissa shows time elapsing after the addition of a test substance, and the ordinate shows a value obtained by dividing the value of TEER measured at each time by a value of TEER measured at the start of test and converting the obtained value into a percentage. The concentration shown in each graph represents a concentration of each test substance in a medium. "Vehicle" means that a liquid used for diluting antibodies is added. Each plot is an average (n=3), and a bar represents a standard deviation. The results obtained in a case where mouse antibodies are treated are shown on the left side, and the results obtained in a case where rat antibodies are treated are shown on the right side. Furthermore, the results obtained from a Vehicle-treated group and a C-CPEmt-treated group in the left and right graphs are common to both the graphs.

From FIG. 11, it was confirmed that each of the anti-CLDN-5 antibodies has an activity of reducing TEER of the blood-brain barrier simulation system. Furthermore, the TEER reducing activity was independent on dose.

Figure 12:
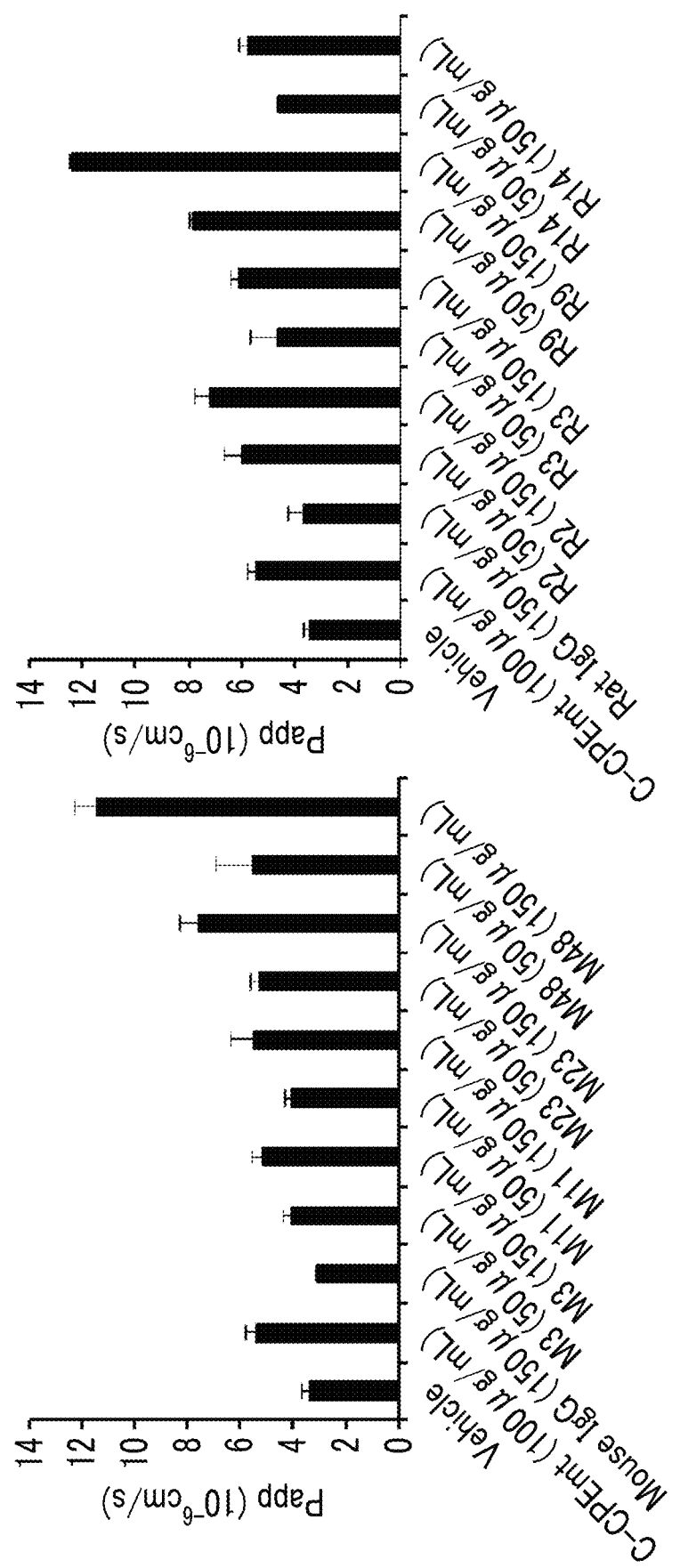
FIG. 12 illustrates results obtained by treating a blood-brain barrier simulation system obtained in Example 5-2) with the anti-CLDN-5 antibody and evaluating sodium fluorescein permeability thereof 12 hours after the treatment. The ordinate shows apparent permeability coefficients, and the abscissa shows the name and the concentration of each of the test substances. "Vehicle" means that a liquid used for diluting antibodies is added. Each value is an average (n=3), and a bar represents a standard deviation. The results obtained in a case where mouse antibodies are treated are shown on the left side, and the results obtained in a case where rat antibodies are treated are shown on the right side. Furthermore, the results obtained from a Vehicle-treated group and a C-CPEmt-treated group in the left and right graphs are common to both the graphs.

Example 5-2) Evaluation of Influence of Antibody Treatment on Material Permeability of Blood-Brain Barrier Simulation System After the value of TEER of the monkey BBB kit was found to reach 150 Ω·cm², the antibodies obtained in Example 1-4), C-CPEmt, a control IgG solution, or the liquid used for diluting the antibodies was added in an amount of 30 µL to the medium in the insert of the culture (blood vessel). Twelve hours after the addition, the permeability of a fluorescent material (10 μg/mL sodium fluorescein or 1 mg/mL 4 kDa FITC-dextran) was evaluated in the same manner as in Example 4-3). FIG. 12 illustrates the result obtained in a case where sodium fluorescein was added, and FIG. 13 illustrates the results obtained in a case where 4 kDa FITC-dextran was added.

From FIG. 12, it was confirmed that each of the anti-CLDN-5 antibodies has an activity of improving sodium fluorescein permeability of the blood-brain barrier simulation system. Furthermore, the sodium fluorescein permeability-improving activity was dependent on dose.

Figure 13:
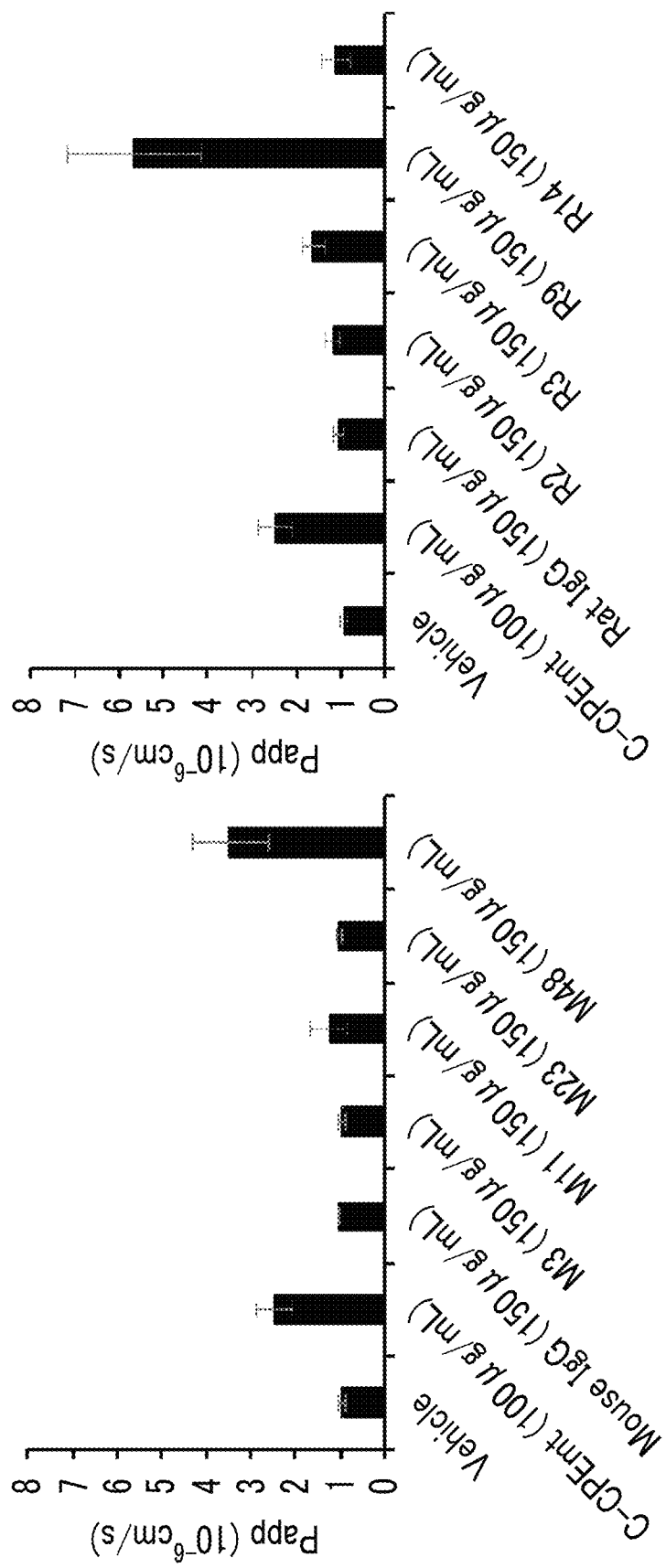
FIG. 13 illustrates results obtained by treating the blood-brain barrier simulation system obtained in Example 5-2) with the anti-CLDN-5 antibody and evaluating 4 kDa FITC-dextran permeability thereof 12 hours after the treatment. The ordinate shows apparent permeability coefficients, and the abscissa shows the name and the concentration of each of the test substances. "Vehicle" means that a liquid used for diluting antibodies is added. Each value is an average (n=3), and a bar represents a standard deviation. The results obtained in a case where mouse antibodies are treated are shown on the left side, and the results obtained in a case where rat antibodies are treated are shown on the right side. Furthermore, the results obtained from a Vehicle-treated group and a C-CPEmt-treated group in the left and right graphs are common to both the graphs.

As is evident from FIG. 13, among the anti-CLDN-5 antibodies, only M48 and R9 exhibited an activity of improving the 4 kDa FITC-dextran permeability of the blood-brain barrier simulation system. This result correlates to the potency of activity of the antibody.

Example 5-3) Evaluation of Influence of Antibody Treatment on CLDN-5 Localization Properties in Blood Brain Barrier Simulation System After the value of TEER of the monkey BBB kit was found to reach 150 Ω·cm$^2$, the antibodies obtained in Example 1-4), C-CPEmt, or the liquid used for diluting the antibodies was added in an amount of 30 μL to the medium in the insert of the culture (blood vessel). Twelve hours after the addition, the cells were washed with PBS, pericytes attached to the lower portion of the insert were scraped using a scraper, and an immobilization operation was performed using 4% PFA-PBS, Thereafter, a permeabilization treatment was performed using 0.1% triton-X, and then a blocking operation was performed using 1% BSA-PBS. Subsequently, by using rabbit anti-ZO-1 (Thermo Fisher Scientific) or rabbit anti-CLDN-5 (SigmaAldrich) as a primary antibody and Alexa488 conjugated goat anti-rabbit (Jackson ImmuneReseach) as a secondary antibody, immunostaining was performed. The cells were observed using a fluorescence microscope (Keyence, BZ-X910). The results are illustrated in FIG. 14.

Figure 14:
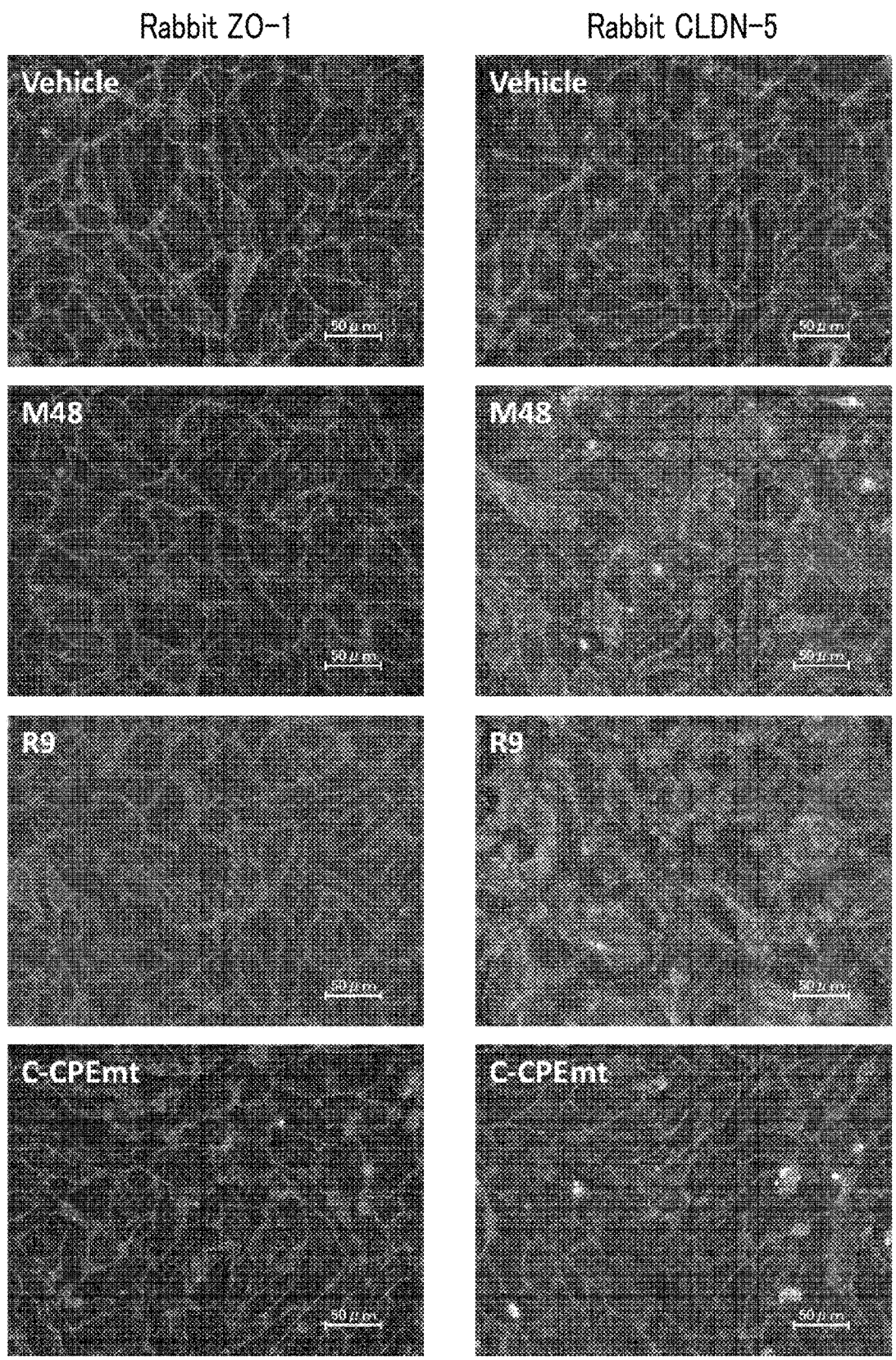
FIG. 14 illustrates results obtained by treating a blood-brain barrier simulation system obtained in Example 5-3) with the anti-CLDN-5 antibody and evaluating the localization properties of ZO-1 and CLDN-5 by immunostaining 12 hours after the treatment. The primary antibodies used are shown at the top of the images. The images of stained ZO-1 are shown on the left side, and the images of stained CLDN-5 are shown on the right side. The name of a test substance treated is shown on the left upper side of each of the images. "Vehicle" means that a liquid used for diluting antibodies is added.

As is evident from FIG. 14, even though ZO-1 was treated with Vehicle, M48, R9, and C-CPEmt, the localization properties thereof did not change, and ZO-1 remained localized in the intercellular space. In contrast, the localization properties of CLDN-5 in the intercellular space were reduced by the treatment with M48 and R9, and CLDN-5 was found to be dispersed on the cell surface. Presumably, the phenomenon in which the localization properties of CLDN-5 changes may be closely related to the barrier function reducing mechanism of the anti-CLDN-5 antibody.

Sequence Listing

P18-020WO_PCT_ANTI-CLDN-5 ANTIBODY, _20180425_13502_6.txt

---

The invention claimed is:

1. An antibody which specifically recognizes a three-dimensional structure or a primary structure of an extracellular domain of a Claudin-5 protein and wherein the antibody is selected from the group consisting of:
(A) antibody A comprising a heavy chain variable region comprising
   a heavy chain CDR1 comprising the amino acid sequence represented by SEQ ID NO: 50,
   a heavy chain CDR2 comprising the amino acid sequence represented by SEQ ID NO: 52,
   a heavy chain CDR3 comprising the amino acid sequence represented by SEQ ID NO: 54, and
   a light chain variable region comprising
   a light chain CDR1 comprising the amino acid sequence represented by SEQ ID NO: 141,
   a light chain CDR2 comprising the amino acid sequence represented by SEQ ID NO: 143, and
   a light chain CDR3 comprising the amino acid sequence represented by SEQ ID NO: 145;
(B) antibody B comprising a heavy chain variable region comprising
   a heavy chain CDR1 comprising the amino acid sequence represented by SEQ ID NO: 57,
   a heavy chain CDR2 comprising the amino acid sequence represented by SEQ ID NO: 59,
   a heavy chain CDR3 comprising the amino acid sequence represented by SEQ ID NO: 61 and
   a light chain variable region comprising
   a light chain CDR1 comprising the amino acid sequence represented by SEQ ID NO: 148,
   a light chain CDR2 comprising the amino acid sequence represented by SEQ ID NO: 150, and
   a light chain CDR3 comprising the amino acid sequence represented by SEQ ID NO: 152;
(C) antibody C comprising a heavy chain variable region comprising
   a heavy chain CDR1 comprising the amino acid sequence represented by SEQ ID NO: 64,
   a heavy chain CDR2 comprising the amino acid sequence represented by SEQ ID NO: 66, a heavy chain CDR3 comprising the amino acid sequence represented by SEQ ID NO: 68, and
a light chain variable region comprising
a light chain CDR1 comprising the amino acid sequence represented by SEQ ID NO: 155,
a light chain CDR2 comprising the amino acid sequence represented by SEQ ID NO: 157, and
a light chain CDR3 comprising the amino acid sequence represented by SEQ ID NO: 159;

(D) antibody D comprising a heavy chain variable comprising
a heavy chain CDR1 comprising the amino acid sequence represented by SEQ ID NO: 71,
a heavy chain CDR2 comprising the amino acid sequence represented by SEQ ID NO: 73,
a heavy chain CDR3 comprising the amino acid sequence represented by SEQ ID NO: 75, and
a light chain variable region comprising
a light chain CDR1 comprising the amino acid sequence represented by SEQ ID NO: 162,
a light chain CDR2 comprising the amino acid sequence represented by SEQ ID NO: 164, and
a light chain CDR3 comprising the amino acid sequence represented by SEQ ID NO: 166;

(E) antibody E comprising a heavy chain variable region comprising
a heavy chain CDR1 comprising the amino acid sequence represented by SEQ ID NO: 78,
a heavy chain CDR2 comprising the amino acid sequence represented by SEQ ID NO: 80,
a heavy chain CDR3 comprising the amino acid sequence represented by SEQ ID NO: 82, and
a light chain variable region comprising
a light chain CDR1 comprising the amino acid sequence represented by SEQ ID NO: 169,
a light chain CDR2 comprising the amino acid sequence represented by SEQ ID NO: 171, and
a light chain CDR3 comprising the amino acid sequence represented by SEQ ID NO: 173;

(F) antibody F comprising a heavy chain variable region comprising
a heavy chain CDR1 comprising the amino acid sequence represented by SEQ ID NO: 85,
a heavy chain CDR2 comprising the amino acid sequence represented by SEQ ID NO 87,
a heavy chain CDR3 comprising the amino acid sequence represented by SEQ ID NO: 89, and
a light chain variable region comprising
a light chain CDR1 comprising the amino acid sequence represented by SEQ ID NO: 176,
a light chain CDR2 comprising the amino acid sequence represented by SEQ ID NO: 178, and
a light chain CDR3 comprising the amino acid sequence represented by SEQ ID NO: 180;

(G) antibody G comprising a heavy chain variable region comprising
a heavy chain CDR1 comprising the amino acid sequence represented by SEQ ID NO: 92,
a heavy chain CDR2 comprising the amino acid sequence represented by SEQ ID NO: 94,
a heavy chain CDR3 comprising the amino acid sequence represented by SEQ ID NO: 96, and
a light chain variable region comprising
a light chain CDR1 comprising the amino acid sequence represented by SEQ ID NO: 183,
a light chain CDR2 comprising the amino acid sequence represented by SEQ ID NO: 185, and
a light chain CDR3 comprising the amino acid sequence represented by SEQ ID NO: 187;

(H) antibody H comprising a heavy chain variable region comprising
a heavy chain CDR1 comprising the amino acid sequence represented by SEQ ID NO: 99,
a heavy chain CDR2 comprising the amino acid sequence represented by SEQ ID NO: 101,
a heavy chain CDR3 comprising the amino acid sequence represented by SEQ ID NO: 103, and
a light chain variable region comprising
a light chain CDR1 comprising the amino acid sequence represented by SEQ ID NO: 190,
a light chain CDR2 comprising the amino acid sequence represented by SEQ ID NO: 192, and
a light chain CDR3 comprising the amino acid sequence represented by SEQ ID NO: 194;

(I) antibody I comprising a heavy chain variable region comprising
a heavy chain CDR1 comprising the amino acid sequence represented by SEQ ID NO: 106,
a heavy chain CDR2 comprising the amino acid sequence represented by SEQ ID NO: 108,
a heavy chain CDR3 comprising the amino acid sequence represented by SEQ ID NO: 110, and
a light chain variable region comprising
a light chain CDR1 comprising the amino acid sequence represented by SEQ ID NO: 197,
a light chain CDR2 comprising the amino acid sequence represented by SEQ ID NO: 199, and
a light chain CDR3 comprising the amino acid sequence represented by SEQ ID NO: 201;

(J) antibody J comprising a heavy chain variable region comprising
a heavy chain CDR1 comprising the amino acid sequence represented by SEQ ID NO: 113,
a heavy chain CDR2 comprising the amino acid sequence represented by SEQ ID NO: 115,
a heavy chain CDR3 comprising the amino acid sequence represented by SEQ ID NO: 117, and
a light chain variable region comprising
a light chain CDR1 comprising the amino acid sequence represented by SEQ ID NO: 204,
a light chain CDR2 comprising the amino acid sequence represented by SEQ ID NO: 206, and
a light chain CDR3 comprising the amino acid sequence represented by SEQ ID NO: 208;

(K) antibody K comprising a heavy chain variable region comprising
a heavy chain CDR1 comprising the amino acid sequence represented by SEQ ID NO: 120,
a heavy chain CDR2 comprising the amino acid sequence represented by SEQ ID NO: 122,
a heavy chain CDR3 comprising the amino acid sequence represented by SEQ ID NO: 124, and
a light chain variable region comprising
a light chain CDR1 comprising the amino acid sequence represented by SEQ ID NO: 211,
a light chain CDR2 comprising the amino acid sequence represented by SEQ ID NO: 213, and
a light chain CDR3 comprising the amino acid sequence represented by SEQ ID NO: 215;

(L) antibody L comprising a heavy chain variable region comprising
a heavy chain CDR1 comprising the amino acid sequence represented by SEQ ID NO: 127, a heavy chain CDR2 comprising the amino acid sequence represented by SEQ ID NO: 129,
a heavy chain CDR3 comprising the amino acid sequence represented by SEQ ID NO: 131, and
a light chain variable region comprising
a light chain CDR1 comprising the amino acid sequence represented by SEQ ID NO: 218,
a light chain CDR2 comprising the amino acid sequence represented by SEQ ID NO: 220, and
a light chain CDR3 comprising the amino acid sequence represented by SEQ ID NO: 222; and
(M) antibody M comprising a heavy chain variable region comprising
a heavy chain CDR1 comprising the amino acid sequence represented by SEQ ID NO: 134,
a heavy chain CDR2 comprising the amino acid sequence represented by SEQ ID NO: 136,
a heavy chain CDR3 comprising the amino acid sequence represented by SEQ ID NO: 138, and
a light chain variable region comprising
a light chain CDR1 comprising the amino acid sequence represented by SEQ ID NO: 225,
a light chain CDR2 comprising the amino acid sequence represented by SEQ ID NO: 227, and
a light chain CDR3 comprising the amino acid sequence represented by SEQ ID NO: 229.

2. The antibody according claim 1, comprising a variable region VH of the antibody has the amino acid sequence represented by SEQ ID NO: 1, 3, 5, 7, 9, 11, 13, 15, 17, 19, 21, 23, or 25 or an amino acid sequence sharing identity equal to or higher than 90% with any of these amino acid sequences, and a variable region VL of the antibody has the amino acid sequence represented by SEQ ID NO: 2, 4, 6, 8, 10, 12, 14, 16, 18, 20, 22, 24, or 26 or an amino acid sequence sharing identity equal to or higher than 90% with any of these amino acid sequences.

3. The antibody according to claim 1, wherein the antibody binds to none of extracellular domains of a Claudin-1 protein, a Claudin-2 protein, a Claudin-3 protein, a Claudin-4 protein, a Claudin-6 protein, and a Claudin-7 protein.

4. The antibody according to claim 1, wherein the antibody specifically recognizes a domain ranging from the 28$^{th}$ amino acid, proline, to the 80$^{th}$ amino acid, alanine, from the N-terminal in a human CLDN-5 protein consisting of the amino acid sequence represented by SEQ ID NO: 27.

5. The antibody according claim 1, wherein the antibody has a binding capacity to a protein 1-1-5 consisting of an amino acid sequence represented by SEQ ID NO: 45 is equal to or lower than ⅕ of a binding capacity thereof to a human Claudin-5 protein consisting of the amino acid sequence represented by SEQ ID NO: 27, wherein the protein 1-1-5 is the one where a first extracellular loop of the human Claudin-5 protein is substituted with a first loop of a human Claudin-1 protein.

6. The antibody according to claim 5, wherein the antibody has a binding capacity to a human Claudin-5 protein point mutant D68E consisting of the amino acid sequence represented by SEQ ID NO: 41 is equal to or lower than ⅕ of a binding capacity thereof to a human Claudin-5 protein consisting of the amino acid sequence represented by SEQ ID NO: 27.

7. The antibody according to claim 1, wherein the antibody specifically recognizes a domain ranging from the 147$^{th}$ amino acid, phenylalanine, to the 163$^{rd}$ amino acid, alanine, from the N-terminal in a human CLDN-5 protein consisting of an amino acid sequence represented by SEQ ID NO: 27.

8. The antibody according claim 1, wherein the antibody has a binding capacity to a protein 5-5-1 consisting of the amino acid sequence represented by SEQ ID NO: 48 is equal to or lower than ⅕ of a binding capacity thereof to a human Claudin-5 protein consisting of the amino acid sequence represented by SEQ ID NO: 27, wherein the protein 5-5-1 is the one where a second extracellular loop of the human Claudin-5 protein is substituted with a second loop of a human Claudin-1 protein.

9. The antibody according to claim 8, wherein the antibody has a binding capacity to a human Claudin-5 protein point mutant S151T consisting of the amino acid sequence represented by SEQ ID NO: 43 is equal to or lower than ⅕ of a binding capacity thereof to a human Claudin-5 protein consisting of the amino acid sequence represented by SEQ ID NO: 27.

10. The antibody according to claim 1, wherein the antibody specifically recognizes a three-dimensional structure formed of a domain ranging from the 28th amino acid, proline, to the 80th amino acid, alanine, from the N-terminal and a domain ranging from the 147$^{th}$ amino acid, phenylalanine, to the 163$^{rd}$ amino acid, alanine, from the N-terminal in a human CLDN-5 protein consisting of the amino acid sequence represented by SEQ ID NO: 27.

11. The antibody according to claim 1, wherein the antibody has a binding capacity to a mutant TM consisting of the amino acid sequence represented by SEQ ID NO: 44 is equal to or lower than ⅕ of a binding capacity thereof to a human Claudin-5 protein consisting of the amino acid sequence represented by SEQ ID NO: 27, wherein the mutant TM is the one where the human Claudin-5 protein except for an extracellular domain thereof is substituted with a mouse Claudin-5 protein.

12. A cell comprising a polynucleotide encoding the antibody according claim 1.

* * * * *